(12) United States Patent
Glik et al.

(10) Patent No.: US 12,042,293 B2
(45) Date of Patent: Jul. 23, 2024

(54) EEG MICROSTATES ANALYSIS

(71) Applicants: Mor Research Applications Ltd., Tel-Aviv (IL); Ramot at Tel-Aviv University Ltd., Tel-Aviv (IL)

(72) Inventors: Amir Glik, Tel Aviv (IL); Miriam Furst-Yust, Tel Aviv (IL); Felix Benninger, Tel Aviv (IL)

(73) Assignees: Mor Research Applications Ltd., Ramat Gan (IL); Ramot at Tel-Aviv University Ltd., Tel-Aviv (IL)

( * ) Notice: Subject to any disclaimer, the term of this patent is extended or adjusted under 35 U.S.C. 154(b) by 467 days.

(21) Appl. No.: 16/650,875

(22) PCT Filed: Sep. 21, 2018

(86) PCT No.: PCT/IB2018/057280
§ 371 (c)(1),
(2) Date: Mar. 26, 2020

(87) PCT Pub. No.: WO2019/064136
PCT Pub. Date: Apr. 4, 2019

(65) Prior Publication Data
US 2020/0237247 A1    Jul. 30, 2020

Related U.S. Application Data

(63) Continuation-in-part of application No. PCT/IB2017/055899, filed on Sep. 27, 2017.
(Continued)

(51) Int. Cl.
*A61B 5/369* (2021.01)
*A61B 5/00* (2006.01)
*A61B 5/16* (2006.01)

(52) U.S. Cl.
CPC .............. *A61B 5/369* (2021.01); *A61B 5/165* (2013.01); *A61B 5/4088* (2013.01); *A61B 5/4842* (2013.01); *A61B 5/7275* (2013.01)

(58) Field of Classification Search
CPC ... A61B 5/4836; A61B 5/4842; A61B 5/4088; A61B 5/165; A61B 5/369; A61B 5/7275; G16H 50/30
See application file for complete search history.

(56) References Cited

U.S. PATENT DOCUMENTS 5,083,571 A * 1/1992 Prichep .................. A61B 5/377
600/544
6,983,184 B2  1/2006 Price
(Continued)

FOREIGN PATENT DOCUMENTS

CA          2655126      12/2007
KR    20150136245 A  * 12/2015
(Continued)

OTHER PUBLICATIONS

J. L. Stewart, et al., "Resting Frontal EEG Asymmetry as an Endophenotype for Depression Risk: Sex-specific Patterns of Frontal Brain Asymmetry," Journal of Abnormal Psychology, vol. 119, No. 3, pp. 502-512, Aug. 2010 (Year: 2010).*
(Continued)

*Primary Examiner* — Joel Lamprecht
*Assistant Examiner* — Nyrobi Celestine

(57) ABSTRACT

Using microstate data to evaluate Alzheimer's disease including dementia and/or mild cognitive impairment and/or depression and optionally provide treatment based on the diagnosis and/or modify treatment and/or diagnosis based on response to treatment, optionally as measured using microstate data. In one example, the method includes analyzing EEG data to generate one or more EEG parameter; and generating a risk for one or both of depression and MCI
(Continued)

(mild cognitive impairment) based on said one or more EEG parameters. Optionally, the disease comprises MCI. Optionally, the disease comprises depression. Optionally, the one or more EEG parameter comprises a microstate-derived parameter. Optionally, the one or more EEG parameter comprises a microstate duration derived parameter.

20 Claims, 29 Drawing Sheets

Related U.S. Application Data

(60) Provisional application No. 62/652,361, filed on Apr. 4, 2018, provisional application No. 62/400,118, filed on Sep. 27, 2016.

(56) References Cited

U.S. PATENT DOCUMENTS

| | | | | |
|---|---|---|---|---|
| 2002/0107455 | A1* | 8/2002 | Musha | A61B 5/374 600/546 |
| 2007/0299360 | A1* | 12/2007 | Snyder | A61B 5/369 600/544 |
| 2009/0220429 | A1 | 9/2009 | Johnsen et al. | |
| 2010/0049482 | A1* | 2/2010 | He | A61B 5/374 703/2 |
| 2010/0113959 | A1 | 5/2010 | Pascual-Leone et al. | |
| 2012/0296569 | A1 | 11/2012 | Shahaf et al. | |
| 2014/0257438 | A1 | 9/2014 | Simon et al. | |
| 2015/0088024 | A1* | 3/2015 | Sackellares | A61B 5/7221 600/544 |
| 2015/0305685 | A1* | 10/2015 | Shahaf | A61B 5/369 600/409 |
| 2016/0038049 | A1* | 2/2016 | Geva | A61N 1/36135 600/300 |
| 2016/0198968 | A1* | 7/2016 | Plenz | A61B 5/24 600/544 |
| 2019/0167179 | A1* | 6/2019 | Arzy | A61B 5/7475 |

FOREIGN PATENT DOCUMENTS

| | | |
|---|---|---|
| WO | WO 2014/074638 | 5/2014 |
| WO | WO 2014/076698 | 5/2014 |
| WO | WO 2014/107795 | 7/2014 |
| WO | WO 2014/140432 | 9/2014 |
| WO | WO 2018/060878 | 4/2018 |
| WO | WO 2019/064136 | 4/2019 |

OTHER PUBLICATIONS

B. Hosseinifard et al., "Classifying depression patients and normal subjects using machine learning techniques and nonlinear features from EEG signal," Computer Methods and Programs in Biomedicine, vol. 109, pp. 339-345, 2013 (Year: 2013).*
I. R. Beck et al., "Establishing robust cognitive dimensions for characterization and differentiation of patients with Alzheimer's disease, mild cognitive impairment, frontotemporal dementia and depression," International Journal of Geriatric Psychiatry, vol. 29, pp. 624-634, 2014 (Year: 2014).*
KR-20150136245-A (Year: 2015).*
L. D. Hernandez et al., "Towards Using Microstate-Neurofeedback for the Treatment of Psychotic Symptoms in Schizophrenia. A Feasibility Study in Healthy Participants," Brain Topography, vol. 29, pp. 308-321, Nov. 2015 (Year: 2015).*
U. R. Acharya et al., "A Novel Depression Diagnosis Index Using Nonlinear Features in EEG signals," European Neurology, vol. 74, No. 1-2, pp. 1-12, Aug. 2015 (Year: 2015).*
W. K. Strik et al., "Larger topographical variance and decreased duration of brain electric microstates in depression", Journal of Neural Transmission, vol. 99, p. 213-222, Aug. 1994 (Year: 1994).*

International Search Report and the Written Opinion Dated Jan. 22, 2018 From the International Searching Authority Re. Application No. PCT/IB2017/055899. (11 Pages).
International Search Report and the Written Opinion Dated Dec. 25, 2018 From the International Searching Authority Re. Application No. PCT/IB2018/057280. (13 Pages).
APA "Clinician-Rated Dimensions of Psychosis Symptom Severity", American Psychiatric Association, 3 P., 2013.
Betzel et al. "Synchronization Dynamics and Evidence for a Repertoire of Network States in Resting EEG", Frontiers in Computational Neuroscience, 6(Art.74): 1-13, Sep. 28, 2012.
Biasiucci et al. "EEG Microstates for BCI Therapist Feedback: Preliminary Results on a Stroke Patient", International Journal of Bioelectromagnetism, 13(3): 129-130, 2011.
Britz et al. "Bold Correlates of EEG Topography Reveal Rapid Resting-State Network Dynamics", NeuroImage, 52(4): 1162-1170, Available Online Feb. 24, 2010.
Katayama et al. "Classes of Multichannel EEG Microstates in Light and Deep Hypnotic Conditions", Brain Topography, 20(1): 7-14, , Published Online Jun. 21, 2007.
Khanna et al. "Microstates in Resting-State EEG: Current Status and Future Directions", Neuroscience and Biobehavioral Reviews, 49: 105-113, Available Online Dec. 17, 2014.
Khanna et al. "Reliability of Resting-State Microstate Features in Electroencephalography", PLOS ONE, 9(12): e0114163-1-e0114163-21, Dec. 5, 2014.
Kikuchi et al. "Native EEG and Treatment Effects in Neuroleptic-Naïve Schizophrenic Patients: Time and Frequency Domain Approaches", Schizophrenia Research, 97(1): 163-172, Available Online Aug. 20, 2007.
Kinoshita et al. "Microstate Segmentation of Spontaneous Multichannel EEG Map Series Under Diazepam and Sulpiride", Pharmacopsychiatry, 28(2): 51-55, Mar. 1995.
Koenig et al. "Decreased EEG Synchronization in Alzheimer's Disease and Mild Cognitive Impairment", Neurobiology of Aging, 26(2): 165-171, Feb. 2005.
Koenig et al. "Millisecond by Millisecond, Year by Year: Normative EEG Microstates and Developmental Stages," NeuroImage 16: 41-48, 2002.
Musso et al. "Spontaneous Brain Activity and EEG Microstates. A Novel EEG/fMRI Analysis Approach to Explore Resting-State Networks", NeuroImage, 52(4): 1149-1161, Available Online Feb. 6, 2010.
Nishida et al. "EEG Microstates Associated With Salience and Frontoparietal Networks in Frontotemporal Dementia, Schizophrenia and Alzheimer's Disease", Clinical Neurophysiology, 124(6): 1106-1114, Available Online Feb. 9, 2013.
Rutherford et al. "rTMS as a Treatment of Alzheimer's Disease with and without Comorbidity of Depression: A Review," Neuroscience Journal 2013, Article ID 679389, 5 pages.
Rutherford et al. "Short and Long-Term Effects of rTMS Treatment on Alzheimer's Disease at Different Stages: A Pilot Study", Journal of Experimental Neuroscience, 9: 43-51, Published Online Jun. 3, 2015.
Smailovic et al. "Quantitative EEG Power and Synchronization Correlate With Alzheimer's Disease CSF Biomarkers", Neurobiology of Aging, 63: 88-95, Available Online Nov. 16, 2017.
Sperling et al. "Towards Defining the Preclinical Stage of Alzheimer's Disease," Criteria for Preclinical Alzheimer's Disease, Jun. 2, 2010, 14 pages.
Strik et al. "Decreased EEG Microstate Duration and Anteriorisation of the Brain Electrical Fields in Mild and Moderate Dementia of the Alzheimer Type", Psychiatry Research: Neuroimaging Section, 75(3): 183-191, Oct. 31, 1997.
Theiner et al. "Repetitive Transcranial Magnetic Stimulation in ADHD", ADHD—New Directions in Diagnosis and Treatment, Chap. 15: 331-350, 2015.
Van De Ville et al. "EEG Microstate Sequences in Healthy Humans at Rest Reveal Scale-Free Dynamics", Proc. Natl. Acad. Sci. USA, PNAS, 107(42): 18179-18184, Oct. 19, 2010.
Official Action Dated May 17, 2021 from the US Patent and Trademark Office Re. U.S. Appl. No. 16/334,786. (22 pages).

(56) References Cited

OTHER PUBLICATIONS

International Search Report and the Written Opinion Dated Apr. 18, 2023 From the International Searching Authority Re. Application No. PCT/IL2022/051318 (15 Pages).
Invitation to Pay Additional Fees, Communication Relating to the Result of the Partial International Search and the Provisional Opinion Dated Mar. 19, 2023 From the International Searching Authority Re. Application No. PCT/IL2022/051318 (4 Pages).
Koenig et al. "A Deviant EEG Brain Microstate in Acute, Neuroleptic-Naive Schizophrenics at Rest", European Archives of Psychiatry and Clinical Neuroscience, 249(4): 205-211, 1999.
Michel et al. "EEG Microstates as a Tool for Studying the Temporal Dynamics of Whole-Brain Neuronal Networks: A Review", NeuroImage, 180(Pt.B): 577-593, Published Online Dec. 2, 2017.

\* cited by examiner

Fig. 6A

| >80 | 71-80 | 61-70 | 51-60 | 41-50 | 31-40 | 20-30 | 20< | |
|---|---|---|---|---|---|---|---|---|
| 14 | 22 | 15 | 11 | 3 | 1 | 2 | 0 | Dem |
| 6 | 1 | 12 | 7 | 0 | 11 | 10 | 3 | Nor |
| 11 | 12 | 9 | 6 | 4 | 2 | 6 | 0 | Dep |

Fig. 13

Table 2: Pairwise Comparisons "SEED" clustering method

Measure: Mean Duration

| (I) Type | (J) Type | Mean Difference (I-J) | Std. Error | Sig.[b] | 95% Confidence Interval for Difference[b] | |
|---|---|---|---|---|---|---|
| | | | | | Lower Bound | Upper Bound |
| DEM | DEP | .003 | .002 | .137 | -.001 | .007 |
| | NOR | .006* | .002 | .002 | .002 | .010 |
| DEP | DEM | -.003 | .002 | .137 | -.007 | .001 |
| | NOR | .003 | .002 | .131 | -.001 | .007 |
| NOR | DEM | -.006* | .002 | .002 | -.010 | -.002 |
| | DEP | -.003 | .002 | .131 | -.007 | .001 |

Based on estimated marginal means

*. The mean difference is significant at the .05 level.

b. Adjustment for multiple comparisons: Least Significant Difference (equivalent to no adjustments).

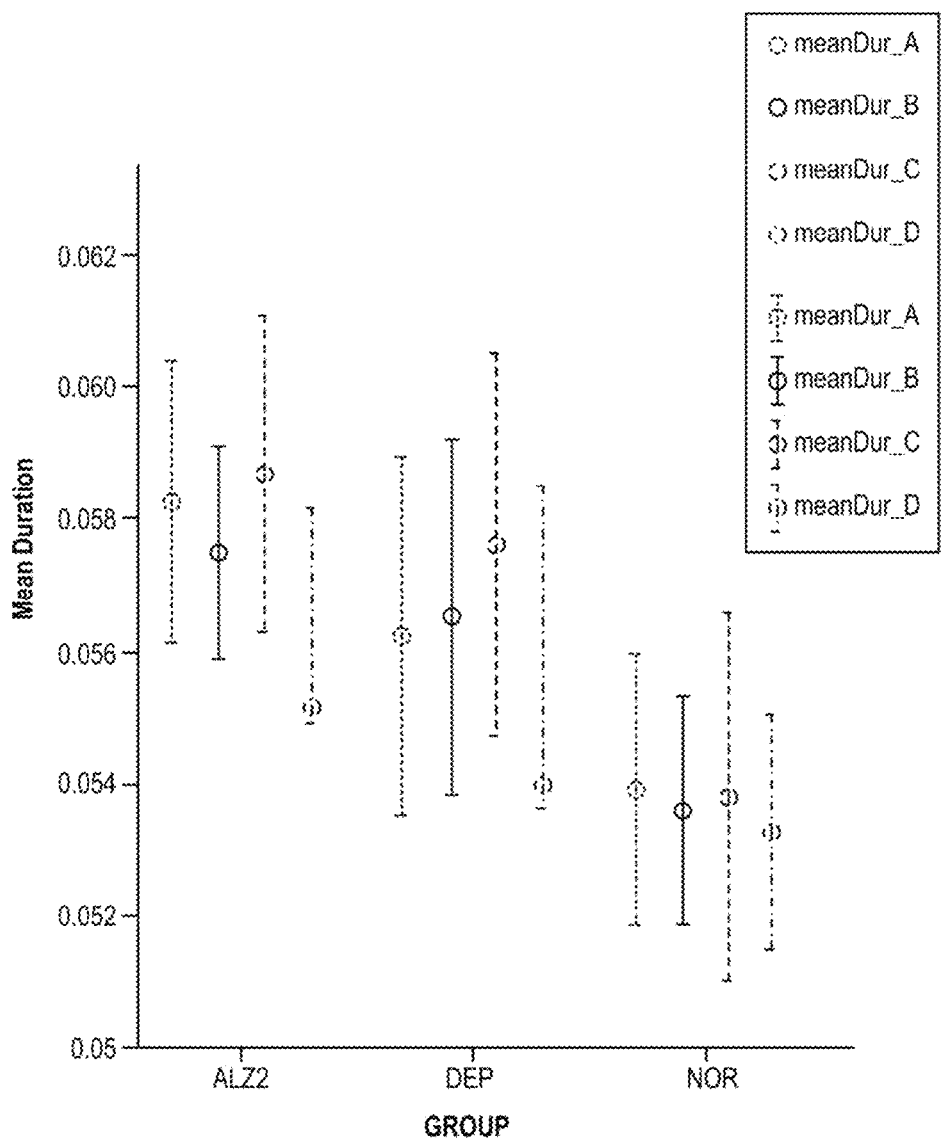
Fig. 15A  Error Bars: 95% CI

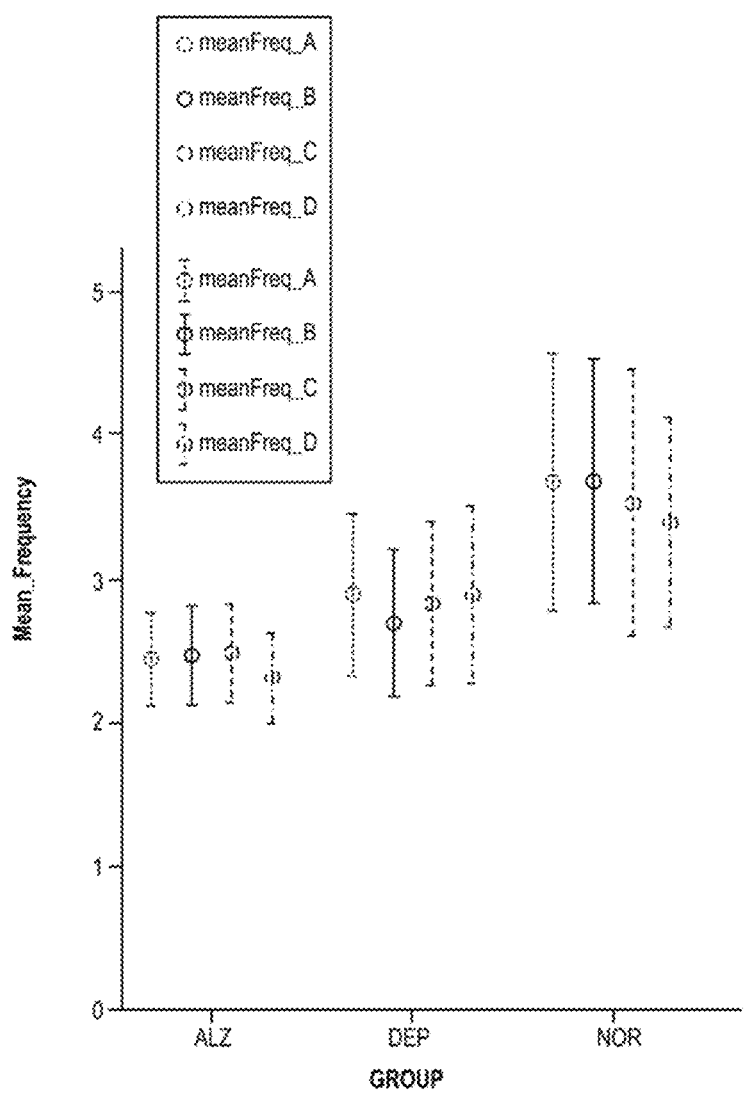
Fig. 15B   Error Bars: 95% CI

Fig. 16A

Pairwise Comparisons

Measure: MEASURE_1

| (I) type_new_2 | (J) type_new_2 | Mean Difference (I-J) | Std. Error | Sig.[b] | 95% Confidence Interval for Difference[b] | |
|---|---|---|---|---|---|---|
| | | | | | Lower Bound | Upper Bound |
| ALZ | DEP | .001 | .002 | .453 | -.002 | .004 |
| | NOR | .004* | .002 | .008 | .001 | .007 |
| DEP | ALZ | -.001 | .002 | .453 | -.004 | .002 |
| | NOR | .003 | .002 | .110 | -.001 | .007 |
| NOR | ALZ | -.004* | .002 | .008 | -.007 | -.001 |
| | DEP | -.003 | .002 | .110 | -.007 | .001 |

Fig. 16B

Pairwise Comparisons

Measure: MEASURE_1

| (I) Group | (J) Group | Mean Difference (I-J) | Std. Error | Sig.[b] | 95% Confidence Interval for Difference[b] | |
|---|---|---|---|---|---|---|
| | | | | | Lower Bound | Upper Bound |
| ALZ | DEP | -.402 | .343 | .243 | -1.079 | .275 |
| | NOR | -1.141* | .349 | .001 | -1.830 | -.452 |
| DEP | ALZ | .402 | .343 | .243 | -.275 | 1.079 |
| | NOR | -.739 | .419 | .079 | -1.566 | .088 |
| NOR | ALZ | 1.141* | .349 | .001 | .452 | 1.830 |
| | DEP | .739 | .419 | .079 | -.088 | 1.566 |

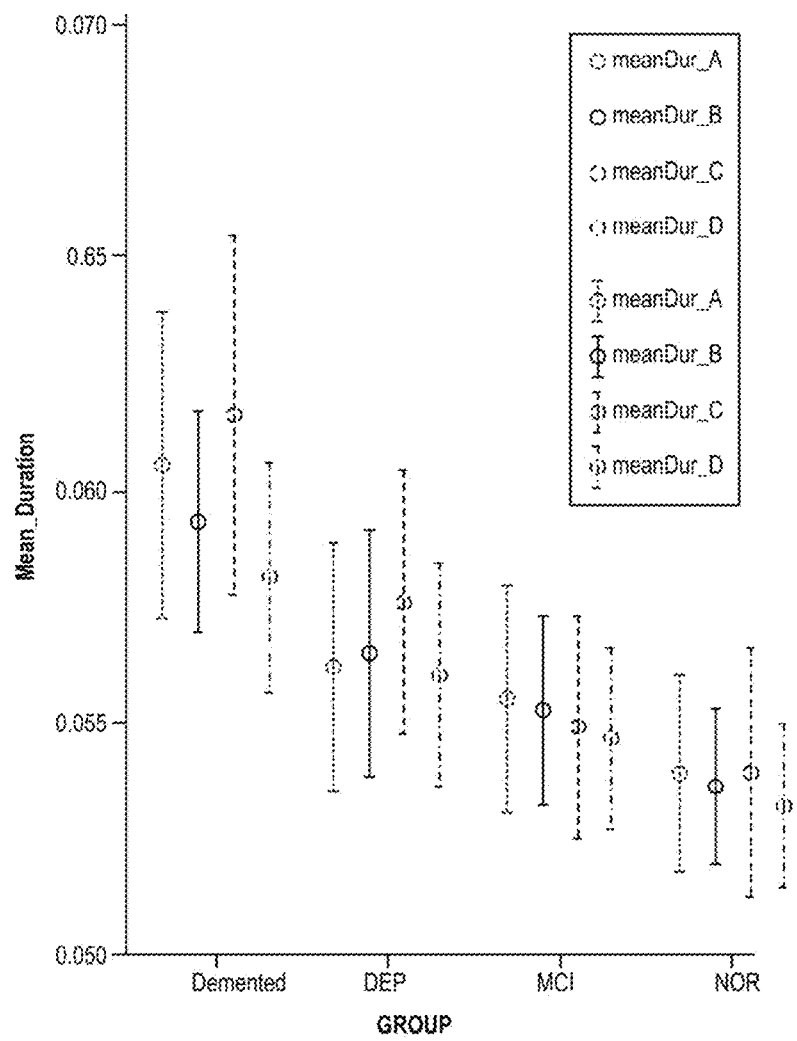
Fig. 17A   Error Bars: 95% CI

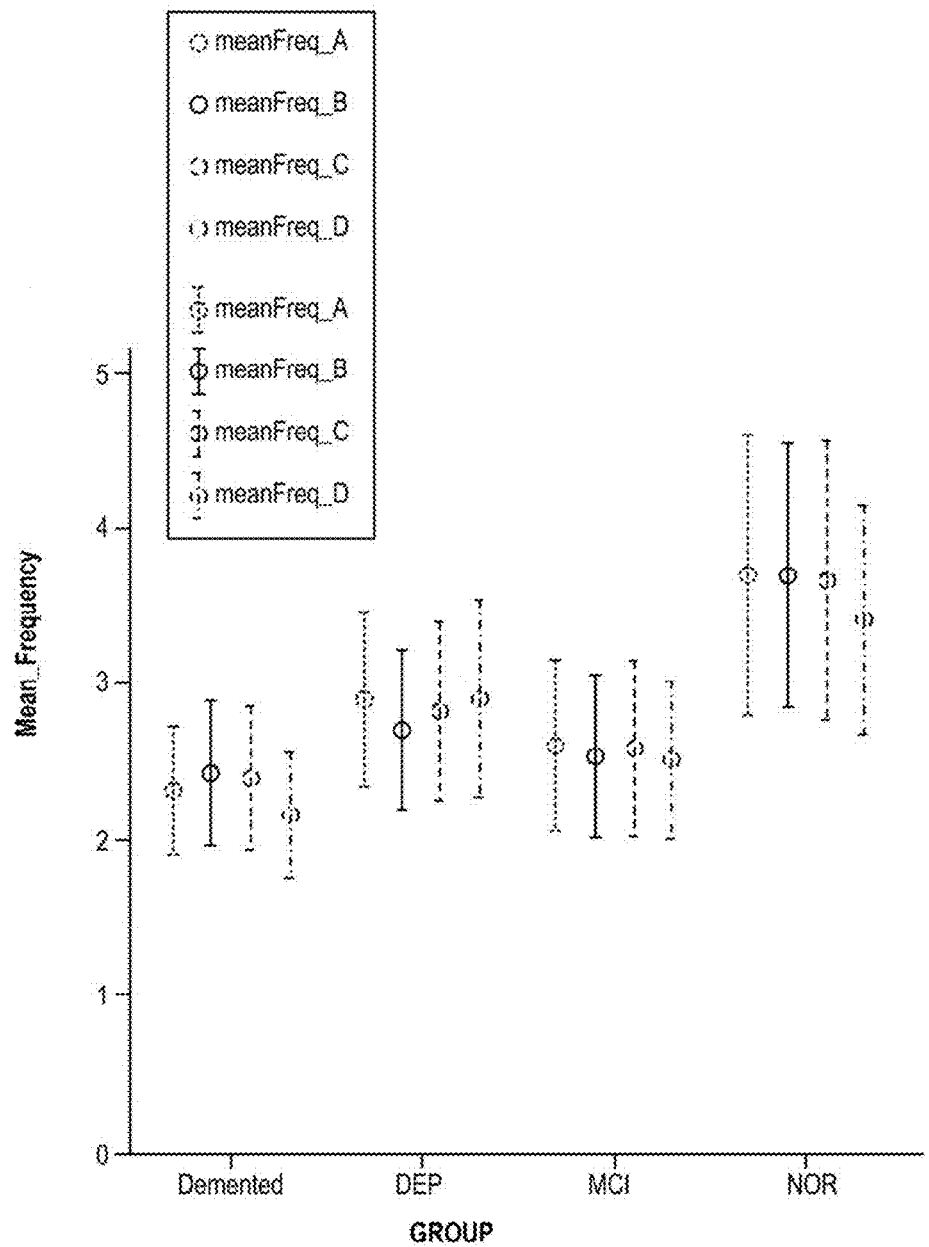
Fig. 17B  Error Bars: 95% CI

Fig. 18A

Pairwise Comparisons

Measure: MEASURE_1

| (I) Group | (J) Group | Mean Difference (I-J) | Std. Error | Sig.[b] | 95% Confidence Interval for Difference[b] Lower Bound | Upper Bound |
|---|---|---|---|---|---|---|
| Demented | DEP | .003* | .002 | .045 | 7.418E-5 | .007 |
|  | MCI | .005* | .002 | .002 | .002 | .008 |
|  | NOR | .006* | .002 | .000 | .003 | .010 |
| DEP | Demented | -.003* | .002 | .045 | -.007 | -7.418E-5 |
|  | MCI | .001 | .002 | .398 | -.002 | .005 |
|  | NOR | .003 | .002 | .103 | -.001 | .007 |
| MCI | Demented | -.005* | .002 | .002 | -.008 | -.002 |
|  | DEP | -.001 | .002 | .398 | -.005 | .002 |
|  | NOR | .002 | .002 | .379 | -.002 | .005 |
| NOR | Demented | -.006* | .002 | .000 | -.010 | -.003 |
|  | DEP | -.003 | .002 | .103 | -.007 | .001 |
|  | MCI | -.002 | .002 | .379 | -.005 | .002 |

Fig. 18B

Pairwise Comparisons

Measure: MEASURE_1

| (I) type_new_3 | (J) type_new_3 | Mean Difference (I-J) | Std. Error | Sig.[b] | 95% Confidence Interval for Difference[b] | |
|---|---|---|---|---|---|---|
| | | | | | Lower Bound | Upper Bound |
| Demented | DEP | -.509 | .381 | .183 | -1.261 | .243 |
| | MCI | -.235 | .360 | .515 | -.944 | .475 |
| | NOR | -1.249* | .387 | .001 | -2.011 | -.486 |
| DEP | Demented | .509 | .381 | .183 | -.243 | 1.261 |
| | MCI | .274 | .395 | .488 | -.505 | 1.054 |
| | NOR | -.739 | .420 | .080 | -1.568 | .089 |
| MCI | Demented | .235 | .360 | .515 | -.475 | .944 |
| | DEP | -.274 | .395 | .488 | -1.054 | .505 |
| | NOR | -1.014* | .401 | .012 | -1.804 | -.224 |
| NOR | Demented | 1.249* | .387 | .001 | .486 | 2.011 |
| | DEP | .739 | .420 | .080 | -.089 | 1.568 |
| | MCI | 1.014* | .401 | .012 | .224 | 1.804 |

EEG MICROSTATES ANALYSIS

RELATED APPLICATIONS

This application is related to PCT Patent Application No. PCT/IB2017/055899, having international date of Sep. 27, 2017, titled "EEG MICROSTATES FOR CONTROLLING NEUROLOGICAL TREATMENT", and further to U.S. Provisional patent application No. 62/652,361 filed on Apr. 4, 2018 titled "EEG MICROSTATES ANALYSIS". The contents of the above applications are all incorporated by reference as if fully set forth in their entirety.

FIELD AND BACKGROUND OF THE INVENTION

The present invention, in some embodiments thereof, relates to measurements of electroencephalography (EEG) microstates and, more particularly, but not exclusively, to measurements of EEG microstates in combination with a neurological treatment.

U.S. Pat. No. 6,983,184 describes a method for modifying a particular electrophysiological feature generated in response to a stimulus.

https://www(dot)alz(dot)org/research/diagnostic_criteria/preclinical_recommendations(dot)pdf discusses staging of Alzheimer's disease and procedure during pre-clinical stages.

EEG analysis is also described in Koenig, T., Prichep, L., Dierks, T., Hubl, D., Wahlund, L. O., John, E. R., Jelic, V., 2005b. Decreased EEG synchronization in Alzheimer's disease and mild cognitive impairment. Neurobiol. Aging 26, 165-171.

Microstate analysis and extraction is described in "Microstates in resting-state EEG: Current status and future directions" in Neuroscience and Biobehavioral Reviews 49 (2015) 105-113 by Arjun Khanna.

Alzheimer markers are described in "Quantitative EEG power and synchronization correlate with Alzheimer's disease CSF biomarkers" by Smailovic et al, in Neurobiology of Aging 63 (2018) 88-95.

SUMMARY OF THE INVENTION

Following are some more examples of some embodiments of the invention, which may be practiced together or separately, including mixing features between examples:

Example 1

A method for generating a risk indication for disease causing reduced cognitive expression:
analyzing EEG data to generate one or more EEG parameter; and
generating a risk for one or both of depression and MCI (mild cognitive impairment) based on said one or more EEG parameters.

Example 2

A method according to example 1, wherein said disease comprises MCI.

Example 3

A method according to example 1, wherein said disease comprises depression.

Example 4

A method according to any of examples 1-3, wherein said one or more EEG parameter comprises a microstate-derived parameter.

Example 5

A method according to example 4, wherein said one or more EEG parameter comprises a microstate duration derived parameter.

Example 6

A method according to example 4 or example 5, wherein said one or more EEG parameter comprises a microstate frequency derived parameter.

Example 7

A method according to any of the preceding examples, wherein said generating a risk comprises distinguishing said disease from one or both of a non-disease state and a demented state.

Example 8

A method according to any of the preceding examples, wherein said generating a risk comprises generating a likelihood of said disease.

Example 9

A method according to any of the preceding examples, wherein said generating a risk comprises generating a severity of said disease.

Example 10

A method according to any of the preceding examples, wherein said generating a risk comprises using a classifier to generate said risk.

Example 11

A method according example 10, wherein said classifier uses data in addition to said EEG data for said generating a risk.

Example 12

A method according to any of the preceding examples, wherein said generating a risk comprises normalizing said at least one parameter based on patient demographics.

Example 13

A method according to any of the preceding examples, wherein said analyzing comprises collecting EEG data for said analysis after a treatment is started and using said analysis for feedback on the treatment.

Example 14

A method according to example 13, wherein said collecting comprises collecting after a treatment session is completed.

Example 15

A method according to example 13, wherein said collecting comprises collecting while a patient is at a clinic or at home for a treatment session.

Example 16

A method according to any of examples 13-15, wherein said collecting comprises collecting within 98 minutes from said starting a treatment.

Example 17

A method according to any of examples 13-15, wherein said collecting comprises collecting within between 1 day and 2 weeks from said starting a treatment.

Example 18

A method according to any of examples 13-17, wherein said feedback is used to decide if to change said treatment to a different type of treatment.

Example 19

A method according to any of examples 13-18, wherein said feedback is used to decide if to change a parameter of said treatment.

Example 20

A method according to any of examples 13-19, wherein said feedback is used to decide if to change a diagnosis of said patient.

Example 21

A method according to any of examples 1-20, comprising treating for depression even if the patient is not positively diagnosed as a depressed patient.

Example 22

A method according to any of examples 1-21, comprising treating for dementia even if the patient is not positively diagnosed as a dementia patient.

Example 23

A method according to any of examples 1-22, comprising collecting EEG data for said analyzing.

Example 24

A method according to example 23, wherein said collecting comprises collecting during an EEG session in which at least 50% of the session is with closed eyes.

Example 25

A method according to example 23 or example 24, comprising performing non-EEG testing on said patient and selecting an amount of EEG data to be collected based on a result of said testing.

Example 26

A method according to example 23 or example 24, comprising selecting a non-EEG testing to be performed on said patient based on a result of said analysis.

Example 27

A method according to example 25 or example 26, comprising diagnosing said patient based also on said non-EEG testing.

Example 28

A method of assessment of a patient with cognitive disfunction, comprising:
(a) collecting and analyzing EEG data about the patient;
(b) administering non-EEG testing to the patient; and
Assessing the patient based on the results of (a) and (b), wherein one or both of (a) and (b) compensate for reduced results provided by the other of (a) and (b).

Example 29

A method according to example 28, comprising collecting less EEG data based on results of said non-EEG testing.

Example 30

A method according to example 28, comprising administering less non-EEG testing based on results of said EEG analyzing.

Example 31

A method according to any of examples 28-30, wherein said assessing comprises assessing for dementia, depression and/or MCI.

Example 32

A method according to any of examples 28-31, wherein said non-EEG testing comprises less than 20 minutes in-person interaction.

Example 33

A method according to any of examples 28-32, wherein said non-EEG testing comprises mostly a questionnaire.

Example 34

A method according to any of examples 28-33, wherein said non-EEG testing takes at most 2 hours.

Example 35

A method according to any of examples 28-35, wherein said EEG collecting takes at most 15 minutes.

Example 36

A method of treating MCI, comprising:
(a) diagnosing a patient as probably suffering from MCI; and
(b) treating the patient as if he was diagnosed with dementia.

Example 37

A method according to example 36, comprising verifying an effect of said treatment by collecting and analyzing EEG data from said patient.

Example 38

A method according to example 36 or example 37, comprising treating said patient if EEG data indicates that the patient has dementia.

Example 39

A method according to any of examples 36-39, comprising confirming a diagnosis of MCI based on said treating improving patient-EEG derived MCI indicating data.

Example 40

A device for calculating a risk indication associated with one or more clinical conditions, comprising:
a memory, wherein the memory stores microstates indications associated with one or more clinical conditions;
control circuitry connected to an input for EEG data, wherein the control circuitry extracts values of at least one microstate parameter from an EEG signal, and calculates a risk indication associated with one or more clinical condition based on the at least one microstates parameters values and the microstates indications stored in the memory.

Example 41

A device according to example 40, wherein the clinical conditions include one or both of MCI and depression.

Example 42

A device according to example 41, wherein the indications are stored in the form of a classifier.

Following are some more examples of some embodiments of the invention:

Example 1

A method for evaluating a treatment for a brain condition, comprising:
extracting one or more microstate parameter values from at least one EEG signal that was measured after the treatment; and
evaluating at least one parameter of the treatment based on the one or more microstate parameter values.

Example 2

The method of example 1, wherein the microstate parameter values represent at least one brain activity state and/or at least one cognitive state.

Example 3

The method of example 1 or 2, further comprising determining if the one or more microstate parameters values are in a desired range of values and/or in a desired relation from at least one indication or value.

Example 4

The method of example 3, wherein the determining further comprises:
comparing the one or more microstates parameters values to at least one desired value and/or an indication of a desired value;
wherein the desired value and/or the indication of a desired value is in the desired range of values.

Example 5

The method of examples 3 or 4, wherein the extracting further comprises extracting one or more microstate parameters values from at least one EEG signal that was measured before the treatment.

Example 6

The method of example 5, wherein the determining further comprises comparing one or more microstate parameters values of an EEG signal that was measured after the treatment, to one or more microstate parameters values of an EEG signal that was measured before the treatment, and determining a change in at least one of the microstate parameters values.

Example 7

The method of example 6, wherein the determining further comprises determining if the change in at least one of the microstate parameters values is a desired change.

Example 8

The method of any of the previous examples, wherein the microstate parameters values represent brain activity related to at least one cognitive domain selected from a list comprising: memory, language, visuospatial ability, attention and/or executive function.

Example 9

The method of example 8, wherein the memory further comprises the ability to learn and/or to recall information.

Example 10

The method of examples 8 or 9, wherein the language further comprises comprehension and/or expression abilities related to language.

Example 11

The method of any one of examples 8 to 10, wherein the visuospatial ability further comprises comprehension and/or effective manipulation of non-verbal and/or graphic and/or geographic information.

Example 12

The method of any one of examples 8 to 11, wherein the executive function further comprises the ability to plan and/or perform abstract reasoning and/or solve problems, and/or focus despite distractions and/or shift focus when appropriate.

Example 13

The method of any one of the previous examples, further comprising:
modifying at least one parameter of the treatment if the one or more microstate parameters values is not a desired value.

Example 14

The method of any one of the previous examples, wherein the microstate parameters comprise resting state microstate parameters, and wherein the EEG signal is measured when an individual is not actively engaged in sensory and/or cognitive processing.

Example 15

The method of any of the previous examples, wherein the brain condition comprises dementia or Attention Deficit Hyperactivity Disorder or Attention Deficit Disorder.

Example 16

The method of example 15, wherein the dementia comprises Alzheimer's disease (AD), Vascular dementia, Dementia with Lewy Bodies (DLB), Mixed dementia, Parkinson's disease related dementia, Frontotemporal dementia, Creutzfeldt-Jakob disease (CJD), Normal pressure hydrocephalus related dementia and/or Huntington's disease related dementia.

Example 17

The method of any of the previous examples, wherein the evaluating further comprises evaluating the efficacy and/or the efficiency of the treatment.

Example 18

The method of example 17, further comprising: delivering a TMS by at least one magnetic coil attached to the scalp, before the extracting.

Example 19

The method of example 18, further comprising: modifying at least one parameter of the TMS based on the efficacy.

Example 20

The method of example 19, wherein the at least one parameter comprises TMS pulse frequency, magnetic field strength, pulse duration, number of pulses per a single train of pulses, number of trains per a treatment session and/or interval time between each the train of pulses.

Example 21

The method of examples 19 or 20, wherein the parameter comprises a location on the scalp for positioning the magnetic coil.

Example 22

The method of any one of examples 18 to 21, wherein the TMS is selectively delivered to one or more brain regions comprising prefrontal cortex, dorsolateral prefrontal cortex, Broca, parietal somatosensory association cortex, ventrolateral prefrontal cortex, inferior frontal gyrus, motor cortex, and/or cerebellum.

Example 23

The method of any one of examples 18 to 22, wherein the TMS comprises repetitive TMS with a frequency of 1-9 Hertz.

Example 24

The method of any one of examples 18 to 23, wherein the TMS is delivered to less than 50% of the brain's volume.

Example 25

The method of any one of examples 3 to 17, further comprising: administering at least one drug to treat the brain condition.

Example 26

The method of example 25, further comprising:
changing a dosage and/or administration timing of the drug based on the determining.

Example 27

The method of examples 25 or 26, further comprising: replacing the at least one drug with a different drug for treating the brain condition after the determining.

Example 28

The method of any of the previous examples, wherein the extracting comprises generating at least two topographic microstate maps and/or the occurrence time of each topographic microstate map.

Example 29

A method for staging a clinical condition based on an EEG signal, comprising:
extracting one or more microstate parameter values from a first EEG signal; and
staging the clinical condition based on at least one microstate parameter value of the extracted microstate parameter values, wherein the microstate parameter values represent at least one brain activity state and/or at least one stage of the clinical condition.

Example 30

The method of example 29, further comprising: selecting a treatment to treat the clinical condition based on the staging.

Example 31

The method of examples 29 or 30, further comprising:
modifying one or more parameters of a treatment protocol for the clinical condition based on the staging.

Example 32

The method of example 31, wherein the parameters of a treatment protocol comprise the intensity of the treatment and/or the duration of the treatment protocol and/or the time interval between at least two consecutive treatment sessions of the treatment protocol.

Example 33

The method of any one of examples 29 to 32, wherein the staging further comprises:
comparing the one or more microstate parameters values to at least one microstate indication which represents at least one cognitive and/or clinical condition.

Example 34

The method of any one of examples 29 to 33, comprising: measuring a second EEG signal after a pre-determined time from the first EEG signal; and
wherein the extracting further comprises extracting one or more microstate parameter values from the second EEG signal.

Example 35

The method of example 34, further comprising:
determining a progression of the clinical condition based on a least one differential indication between one or more microstate parameter values of the second EEG signal and the one or more microstate parameter values of the first EEG signal.

Example 36

The method of example 35, wherein the progression comprises progression from a cognitively normal state to mild cognitive impairment.

Example 37

The method of example 35, wherein the progression comprises progression from mild cognitive impairment to mild Alzheimer's disease.

Example 38

The method of example 35, wherein the progression comprises progression from mild Alzheimer's disease to moderate Alzheimer's disease.

Example 39

The method of any one of examples 29 to 38, wherein the microstate parameters values represent brain activity related to at least one cognitive domain comprising memory, language, visuospatial ability, attention and/or executive function.

Example 40

The method of example 39, wherein the memory further comprises the ability to learn and/or to recall information.

Example 41

The method of examples 39 or 40, wherein the language further comprises comprehension and/or expression abilities related to language.

Example 42

The method of any one of example 39 to 41, wherein the visuospatial ability further comprises comprehension and/or effective manipulation of non-verbal and/or graphic and/or geographic information.

Example 43

The method of any one of examples 39 to 42, wherein the executive function further comprises the ability to plan and/or perform abstract reasoning and/or solve problems, and/or focus despite distractions and/or shift focus when appropriate.

Example 44

The method of any one of examples 29 to 43, wherein the clinical condition comprises Alzheimer's disease, and/or Attention Deficit Hyperactivity Disorder and/or Attention Deficit Disorder.

Example 45

The method of any one of examples 29 to 44 wherein the at least one stage comprises mild cognitive impairment and/or mild Alzheimer's disease.

Example 46

The method of any one of examples 29 to 45, wherein the microstate parameters comprise resting state microstate parameters, and wherein the EEG signal is measured when an individual is not actively engaged in sensory and/or cognitive processing.

Example 47

The method of any one of examples 29 to 46, wherein the microstate parameter values comprise at least two topographic microstate maps and/or the occurrence time of each topographic microstate map.

Example 48

A device for determining a clinical stage of a brain condition, comprising:
a memory, wherein the memory stores microstates indications that reflects at least one stage of the brain condition;
a control circuitry connected to at least one EEG electrode and to the memory, wherein the control circuitry extracts at least one microstates parameters values from an EEG signal, measured by the at least one EEG electrode and determines the stage of the clinical condition based on the at least one microstates parameters values and the microstates indications stored in the memory.

Example 49

The device of example 48, wherein the control circuitry selects a treatment protocol adjusted for treating the stage of a clinical condition; and wherein the memory stores the treatment protocol.

Example 50

The device of examples 48 or 49, wherein the control circuitry modifies at least one parameter of a treatment protocol for the treatment of the clinical condition, to adjust the treatment protocol for treating the stage of the clinical condition; and wherein the memory stores the treatment protocol.

Example 51

The device of examples 49 or 50, further comprising a transmitter; wherein the transmitter transmits the treatment protocol for treating the stage of the clinical condition to a magnetic stimulation device.

Example 52

The device of any one of examples 48 to 51, wherein the brain condition comprises Alzheimer's disease or mild cognitive impairment or Attention Deficit Hyperactivity Disorder or Attention Deficit Disorder.

Example 53

The device of any one of examples 48 to 52, wherein the microstate parameters comprise resting state microstate parameters, and wherein the EEG signal is measured when an individual is not actively engaged in sensory and/or cognitive processing.

Following are some additional examples of some embodiments of the invention:

Example 1

A method for evaluating a treatment for a brain condition, comprising:

extracting one or more microstate parameter values from at least one EEG signal that was measured after the treatment; and evaluating at least one parameter of the treatment based on the one or more microstate parameter values.

Example 2

The method of example 1, wherein the microstate parameter values represent at least one brain activity state and/or at least one cognitive state.

Example 3

The method of examples 1 or 2, further comprising determining if the one or more microstate parameters values is in a desired range of values and/or in a desired relation from at least one indication or value.

Example 4

The method of example 3, wherein the determining further comprises:

comparing the one or more microstates parameters values to at least one desired value and/or an indication of a desired value;

wherein the desired value and/or the indication of a desired value is in the desired range of values.

Example 5

The method of claim 3 or 4, wherein the extracting further comprises extracting one or more microstate parameters values from at least one EEG signal that was measured before the treatment.

Example 6

The method of example 5, wherein the determining further comprises comparing one or more microstate parameters values of an EEG signal that was measured after the treatment, to one or more microstate parameters values of an EEG signal that was measured before the treatment, and determining a change in at least one of the microstate parameters values.

Example 7

The method of example 6, wherein the determining further comprises determining if the change in at least one of the microstate parameters values is a desired change.

Example 8

The method of any of the previous examples, wherein the microstate parameters values represent brain activity related to at least one cognitive domain selected from a list comprising: memory, language, visuospatial ability, attention, abstract thinking, planning and/or executive function.

Example 9

The method of any one of the previous examples, further comprising:

modifying at least one parameter of the treatment if the one or more microstate parameters values is not a desired value.

Example 10

The method of any one of the previous examples, wherein the microstate parameters comprise resting state networks or resting state microstate parameters, and wherein the EEG signal is measured when an individual is not actively engaged in sensory and/or cognitive processing.

Example 11

The method of any of the previous examples, wherein the brain condition comprises Mild cognitive impairment (MCI), dementia or Attention Deficit Hyperactivity Disorder or Attention Deficit Disorder or Depression.

Example 12

The method of example 11, wherein the dementia comprises Alzheimer's disease (AD), Vascular dementia, Dementia with Lewy Bodies (DLB), Mixed dementia, Parkinson's disease related dementia, Frontotemporal dementia, Creutzfeldt-Jakob disease (CJD), Normal pressure hydrocephalus related dementia and/or Huntington's disease related dementia.

Example 13

The method of any of the previous examples, wherein the evaluating further comprises evaluating the efficacy and/or the efficiency of the treatment.

Example 14

The method of example 13, further comprising:
delivering a TMS by at least one magnetic coil attached to the scalp, before the extracting.

Example 15

The method of example 14, further comprising:
modifying at least one parameter of the TMS based on the efficacy.

Example 16

The method of example 15, wherein the at least one parameter comprises TMS pulse frequency, magnetic field strength, pulse duration, number of pulses per a single train of pulses, number of trains per a treatment session and/or interval time between each one of the train of pulses.

Example 17

The method of examples 15 or 16, wherein the parameter comprises a location on the scalp for positioning the magnetic coil.

Example 18

The method of any one of examples 14 to 17, wherein the TMS is selectively delivered to one or more brain regions comprising frontal cortex, insular cortex, prefrontal cortex, dorsolateral prefrontal cortex, Broca, Wernicke, temporal cortex, hippocampi, parietal cortex, cingulate cortex, posterocingulate cortex, occipital cortex, ventrolateral prefrontal cortex, inferior frontal gyrus, sensory cortex, motor cortex, and/or cerebellum.

Example 19

The method of any one of examples 14 to 18, wherein the TMS comprises repetitive TMS with a frequency of 1-9 Hertz.

Example 20

The method of any one of examples 14 to 19, wherein the TMS is delivered to less than 50% of the brain's volume.

Example 21

The method of any one of examples 3 to 13, further comprising: administering at least one drug to treat the brain condition.

Example 22

The method of example 21, further comprising:
changing a dosage and/or administration timing of the drug based on the determining.

Example 23

The method of examples 21 or 22, further comprising:
replacing at least one drug with a different drug for treating the brain condition after the determining.

Example 24

The method of any of the previous examples, wherein the extracting comprises generating at least two topographic microstate maps and/or the occurrence time of each topographic microstate map.

Example 25

A method for generating a risk indication for classifying a subject condition as of one or more clinical conditions based on an EEG signal, comprising:
extracting values of one or more microstate parameters from a first EEG signal recorded from the subject; and
calculating a risk indication of one or more clinical conditions based on the extracted one or more microstate parameter values.

Example 26

The method of example 25, comprising:
analyzing results of one or more cognitive tests performed on the subject, and wherein the calculating comprises calculating a risk indication of the one or more clinical conditions based on the at least one microstate parameter values and the analysis results of the one or more cognitive tests.

Example 27

The method of examples 25 or 26, comprising:
measuring one or more biomarkers in the subject associated with the one or more clinical conditions, and wherein the calculating comprises calculating a risk indication of the one or more clinical conditions based on the at least one microstate parameters values and the measured one or more biomarkers.

Example 28

The method of any one of examples 25 to 27, further comprising:
selecting a treatment to treat the one or more clinical conditions based on the calculated risk indication.

Example 29

The method of any one of examples 25 to 28, further comprising:
modifying one or more parameters of a treatment protocol for the clinical condition based on the risk indication.

Example 30

The method of example 29, wherein the parameters of a treatment protocol comprise the intensity of the treatment and/or the duration of the treatment protocol and/or the time interval between at least two consecutive treatment sessions of the treatment protocol.

Example 31

The method of any one of examples 25 to 30, wherein the calculating further comprises:

comparing the one or more microstate parameters values to at least one microstates value indication or a range of microstates value indications which represents at least one cognitive and/or clinical condition.

Example 32

The method of any one of examples 25 to 31, comprising:

recording a second EEG signal after a pre-determined time from the first EEG signal; and wherein the extracting further comprises extracting one or more microstate parameter values from the second EEG signal.

Example 33

The method of example 32, comprising:

updating the risk indication based on the one or more microstate parameter values of the second EEG signal.

Example 34

The method of example 33, comprising determining a progression of the one or more clinical conditions based on the updated risk indication.

Example 35

The method of example 34, wherein the progression comprises progression from a cognitively normal state to mild cognitive impairment.

Example 36

The method of example 34, wherein the progression comprises progression from mild cognitive impairment to mild Alzheimer's disease dementia.

Example 37

The method of example 34, wherein the progression comprises progression from mild Alzheimer's disease dementia to moderate Alzheimer's disease dementia.

Example 38

The method of any one of examples 25 to 37, wherein the clinical conditions comprise Alzheimer's disease, and/or Attention Deficit Hyperactivity Disorder and/or Attention Deficit Disorder and/or Depression and/or vascular dementia and/or mild cognitive impairment and/or normal cognition.

Example 39

The method of any one of examples 25 to 38, wherein the microstate parameters comprise resting state networks or resting state microstate parameters, and wherein the EEG signal is measured when an individual is not actively engaged in sensory and/or cognitive processing.

Example 40

The method of any one of examples 25 to 39, wherein the microstate parameters comprise duration or mean duration of one or more microstates.

Example 41

The method of any one of examples 25 to 40, wherein the microstates parameters comprise occurrence, frequency and/or number of transitions of one or more microstates.

Example 42

A device for calculating a risk indication associated with one or more clinical conditions, comprising:

a memory, wherein the memory stores microstates indications associated with one or more clinical conditions;

a control circuitry connected to at least one EEG electrode and to the memory, wherein the control circuitry extracts values of at least one microstate parameter from an EEG signal, measured by the at least one EEG electrode and calculates a risk indication associated with one or more clinical condition based on the at least one microstates parameters values and the microstates indications stored in the memory.

Example 43

The device of example 42, wherein the control circuitry selects a treatment protocol adjusted for treating the stage of a clinical condition; and wherein the memory stores the treatment protocol.

Example 44

The device of examples 42 or 43, wherein the control circuitry modifies at least one parameter of a treatment protocol for the treatment of the clinical condition, to adjust the treatment protocol for treating the stage of the clinical condition; and wherein the memory stores the treatment protocol.

Example 45

The device of examples 43 or 44, further comprising a transmitter; wherein the transmitter transmits the treatment protocol for treating the stage of the clinical condition to a magnetic stimulation device.

Example 46

The device of any one of examples 42 to 45, wherein the brain condition comprises Alzheimer's disease or mild cognitive impairment or Attention Deficit Hyperactivity Disorder or Attention Deficit Disorder.

Example 47

The device of any one of examples 42 to 46, wherein the microstate parameters comprise resting state networks, and wherein the EEG signal is measured when an individual is not actively engaged in sensory and/or cognitive processing.

Example 48

The device of any one of examples 42 to 47, wherein the at least one microstate parameter comprises duration or mean duration of one or more microstates.

Example 49

The device of any one of examples 42 to 48, wherein the at least one microstate parameter comprises occurrence, frequency and/or number of transitions of one or more microstates.

Example 50

The device of any one of examples 42 to 49, wherein the memory stores results of a cognitive analysis and/or a psychiatric analysis, and wherein the control circuitry calculates the risk indication based on the values of the at least one microstates parameter and based on the cognitive analysis results and/or the psychiatric analysis results.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as extracting microstate parameters values from an EEG signal, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A is a general flow chart of a process for generating an indication based on microstate parameters values, according to some embodiments of the invention;

FIG. 1B is a general flow chart of a microstate parameters values extraction process, according to some embodiment of the invention;

FIG. 2 is a flow chart of a treatment effect analysis process based on microstate parameters values, according to some embodiments of the invention;

FIG. 3 is a flow chart of a drug effect analysis process based on microstate parameters values, according to some embodiments of the invention;

FIG. 4A is a block diagram of a device for EEG measurement and microstate parameters values extraction, combined with a device for electric/magnetic field application to a brain, according to some embodiments of the invention;

FIG. 4B is a block diagram of a device for EEG measurements, microstate parameters values extraction and for application of electric/magnetic field to a brain, according to some embodiments of the invention;

FIG. 5A is a flow chart of a TMS effect analysis process based on microstates parameter, according to some embodiments of the invention;

FIG. 5B is a flow chart of a process for generating a risk indicator associated with one or more clinical conditions, according to some embodiments of the invention;

FIG. 6A is a table summarizing the number of participants for each cohort divided to age groups in a validation experiment, according to some embodiments of the invention;

FIG. 6B is a flow chart of a general process for extracting and analyzing microstates, according to some embodiments of the invention;

FIG. 7 is a flow chart of a process for extraction of EEG quiet segments, according to some embodiments of the invention;

Figure 8:
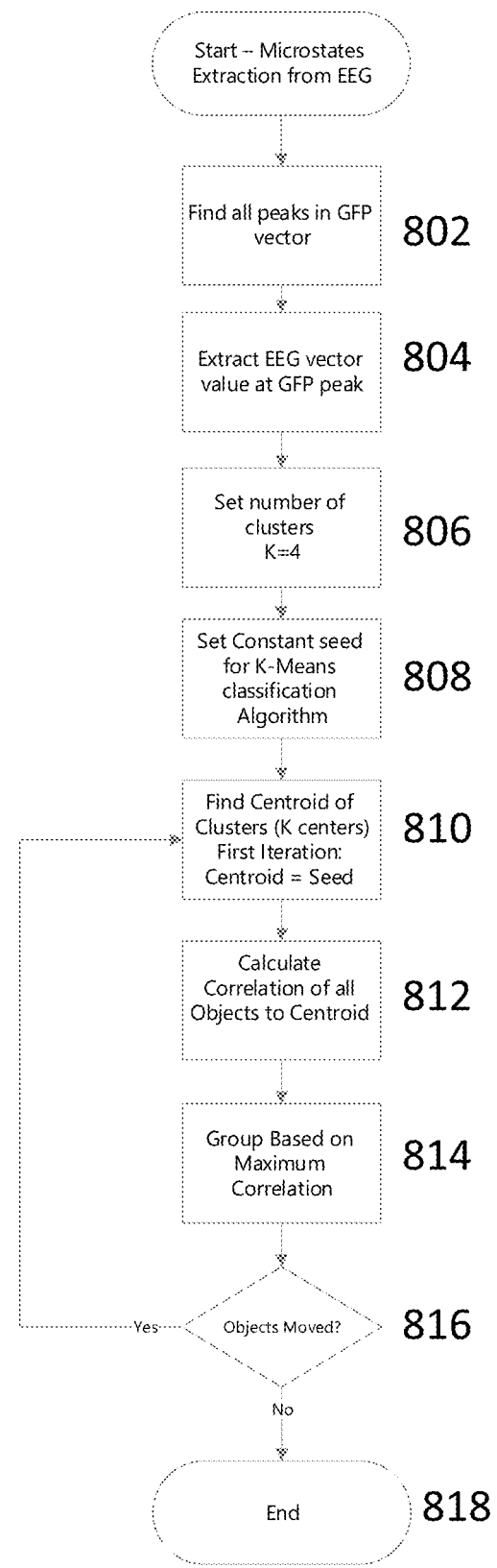
Figure 9:
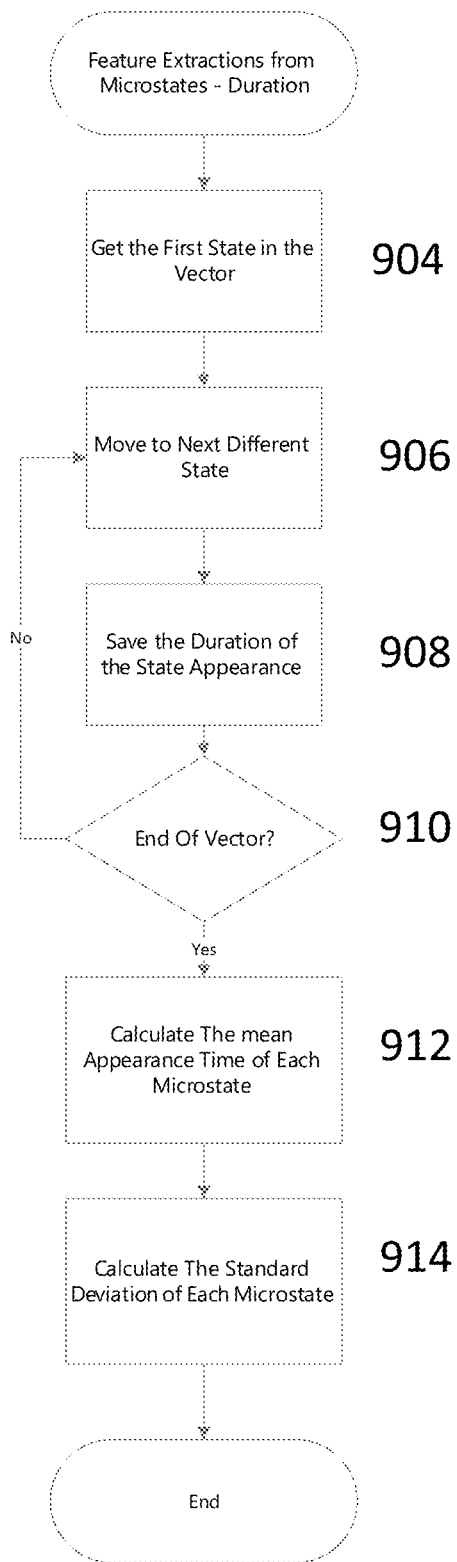
Figure 10:
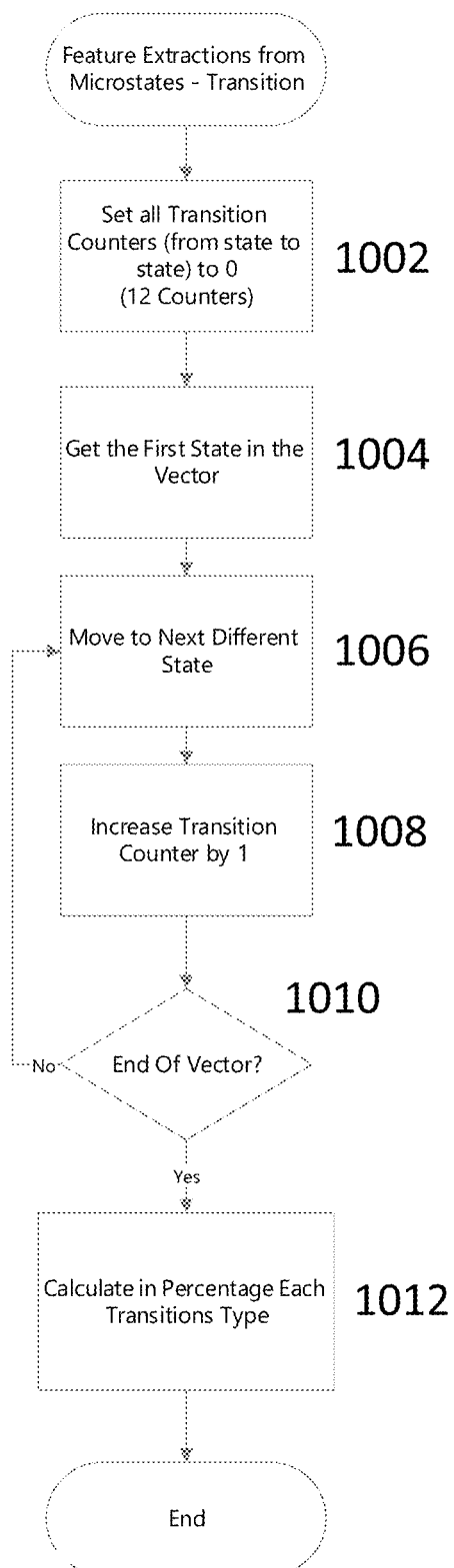
Figure 11:
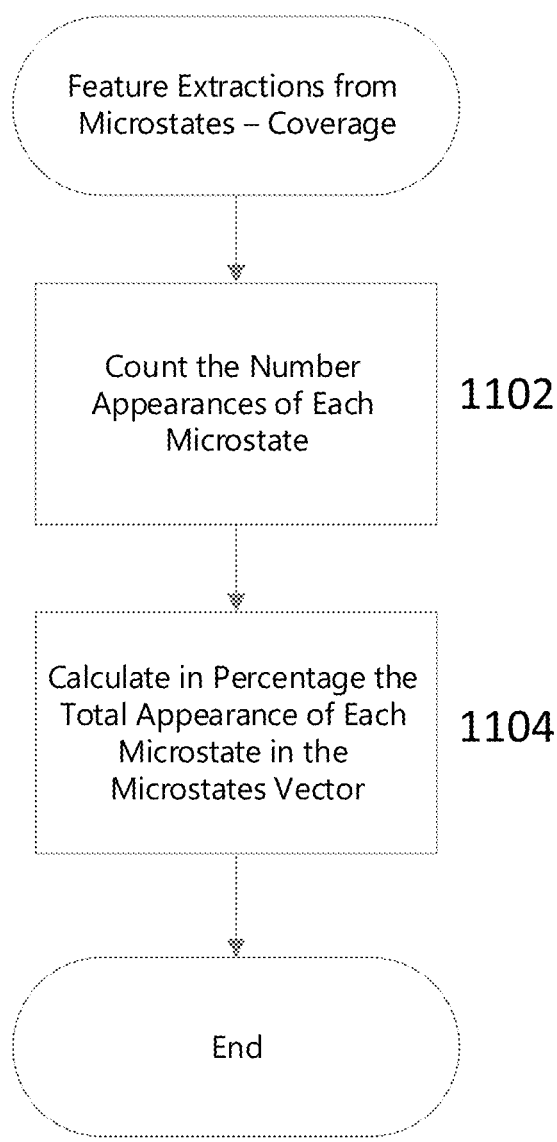
Figure 12:
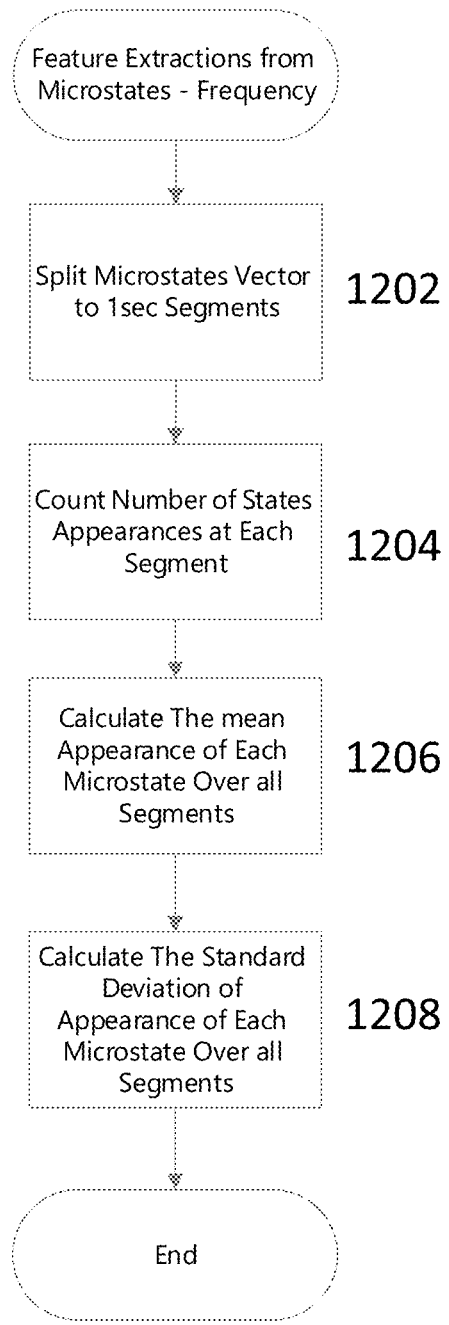
Figure 14:
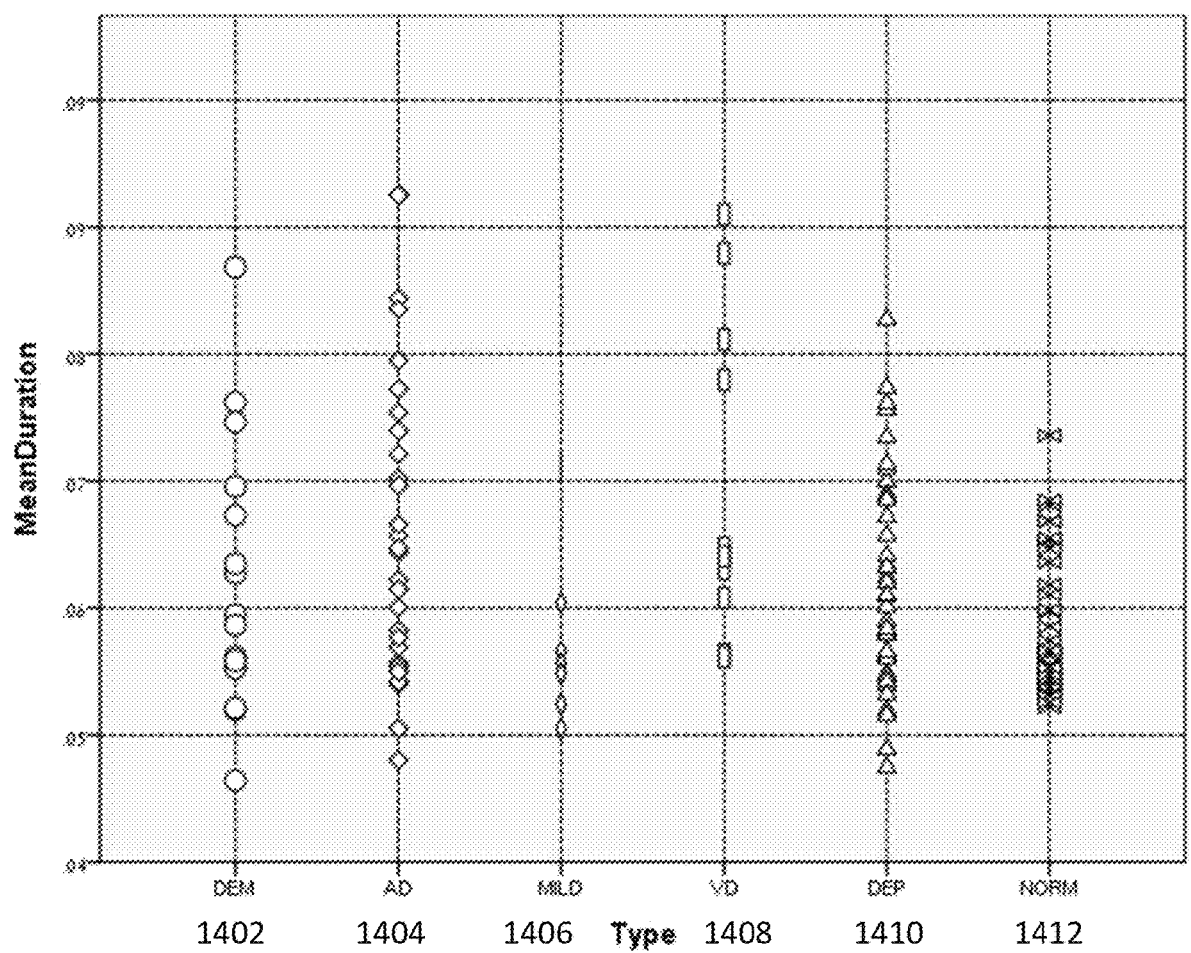
Figure 19:
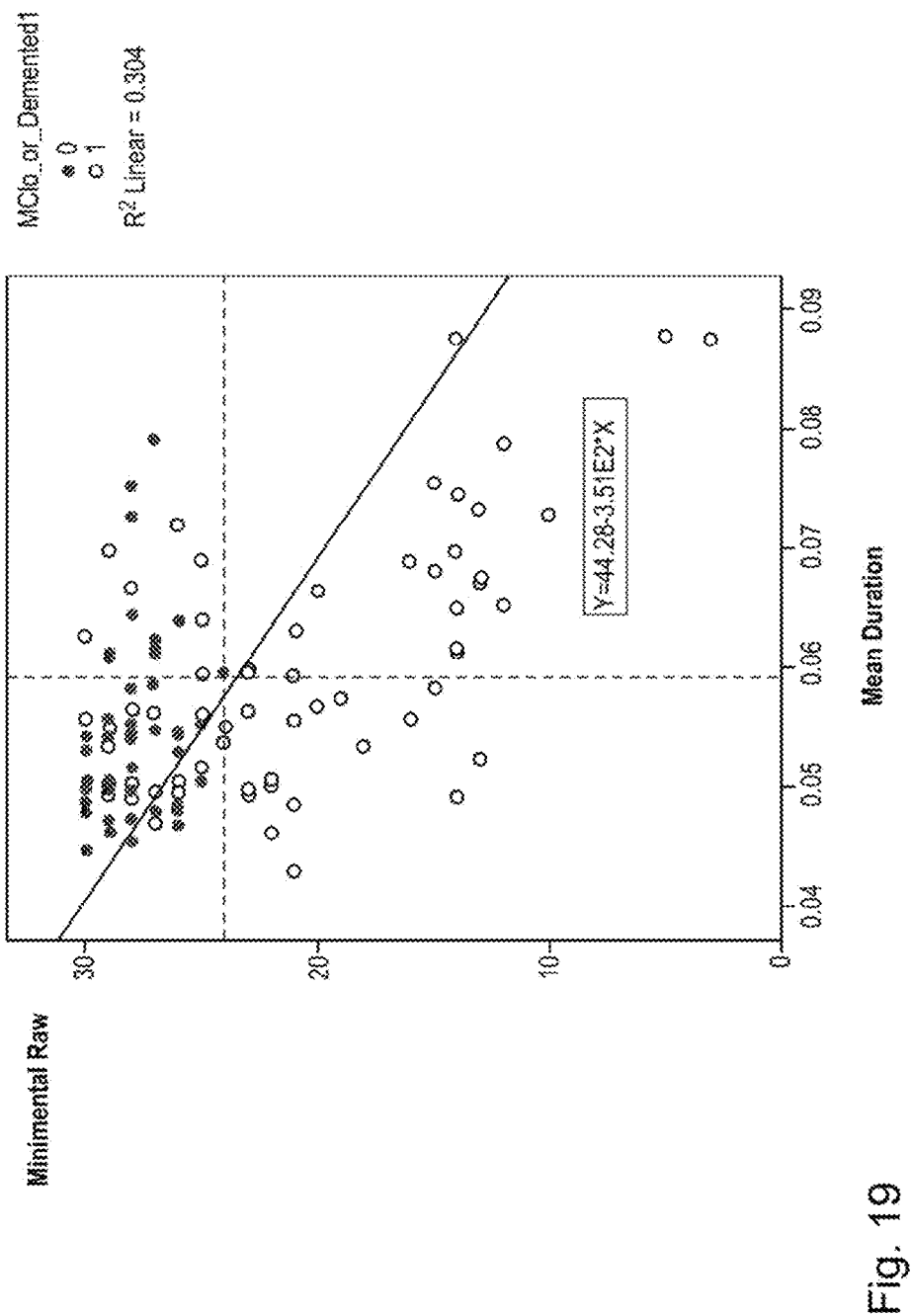
Figure 20:
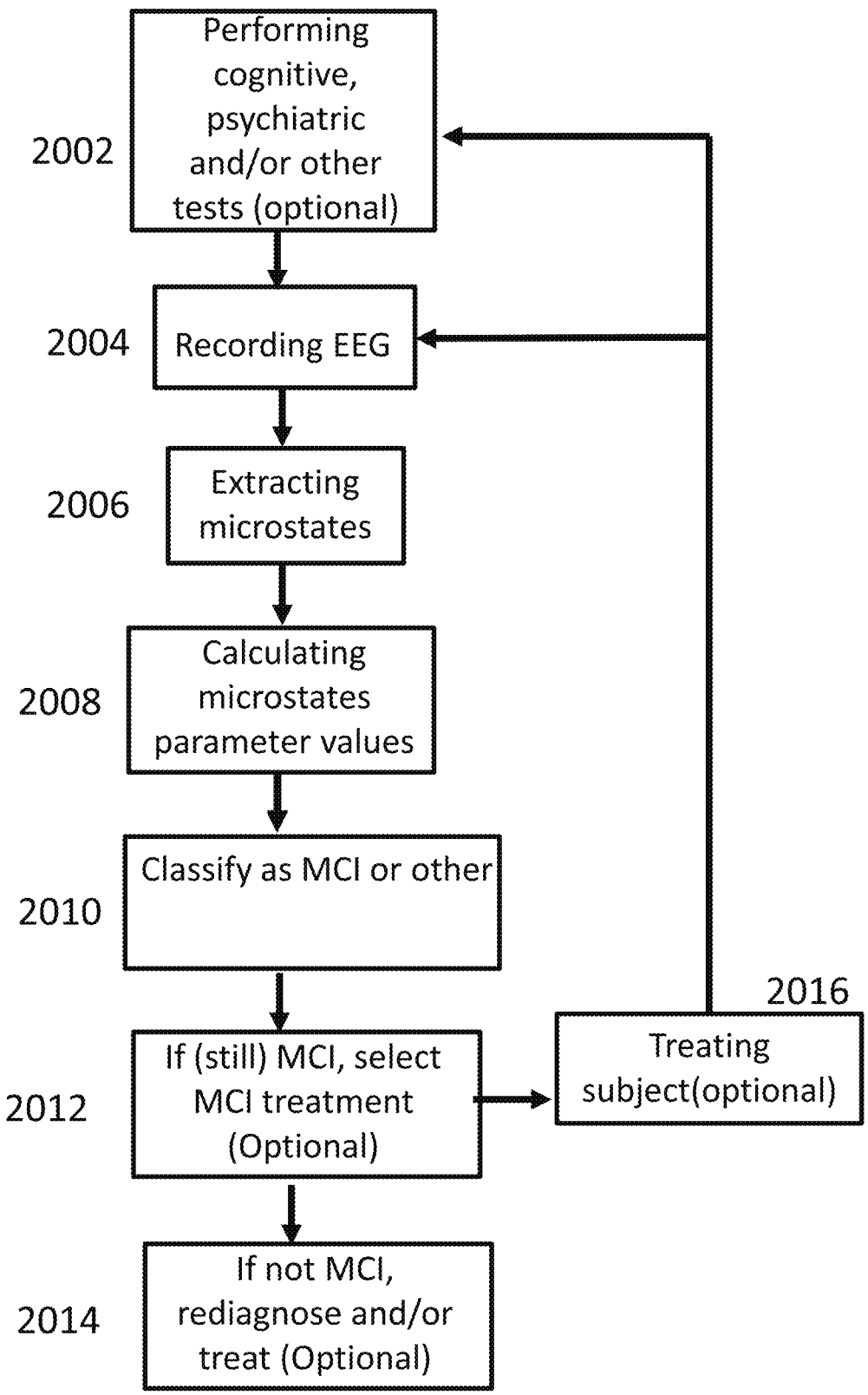
Figure 21:
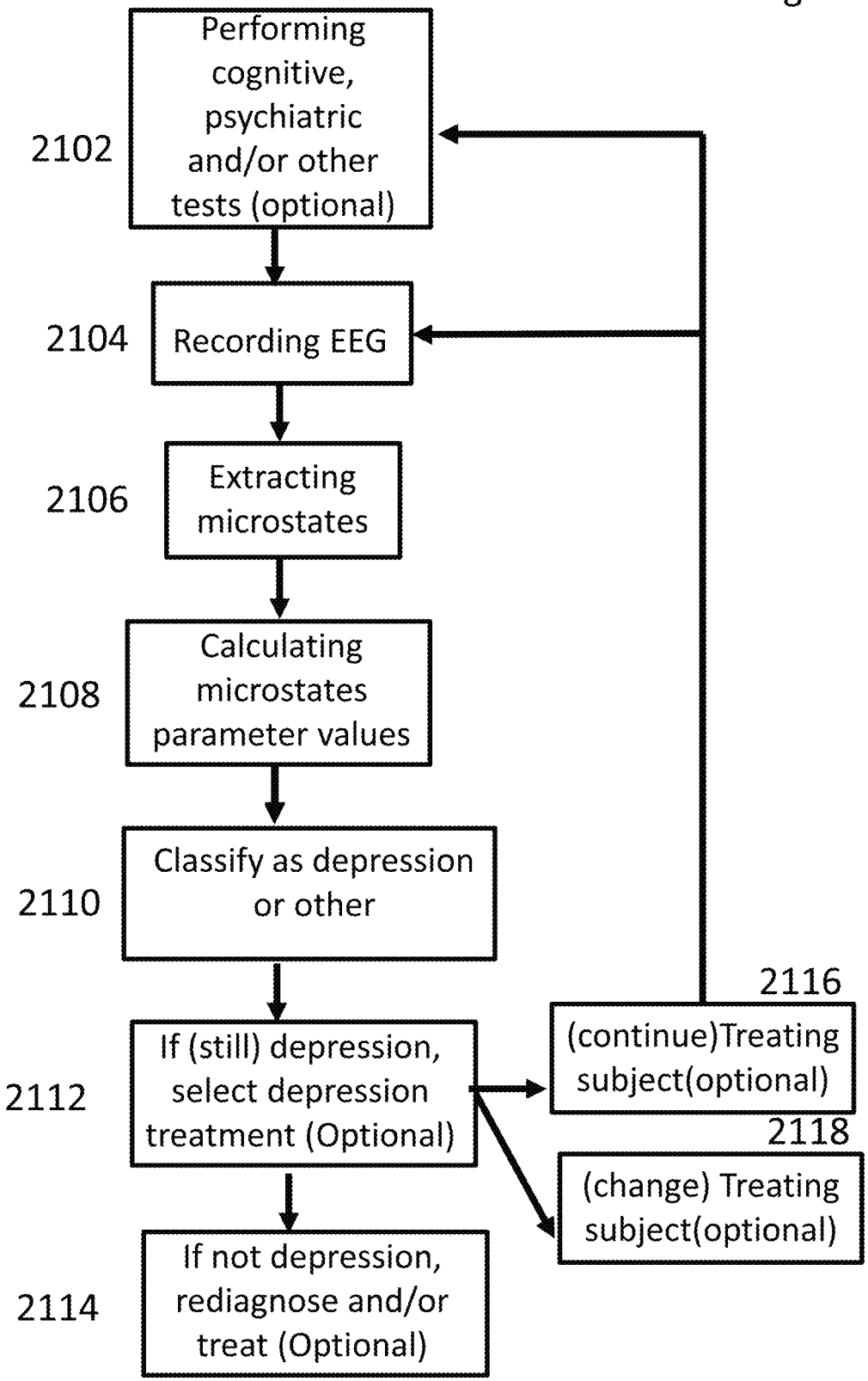

FIG. 8 is a flow chart of a process for extraction of microstates from an EEG signal, according to some embodiments of the invention;

FIG. 9 is a flow chart of a process for calculating duration of one or more microstates, according to some embodiments of the invention;

FIG. 10 is a flow chart of a process for calculating transitions of one or more microstates, according to some embodiments of the invention;

FIG. 11 is a flow chart of a process for calculating coverage of one or more microstates, according to some embodiments of the invention;

FIG. 12 is a flow chart of a process for calculating frequency of one or more microstates, according to some embodiments of the invention;

FIG. 13 is a table summarizing differences in microstates duration between different populations in the validation experiment, according to some embodiments of the invention;

FIG. 14 is a scatter plot of the mean microstates duration per each subject in each group, according to some embodiments of the invention;

FIG. 15A is a chart showing the differences in mean duration of different types of microstates, for various cognitive disease states, in accordance with exemplary embodiments of the invention;

FIG. 15B is a chart showing the differences in mean frequency of different types of microstates, for various cognitive disease states, in accordance with exemplary embodiments of the invention;

FIG. 16A is a table showing pairwise comparisons for mean duration between the groups of patients with the different cognitive disease states, indicating statistical significance, in accordance with some embodiments of the invention;

FIG. 16B is a table showing pairwise comparisons for mean frequency between the groups of patients with the different cognitive disease states, indicating statistical significance, in accordance with some embodiments of the invention;

FIG. 17A is a chart showing the differences in mean duration of different types of microstates, for various cognitive disease states, including mild cognitive impairment (MCI), in accordance with exemplary embodiments of the invention;

FIG. 17B is a chart showing the differences in mean frequency of different types of microstates, for various cognitive disease states, including mild cognitive impairment (MCI), in accordance with exemplary embodiments of the invention;

FIG. 18A is a table showing pairwise comparisons for mean duration between the groups of patients with the different cognitive disease states including MCI, indicating statistical significance, in accordance with some embodiments of the invention;

FIG. 18B is a table showing pairwise comparisons for mean frequency between the groups of patients with the different cognitive disease states including MCI, indicating statistical significance, in accordance with some embodiments of the invention;

FIG. 19 is a chart showing a relationship between cognitive tests and cognitive assessment using microstates, in accordance with some embodiments of the invention;

FIG. 20 is a flowchart of a method of diagnosing and optionally treating MCI, in accordance with some embodiments of the invention; and FIG. 21 is a flowchart of a method of diagnosing and optionally treating depression, in accordance with some embodiments of the invention.

DESCRIPTION OF SPECIFIC EMBODIMENTS OF THE INVENTION

The present invention, in some embodiments thereof, relates to measurements of EEG microstates and, more particularly, but not exclusively, to measurements of EEG microstates in combination with a neurological treatment.

A broad aspect of some embodiments of the invention relates to identifying and/or treating MCI (mild cognitive impairment), in which a patient and/or a partner and/or other persons with regular contact with the patient sense a decline in cognitive function, but typical daily activities of the patient are not substantially harmed by such decline. In some exemplary embodiments of the invention, the identifying comprises identifying using an objective clinical test.

An aspect of some embodiments of the invention relates to an objective clinical test for MCI, in which EEG signals are analyzed to help assess a patient's state. Optionally, the EEG signals are analyzed to identify one or more microstate parameter values and the values processed to assist in diagnosing MCI. In some exemplary embodiments of the invention, the values include microstates frequencies and durations. In some exemplary embodiments of the invention, diagnosing comprises differentiating MCI from dementia. In some exemplary embodiments of the invention, diagnosing comprises differentiating MCI from non-dementia patients and/or from depressive patients.

In some exemplary embodiments of the invention, the analysis of EEG is used together with other data, such as patient age and/or performance in one or more cognitive test and/or expert assessment.

In some exemplary embodiments of the invention, the objective test does not require an observer. In some exemplary embodiments of the invention, the objective test is non-participatory other than the patient not engaging in any activity, e.g., being in a rest state.

In some exemplary embodiments of the invention, the objective test is non-cognitive in that the patient does not perform any specific cognitive activities, especially not activities with a performance outcome which depends on general or specific cognitive ability.

An aspect of some embodiments of the invention relates to treating MCI. In some exemplary embodiments of the invention, MCI is suspected to be a precursor of clinically recognizable Alzheimer's disease and treatment is started at a mild cognitive impairment stage, rather than later. In some exemplary embodiments of the invention, any treatment used for Alzheimer's disease may be used, optionally at a normal or possibly a reduced dose. In some exemplary embodiments of the invention, the effect of treatment is used to assess if the treatment is suitable and/or if the MCI is an Alzheimer's disease pre-stage.

In some exemplary embodiments of the invention, the following assumptions are made: Alzheimer disease (ALZ) often starts 1-2 decades before clinical signs and progresses in what may be divide dup into stages (though progress is probably continuous). At a pre-clinical ALZ stage, pathological changes may occur in the brain but there cognitive evaluation is normal. At an MCI stage, cognitive evaluation is abnormal but daily activities are normal. At a dementia (DEM) stage, also daily activities are abnormal In some exemplary embodiments of the invention, effect of treatment is assessed, for example, by an improvement or lack of degradation or a reduced degradation in patient state, for example, as indicated using cognitive tests and/or EEG analysis.

In some exemplary embodiments of the invention, if MCI is suspected, but microstate data indicates dementia then dementia-appropriate treatment (e.g., drugs) may be used even though no MCI-specific drug treatment is approved (by FDA).

If TMS or TCDC (trans-cranial DC stimulation) is used, an evaluation of the treatment effect on microstate parameters is optionally sued to guide treatment. For example, if the microstate data shows improvement, the treatment is continued. Otherwise, one or more treatment parameter is changed. In some cases, lack of treatment effect is used as a diagnostic indicator and the patient may be rediagnosed, for example, using more detailed, lengthy and/or expensive tests.

For patients with depression (DEP), treatment may be, for example with TMS, or TCDC, in which case changes in microstate data may be used as an indicator that the treatment is correct and/or parameters thereof need to be changed. Similarly, drug treatment may be assessed/changed based on its effect on microstate parameters.

In general, microstate parameters may be used to assess the effect of treatment before clinical signs are easily discernible and thus potentially allow the treatment to serve as a diagnostic test and/or be modified sooner.

An aspect of some embodiments of the invention relates to diagnosis of depression using EEG analysis. In some exemplary embodiments of the invention, EEG microstate parameters are used to distinguish a depressed patient from a cognitively normal patient and/or a patient with dementia and/or subjects without depression. A potential advantage of using microstates is that the test is more objective than psychiatric evaluation. Another potential advantage is that assessment can be done by machine. Another potential advantage is the speed of assessment.

In some exemplary embodiments of the invention, a depression score is calculated for the patient, for example, based on a probability and/or severity of depression which may be a mapping between abnormal microstate values and disease state. For example, an arbitrary (linear, for example) scale may be used to map the range between NOR microstate vales and the most extreme microstate values associated with DEP, or the scale may reflect the distance from the centroid of the microstate values (e.g., in a space spanned by all the microstate parameters used, with the centroid indicating the center of a cluster of values that indicate depression). Other diseases may have their own centroid value and may also be scored in a similar way. In another example, a table is provided associating microstate values with a depression score, for example, as generate by a human or using machine learning techniques which correlate EEG tests data with psychiatric evaluation.

In some exemplary embodiments of the invention, the score is calculated repeatedly, for example, more often than once a week, one a day, once an hour or at intermediate intervals (which need not be fixed). Optionally, this allows tracking the depressive state of a patient over time, optionally detecting triggers for improvement or degradation in the patient state. Optionally or alternatively, this allows to track the effect of medication or other treatment, optionally indicating a need to change or maintain a medication and/or a dose thereof and/or of a different treatment.

In some exemplary embodiments of the invention, assessment of depression (or other mental state using EEG analysis) is from an implant, for example, from a vagal nerve or deep brain stimulator, optionally using dedicated electrodes, For example, surface electrodes implanted with the stimulation electrode or using sensing electrodes mounted on the stimulation lead. Optionally or alternatively, dedicated sensing electrodes are implanted, possibly on the surface, but at locations other than the insertion location of the stimulation lead or along its path of insertion.

In some exemplary embodiments of the invention, microstate data, with or without additional data is used to diagnose a patient with apparent reduced cognitive ability. In some exemplary embodiments of the invention, MCI is differentiated from NOR using mean frequency data of microstates. Optionally or alternatively, ALZ is differentiated from NOR. Optionally or alternatively, DEP are differentiated form NOR.

In some exemplary embodiments of the invention, the microstate data is normalized using age related tables, for example, as known in the art, for example, as discussed in "Millisecond by Millisecond, Year by Year: Normative EEG Microstates and Developmental Stages", by Koeing et al, NeuroImage Volume 16, Issue 1, May 2002, Pages 41-48.

An aspect of some embodiments of the invention relates to a method of acquiring microstate data, in which an EEG protocol is truncated in time and/or content. In some exemplary embodiments of the invention, the EEG protocol is made shorter. In some exemplary embodiments of the invention, the EEG protocol is made shorter (e.g., by a factor of 1.4, 2, 2.5, 3 or smaller, intermediate or larger factors as compared to a standard test time, by collecting mainly or only data with the eyes closed, for example, a patient may have his eyes closed for 80% or more of the EEG testing time and that time be, for example, 10 minutes, 8 minutes, 6 minutes, 5 minutes, 3 minutes or intermediate and/or shorter times. Optionally or alternatively, the EEG protocol includes only a resting state EEG. Optionally, the protocol is made shorter by collecting relative microstate data, in which at most 300%, 200%, 150% or intermediate percentages of the data needed for extracting microstate parameter values is acquired. Optionally, the microstate data is analyzed by comparison to previously acquired microstate data.

In some exemplary embodiments of the invention, EEG data collection for microstate data comprises collecting data over several minutes, for example, between 2 and 30 minutes, for example, between 6 and 20 minutes, for example, about 10 minutes, optionally with eyes closed and optionally hearing subdued (e.g., ear covers or plugs). In some exemplary embodiments of the invention, EEG collection is ongoing, for example, using a worn EEG system and/or implanted electrodes, and EEG section with suitable data selected form the available EEG data, for example, for microstate extraction.

An aspect of some embodiments of the invention relates to combining microstate data with cognitive and/or other test results, in which tests are selected based on the test being suitable to distinguish between disease states which are not distinguishable using microstate data (e.g., available data, acquirable data and/or data processed using methods as described herein) and/or test results which can be combined with microstate data to increase their reliability and/or diagnostic power.

In some exemplary embodiments of the invention, data from microstate analysis is combined with data from cognitive and/or other tests, so as to provide a significant result, for example, if each type of data on its own is not as significant as desired.

In some exemplary embodiments of the invention, a test (e.g., EEG, cognitive and/or other) is selected based on a lack of distinction provided by other available data. This may allow fewer tests, for example, 90%, 70%, 50%, 30% or intermediate or fewer percentage of cognitive or interactive tests to be used than is standard for assessment.

For example, a typical cognitive assessment may last many hours, such as 4-5 or even 10. In some exemplary embodiments of the invention, using microstate data to generate a potential diagnosis, allows fewer tests to be used. for example, if microstate data indicate possible DEM, fewer cognitive tests may be used, such as mini-mental and one or more memory tests (e.g., word list), which may shorten the cognitive testing time to less than an hour, for example, 20-30 minutes or even less.

Similar tests may be selected if MCI is suspected (e.g., same as dementia, but an additional test in which score is expect to be higher if patient has MCI rather than DEM.

For depression, DEP indicating microstate data may be used together with a depression questionnaire (e.g., BDI) may be used to replace a 40-60 minute evaluation talk.

In some exemplary embodiments of the invention, evaluation for methods as described herein is manual (e.g., using tables to assess microstate data, optionally different tables for different ages). Alternatively, computer processing may be used. In one example, a computer may include tables based on the mean frequency and mean duration data, associated with different diagnoses. In another example, the computer may include different tables for different demographics, for example, ages. In another example, additional patient and/or test data may be used and/or more complex classifiers based on microstate data. For example, a classifier may be trained (e.g., using machine learning techniques, possibly as a neural network), using data such as duration, frequency and percentage statistics, for one or more microstates. Such classifier may also be trained using additional patient data, such as test results. Optionally, the classifier includes an association between potential diagnosis and recommended non-EEG tests to use for further assessment. Optionally or alternatively, the classifier uses previous EEG data form a patient to generate an indication of a change in patient status. Optionally or alternatively, the classifier includes an association between diagnosis and proposed treatment and/or expected results of such treatment. In some cases a classifier is implemented as code, as a model with parameters and/or as a set of tables. In some cases multiple classifiers are used, for example, one for each disease state being tested for.

In some cases, EEG analysis other than microstate analysis is used, for example, GFS, as described in "Decreased EEG synchronization" by Koenig et al.

Such circuitry may be located on a local computer, including, for example, a cellular telephone, table or other mobile device. Optionally or alternatively, the processing is at a remote location, for example a dedicated server or as a cloud service.

An aspect of some embodiments relates to staging a clinical condition based on microstate parameters values extracted from EEG measurements. In some embodiments, the clinical condition stage is determined based on microstate parameters values and at least one additional clinical parameter, for example cognitive tests results and/or behavioral test results and/or imaging test results and/or laboratory test results. Alternatively, the clinical condition stage is based on analysis of at least two sets of microstate parameters values that are measured over a period of time.

In some embodiments the microstate parameters values are extracted after measuring at least one clinical parameter. In some embodiments, the microstate parameter values are compared to microstate indications which correlate with at least one clinical stage or a disease stage. Alternatively, the microstates indications correlate with at least one cognitive state. In some embodiments, a stage of a clinical condition comprises at least one cognitive state. In some embodiments, the clinical stage of a neurological disease, for example, mild or moderate or severe Dementia is determined based on the results of at least one cognitive evaluation or a combination between a cognitive evaluation and microstates parameter values which correlate with the clinical stage. In some embodiments, the stored microstates parameter values or microstates indications correlate with at least one neurological disease, for example Mild Cognitive Impairment (MCI), dementia, or a stage of a neurological disease, for example Alzheimer's disease (AD), Vascular dementia, Dementia with Lewy Bodies (DLB), Mixed dementia, Parkinson's disease related dementia, Frontotemporal dementia, Creutzfeldt-Jakob disease (CJD), Normal pressure hydrocephalus related dementia, Huntington's disease related dementia, Wernicke-Korsakoff Syndrome, Attention Deficit Hyperactivity Disorder (ADHD), Attention Deficit Disorder (ADD) or depression. Optionally, the extracted microstates parameter values correlate with at least one stage of the neurological disease or with at least one cognitive state, for example cognitive impairment related to the neurological disease. In some embodiments, a potential advantage of the extracted microstate parameter values is that they allow early detection of a neurological disease and/or high-resolution monitoring of disease progression. Optionally, the extracted microstate parameters are combined with at least one clinical parameter and/or a cognitive parameter and/or a behavioral parameter, for example to generate a combined score. In some embodiments, the combined score correlates with one or more clinical states, cognitive states or stages of a disease.

In some embodiments, microstate parameters values of a patient that was diagnosed with a neurological condition, for example with mild cognitive impairment (MCI) are measured. In some embodiments, the microstate parameters values are compared to stored indications which correlate with at least one clinical condition and/or with a cognitive state related to the clinical condition, for example to monitor the progression from MCI to AD. Alternatively, microstate parameters values of a patient suffering from at least one neurological and/or cognitive symptom are measured and compared to stored indications which correlate with at least one clinical condition or with a cognitive state related to the clinical condition or with a stage of a neurological disease, for example to determine the clinical condition of the patient or the current disease stage. Optionally, microstates parameter values, for example resting state microstates parameter values are extracted from a measured EEG signal of an individual, to diagnose MCI or very mild AD or mild AD or other types of dementia. In some embodiments, the microstates parameters values are extracted from a measured EEG signal of an individual, for example to diagnose ADHD or ADD, to characterize the severity of ADHD or ADD and/or to monitor the progression of ADHD or ADD.

In some embodiments, to characterize and/or to monitor the progression of AD, MCI, ADD or ADHD microstates parameters values are combined with results of cognitive evaluations and/or behavioral evaluations and/or reports from at least one caregiver.

In some embodiments, microstates are discrete spatiotemporal representations of brain activity. In some embodiments, microstate parameters values represent brain activity related to at least one cognitive domain, for example memory, language, visual-spatial ability or executive function. In some embodiments, memory cognitive domain comprises the ability to learn and/or to recall information. Alternatively or additionally, microstate parameters values represent brain activity related to at least one cognitive domain affected in ADHD or ADD for example, attention and executive function. Optionally, attention and executive function cognitive domains comprise working memory, flexibility, processing speed and data monitoring.

In some embodiments, language cognitive domain comprises comprehension and/or expression abilities related to language. In some embodiments, visuospatial ability comprises comprehension and/or effective manipulation of non-verbal and/or graphic and/or geographic information. In some embodiments, executive function comprises the ability to plan and/or perform abstract reasoning and/or solve problems, and/or focus despite distractions and/or shift focus when appropriate.

In some embodiments, microstates parameters are spatiotemporal representations of at least one brain activity state. In some embodiments, microstate parameters comprise at least two topographic microstate maps, for example 2, 3, 4 topographic microstate maps and the occurrence time of each topographic microstate map.

In some embodiments, microstates are discrete topographic states at local maxima of a global field power curve (GFP) which is calculated based on the EEG signal. In some embodiments the measured microstates are clustered into a set of at least 2 microstate maps, which optionally represent brain activity. In some embodiments, the occurrence time of each map before it shifts to another map is determined. In some embodiments microstate parameters values comprise at least two microstate maps and the occurrence time of each microstate map.

In some embodiments, microstates are extracted from EEG signals that were measured during a resting state. In some embodiments a resting state is achieved when the individual is not actively engaged in sensory and/or cognitive processing, for example when the eyes of the individual are closed.

An aspect of some embodiments relates to using microstate parameters values to evaluate a treatment. In some embodiments, microstate parameters values are used to determine the efficacy and/or the toxicity and/or side effects of a treatment. In some embodiments, microstate parameters values that were measured after a treatment are compared to stored indications which correlate with a clinical and/or a cognitive state, for example to determine the clinical and/or cognitive state after the treatment. In some embodiments if a desired clinical and/or cognitive state is not reached, then the treatment is modified or stopped.

In some embodiments, microstate parameters values measured after a treatment are compared to microstate parameters values of the same patient that were measured before the treatment, for example to determine the efficacy and/or the toxicity and/or side effects of the treatment. In some embodiments, if the determined efficacy is not in a desired range, then the treatment is modified or stopped. Optionally or alternatively, if the determined efficacy is not in a desired range then an indication is provided, for example a clinical and/or a cognitive indication. In some embodiments, the indication is transmitted to a remote computer and/or to a handheld device of an expert, for example a physician.

In some embodiments, a progression profile of a treatment is determined based on a comparison between at least two sets of microstate parameters values that were measured in at least two time points, for example before and after a treatment, or by measuring at least two time points after the treatment is over. In some embodiments, the time difference between the two measurements is at least half an hour, for example half an hour, an hour or 2 hours.

In some embodiments, at least two different treatments are compared based on a comparison between their progression profiles. In some embodiments, a clinical and/or a cognitive state is determined based on a progression profile of a treatment. In some embodiments, a treatment is modified and/or stopped based on a comparison between the progression profile of a treatment to a desired progression profile. In some embodiments, a progression profile is determined based on the number of microstates and/or the occurrence time of each microstate and/or on the shifting sequence between one microstate to another microstate.

In some embodiments, microstate parameters values are measured before the beginning of a treatment session, for example to determine baseline microstate parameters values. Optionally or alternatively, microstate parameters values are measured before the beginning of a treatment for selecting a treatment protocol and/or to modify at least one parameter of an existing treatment protocol.

In some embodiments, microstate parameters values of a patient diagnosed with neurological disease, for example a MCI patient, an AD patient, an ADHD patient or and ADD patient, are measured to select a treatment protocol, for example a transcranial magnetic stimulation (TMS) protocol. In some embodiments, the measured microstate parameters values are used to determine the TMS protocol parameters, for example pulse target and/or pulse frequency and/or pulse duration. Alternatively and/or additionally the measured microstate parameters values are used to determine at least one position on the head for placing the magnetic coil of the TMS device. In some embodiments, the magnetic coil of the TMS is navigated between at least two positions on the head during a single TMS treatment session, based on the measured microstate parameters values.

In some embodiments, microstate parameters values are measured during and/or after a TMS treatment session, for example to determine the efficacy and/or one or more side effects of the treatment. Optionally, the TMS treatment is monitored in real-time by analysis of microstates parameters values. In some embodiments, the TMS protocol parameters are modified based on EEG microstate parameters values that were measured after the treatment session.

An aspect of some embodiments relates to classifying of one or more clinical conditions based on microstates parameter values. In some embodiments, the clinical conditions are classified based on the duration or mean duration of one or more microstates extracted from at least one EEG signal. Alternatively or additionally, the clinical conditions are classified based on the occurrence, frequency and/or number of transitions of one or more microstates extracted from at least one EEG signal. In some embodiments, the one or more clinical conditions comprise AD, MCI, vascular dementia, Mixed Dementia, depression and/or normal cognition.

According to some embodiments, the classification of the one or more clinical conditions is based on the microstates parameter values and on results of cognitive, psychiatric and/or clinical tests. Alternatively or additionally, the classification is based on the microstates parameter values and on one or more additional biomarkers. In some embodiments, the additional biomarkers comprise levels and/or concentration of tau and/or beta-amyloid proteins or mRNA in the brain, blood or in the cerebrospinal fluid (CSF).

According to some embodiments, the classification of the one or more clinical conditions is based on EEG signals recorded at one or more time points. In some embodiments, the EEG signals are recorded during a follow-up period, for example a follow-up period of 2 or more days, or one or more weeks.

An aspect of some embodiments relates to generating a risk indicator based on one or more microstates parameter values. In some embodiments, the risk indicator indicates a probability to be classified in one or more clinical conditions groups. For example a risk indicator indicates a probability to be classified in AD, MCI, depression, vascular dementia, and mixed dementia groups.

According to some embodiments, the risk indicator is generated based on the duration or mean duration of one or more microstates.

An aspect of some embodiments relates to filtering subjects suffering from AD from subjects suffering from other cognitive and/or psychiatric conditions, for example subjects suffering from depression based on microstates parameter values. In some embodiments, AD subjects are filtered based on the duration and/or mean duration of one or more microstates. In some embodiments, AD subjects are filtered based on the occurrence, frequency and/or number of transitions of one or more microstates. Alternatively or additionally, the clinical conditions are classified based on the occurrence, frequency and/or number of transitions of one or more microstates extracted from at least one EEG signal.

An aspect of some embodiments relates to identifying and/or monitoring cognitive decline based in microstates parameter values. According to some embodiments, duration or mean duration of at least one microstate or a combination of 2 or more microstates is used as a biomarker for cognitive decline. In some embodiments, the duration or mean duration of at least one microstate or a combination of 2 or more microstates is recorded and compared to a previously measured value of the same subject, for example to evaluate cognitive decline over time. Alternatively or additionally, the duration or mean duration of at least one microstate or a combination of 2 or more microstates is recorded and compared to stored values or indications, for example to evaluate cognitive decline compared to common disease stages or general disease classifications. Optionally, the duration or mean duration of at least one microstate or a combination of 2 or more microstates is combined with cognitive and/or clinical analysis results to evaluate cognitive decline.

An aspect of some embodiments relates to classifying one or more clinical conditions by personalizing methods for EEG recording, microstates extraction and/or calculation of one or more microstate parameter values. According to some embodiments, the methods used herein for EEG signals recording, extraction of one or more microstates and calculating one or more microstate parameter values are personalized and/or adjusted to a specific subject or to specific one or more clinical conditions. In some embodiments, EEG signals are recorded from one or more electrodes, for example 1,2,4,6,8,10 electrodes or any higher or lower number of electrodes. Optionally, the number of electrodes used for EEG recordings is personalized and/or adjusted to a specific subject and/or to specific one or more clinical conditions. In some embodiments, the frequency range of EEG waves, for example the frequency range of alpha waves, beta waves, gamma waves, delta waves and/or theta waves are personalized and/or adjusted to a specific subject and/or to specific one or more clinical conditions. In some embodiments, the number of extracted microstates is personalized and/or adjusted to each subject or to specific clinical conditions. In some embodiments, the calculated microstates parameter values, the type of microstates parameter and/or the calculation method of the parameter values are personalized and/or adjusted to a specific subject and/or to specific clinical conditions. In some embodiments, the specific clinical conditions comprise MCI, mixed dementia, vascular dementia, AD, AD stages, depression and/or a cognitively normal clinical condition.

An aspect of some embodiments relates to using microstates parameter values in drug development. In some embodiments, one or more microstates are extracted from EEG signals of participants in drug development trials, for example clinical trials. In some embodiments, microstates parameter values from these EEG signals are used to classify experimental groups in the trial, for example treated subjects and/or control subjects. In some embodiments, the microstates parameter values are used for monitoring the effect of a drug on a group of participants, and optionally to compare one group of participants to another group based on one or more microstates parameters. In some embodiments, the microstates parameter values of participants in each group are used to classify a clinical condition or an effect of the drug on the clinical condition. In some embodiments, EEG microstates and microstates parameter values are used as an inclusion criteria in a clinical trial.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Classification of a Clinical State

Figure 1A:
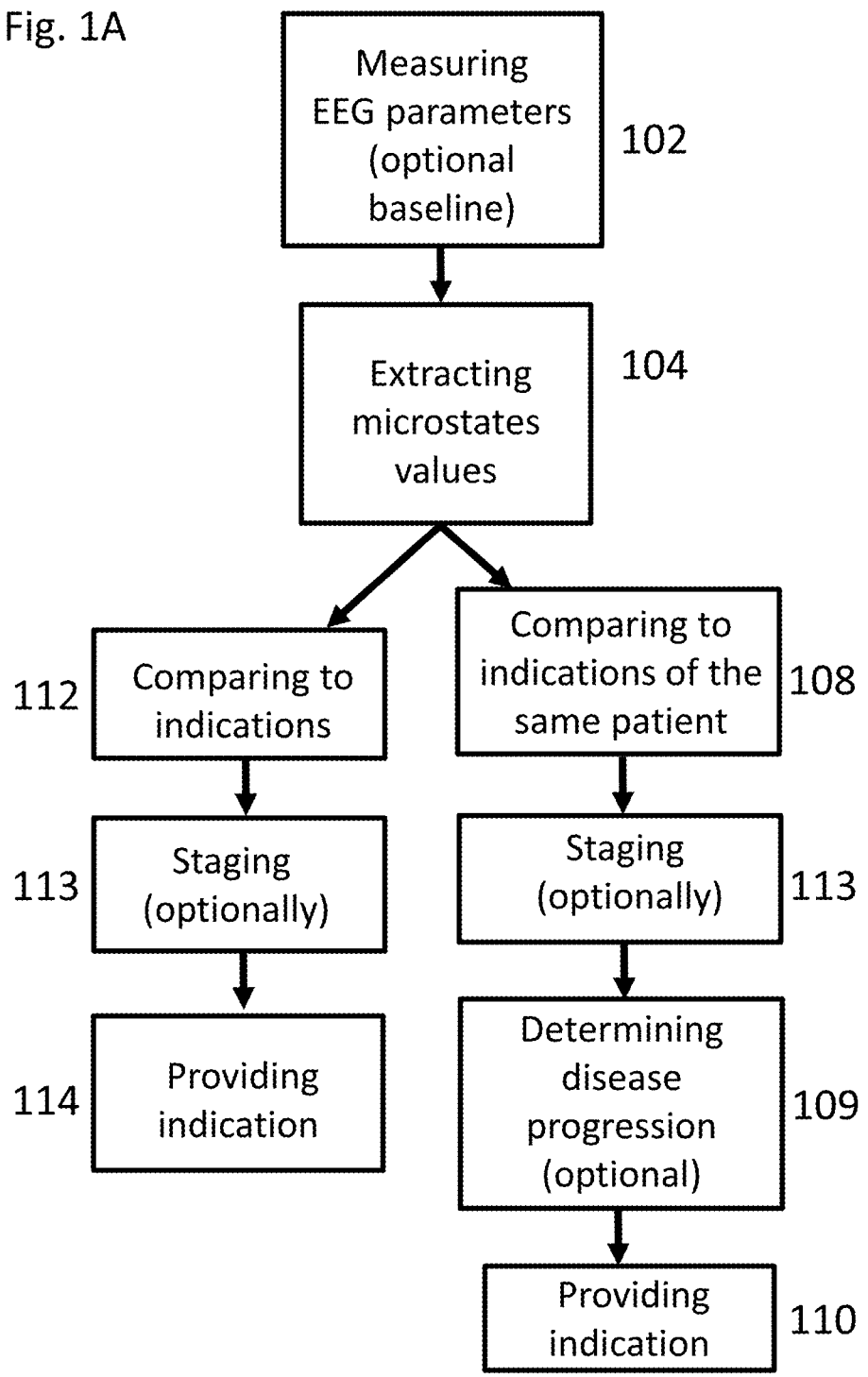

Reference is now made to FIG. 1A depicting a process for classifying a clinical state of a patient based on microstate parameters values, according to some embodiments of the invention.

According to some exemplary embodiments, EEG parameters are measured in a resting-state by at least one electrode connected to a patient's head at 102. In some embodiments, EEG is measured by at least two electrodes connected to the patient. In some embodiments, one of the electrodes serves as a reference electrode to the other electrode. In some embodiments, EEG is measured by a plurality of electrodes positioned on the scalp of a patient, optionally at desired locations. In some embodiments, the desired locations for positioning the plurality of electrodes are determined based on the diagnosis of the patient. Optionally or additionally, the desired locations for positioning the plurality of electrodes are determined based on the patient's head shape and/or size and/or location of desired brain regions.

In some embodiments, the patient lies or sits in a comfortable place with EEG scalp electrodes attached to his scalp. In some embodiments, the EEG measurements duration is between 5 minutes and 30 minutes, for example 15, 20, 25 minutes. In some embodiments, the patient is instructed to open or to close his eyes during EEG measurements. Optionally, the patient is instructed not to fall asleep.

According to some exemplary embodiments, the EEG microstate parameters values are extracted at 104, for example as described in Khanna A. el, al. In some embodiments, EEG measured parameters of brain waves with frequencies in the range of 1-40 Hertz are analyses. In some embodiments, the EEG measured parameters are analyzed as known in the art to extract a plurality of topographic microstates, for example 4, 6, 8 topographic microstates. In some embodiments, each topographic microstate remains stable for at least 60 milliseconds, for example 80-120 milliseconds, before it shifts to a different topographic microstate. Additionally, the duration values of each microstate are also extracted. In some embodiments, microstate parameters comprise at least two parameters, the shifting between at least one topographic microstate to another, and the duration of each microstate. Optionally, these at least two parameters correlate with at least one clinical and/or cognitive state.

According to some exemplary embodiments, the extracted microstate parameters are compared to stored indications at 112. In some embodiments, the stored indications correlate with at least one clinical and/or cognitive state, for example a neurological clinical condition. Optionally, the stored indications and/or stored microstates parameters values correlate with at least one stage of a disease.

According to some exemplary embodiments, a stage of the disease is determined at 113. In some embodiments, the disease stage is determined based on comparison between the extracted microstates parameter values and stored indication and/or stored microstates parameter values which correlate with at least one stage of the disease.

In some embodiments, extracted microstates parameter values are combined with at least one parameter value related to the cognitive state, physiological state and/or behavioral state of the patient, for example to generate a combined score which reflects the current state of the patient. In some embodiments, the combined score is compared to stored microstates parameter values and/or stored indications which correlate with at least one stage of the disease, for example to determine the current disease stage of the patient. Optionally, the combined score is compared to stored microstates parameter values and/or stored indications to determine a correlation with at least one stage of the disease.

According to some exemplary embodiments, a human-detectable indication is provided based on the comparison between the extracted microstate parameters values and the stored indication, at 114. In some embodiments, the human-detectable indication comprises a clinical indication based on the correlation between the stored indications and a clinical and/or cognitive state. In some embodiments, a clinical classification of a neurological condition is made based on the comparison between the extracted microstate parameters values and the stored indications.

According to some exemplary embodiments, the extracted microstate parameters values are compared to stored indications of the same patient at 108. In some embodiments, the current stage of the disease is determined, for example as described at 113.

In some embodiments, the progression of the disease is determined at 109, for example by comparing the current disease state and/or clinical condition of the patient to previously determined disease state of the same patient. In some embodiments a disease state or a disease stage is determined by combining extracted microstates parameter values with at least one clinical or a behavioral value, optionally to generate a combined score. In some embodiments, the combined score correlates with at least one indication of disease stage and/or a clinical state. Optionally, the progression of a disease is determined by at least one differential indication between at least two sets of microstates parameter values or between two measured clinical and/or behavioral values. Alternatively, the progression of a disease is determined by at least one differential indication between two combined scores. In some embodiments, it is a potential advantage of the described method that extracted microstates parameter values allows monitoring of a disease progression, and/or early detection of a disease or a symptom of a disease.

According to some exemplary embodiments, a human-detectable indication is provided at 110 based on the comparison between at least two sets of extracted microstate parameters values of the same patient, when each of the two sets is based on a different EEG parameters measurement. In some embodiments, comparing microstate parameters values of the same patient, which are based on two different EEG measurements allows to monitor the progression of a neurological condition, for example the progression of a disease.

According to some exemplary embodiments, at least one EEG parameter correlates with at least one clinical and/or cognitive state of the neurological disease.

In some embodiments, the change in the average duration of a given microstate correlates with at least one clinical and/or cognitive state of the neurological disease, for example microstate duration is shorter or longer in a clinical stage or a cognitive state of a disease compared to a different stage of the disease or to a microstate of a healthy individual.

Alternatively or additionally, the change in the total duration of a given microstate correlates with at least one clinical and/or cognitive state of the neurological disease, for example, more time is spent in microstate A during all the EEG recording in a clinical stage of a neurological disease.

Alternatively or additionally, the change in the transition pattern between microstates correlates with at least one clinical and/or cognitive state of the neurological disease, for example, the transition from microstate A to C in a clinical stage of the disease compared to microstates of a different disease stage or to microstates of healthy individuals.

According to some exemplary embodiments, determining a stage of a clinical condition is based on comparison between at least one microstate parameters value of a first EEG signal and at least one microstate parameters value extracted from a second EEG signal. In some embodiments, a clinical stage and/or a cognitive state is determined based on at least one differential indication between the compared microstate parameters values.

Exemplary Microstates Extraction

Figure 1B:
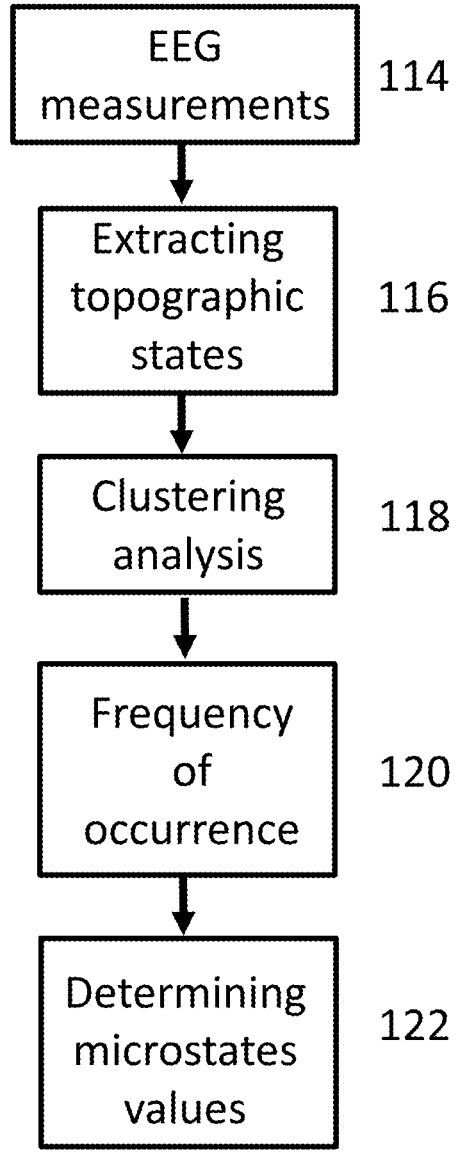

Reference is now made to FIG. 1B depicting a process for extraction of microstate parameters values from EEG parameters, according to some embodiments of the invention.

According to some exemplary embodiments, EEG parameters are measured at 114, by at least two electrodes placed in contact with the head of an individual. In some embodiments, at least one electrode serves as a reference electrode to the rest of the electrodes. In some embodiments, EEG parameters are measured during a resting state of the individual. In some embodiments a resting state is achieved when the individual is not actively engaged in sensory and/or cognitive processing, for example when the eyes of the individual are closed. In some embodiments, EEG measures brain waves with frequencies of 1-4 Hertz (delta waves), 4-7 Hertz (theta waves) and/or 8-12 Hertz (alpha waves), 12-28 Hertz (beta waves), and/or >30 Hertz (gamma waves). In some embodiments, EEG parameters are measured as described in Khanna et. al. 2015.

According to some exemplary embodiments, EEG topographic states are extracted from the EEG measurements at 116. In some embodiments, the EEG signal is analyzed to generate a global field power (GFP) curve. In some embodiments, the GFP curve represents the strength of the electric field over the brain at each instant. In some embodiments, the GFP curve is used to measure the brain response to an event, or to characterize the rapid changes in brain activity. In some embodiments, a local maximum of GFP curve represents instants of strongest field strength and highest topographic signal to noise ratio. In some embodiments, the topographies of the electric field at local maxima of the GFP curve are considered discrete states of the EEG. Optionally, these discrete states are termed EEG microstates.

According to some exemplary embodiments, a clustering analysis of the extracted microstates is performed at 118. In some embodiments, a clustering algorithm groups the extracted microstates into sets of clusters. In some embodiments, the clustering is based on topographic similarity between some of the extracted microstates. In some embodiments, EEG microstates, for example resting-state EEG microstates are clustered into a set of 2, 3, 4, 5, 6, for example 4 microstate maps.

According to some exemplary embodiments, the frequency of occurrence of each microstate map is determined at 120. In some embodiments, a single microstate map remains stable for 50-150 milliseconds, for example 80-120 milliseconds before transitioning to a different microstate map. In some embodiments, the occurrence time of each microstate map before its transition into a new microstate map is calculated.

According to some exemplary embodiments, microstate parameters values are determined at 122, based on the clustering analysis of the topographic states and/or based on the frequency of occurrence of each microstate map that was determined at 120. In some embodiments, microstate parameters comprise at least two microstate maps, for example 2, 3, 4 microstate maps, and the occurrence time of each microstate map.

In some embodiments, microstates are extracted from EEG measurements by comparing the topography at each successive GFP peak to the previous GFP peak and consider it as the start of a new microstate if the centroid locations of the positive or negative potentials change by more than a predetermined level (Lehman et al., 1987).

Alternatively, microstates are extracted from EEG measurements by independent component analysis to define microstate classes (Musso et al., 2010; Yuan et al., 2012).

Exemplary Treatment Monitoring Based on Microstate Parameters Values

Figure 2:
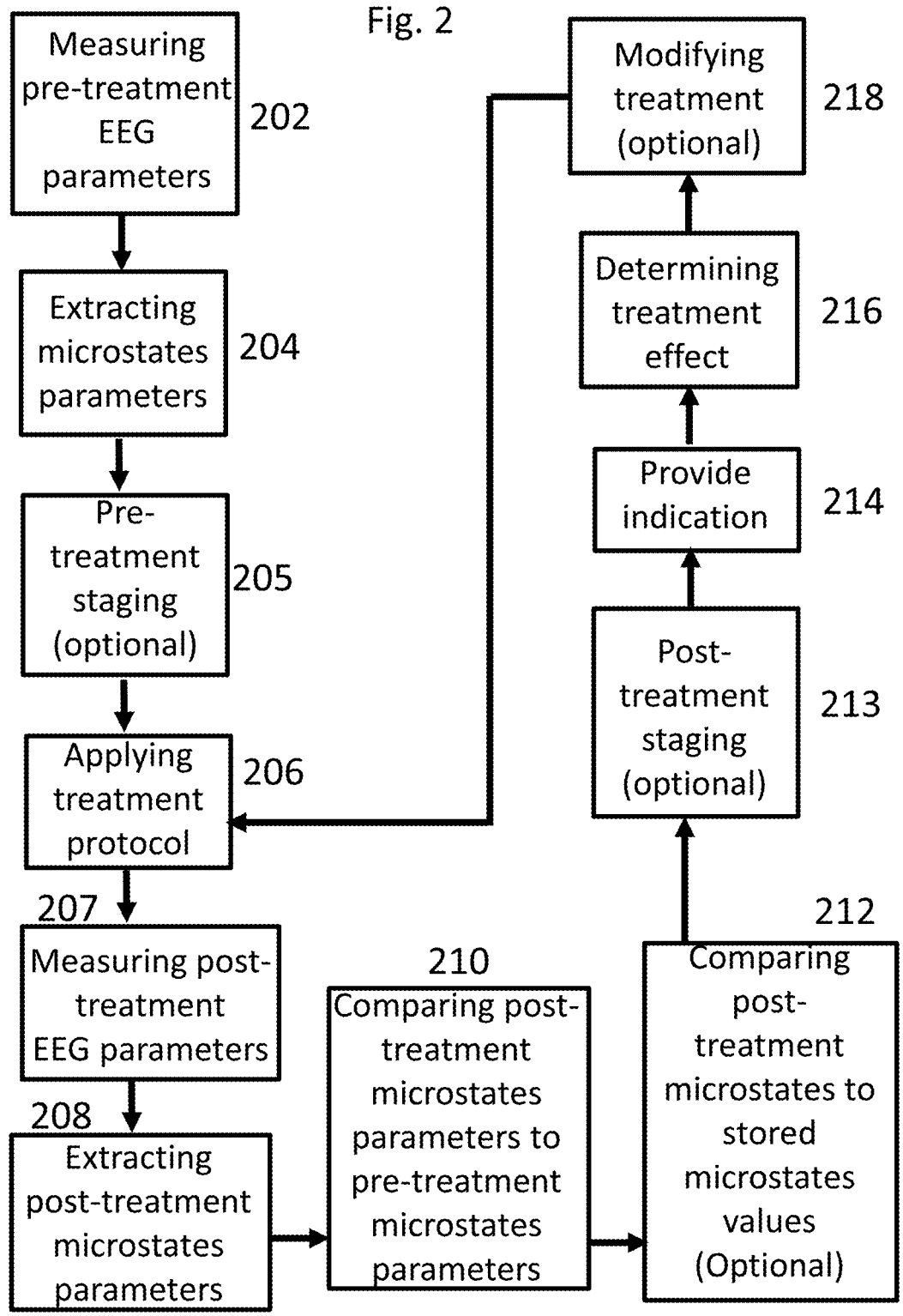

According to some embodiments, microstate parameters values are extracted from EEG measurements that were taken during and/or after a treatment. In some embodiments, the extracted microstate parameters values are compared to stored microstate parameters values, for example to allow treatment monitoring and/or modification. Reference is now made to FIG. 2 depicting a process of treatment monitoring and/or modification according to some embodiments of the invention.

According to some exemplary embodiments, EEG parameters are measured before the initiation of a treatment at 202. In some embodiments, the EEG parameters are measured during a resting state when a subject, for example a patient is not actively engaged in sensory or cognitive processing. Optionally, the resting state EEG parameters are measured when a subject is requested to close his eyes. In some embodiments, EEG parameters are measured as described previously. In some embodiments, the pre-treatment EEG parameters are measured at least 1 minute before the treatment.

According to some exemplary embodiments, microstate parameters values are extracted from pre-treatment EEG parameters at 204, for example as described in Khanna A. el, al. and/or as described in FIG. 1B. In some embodiments, EEG parameters are measured by at least one electrode connected to the head of a patient. Optionally, EEG parameters are measured by at least two electrodes connected to the head of a patient, where at least one of the electrodes serves as a reference electrode to the rest of the electrodes. In some embodiments, the pre-treatment microstate parameters values serve as a baseline or as a reference for the following extracted microstate parameters values. In some embodiments, the pre-treatment microstate parameters values are compared to stored microstate parameters values which correlate with at least one clinical and/or cognitive state, for example for diagnosis of a clinical condition. Alternatively or additionally, a treatment protocol is selected based on the extracted pre-treatment microstate parameters values and/or based on the comparison of the pre-treatment microstate parameters values to stored microstate parameters values.

Optionally, a pre-treatment disease stage is determined at 205, for example as described at 113. In some embodiments a treatment is selected, and/or treatment parameters are adjusted to match the determined disease state.

According to some exemplary embodiments, a treatment protocol, for example a treatment that stimulates the brain is applied at 206. In some embodiments, the treatment protocols is determined based on previously extracted microstate parameters values of the patient and/or based on stored microstate parameters values. Optionally, the treatment protocol is adjusted for the treatment of at least one clinical and/or cognitive state that was determined based on microstate parameters values.

According to some exemplary embodiments, EEG parameters are measured during and/or after the application of the treatment protocol at 207. In some embodiments, EEG parameters are constantly measured during the application of the treatment protocol. In some embodiments, post treatment EEG parameters are measured at least 1 minute after the treatment, for example 1 minute, 5 minutes, 10 minutes, 30 minutes, 1 hour after the treatment.

According to some exemplary embodiments, microstate parameters values are extracted from at least one selected EEG parameters set at 208, for example as described in Khanna A. el, al. and/or as described in FIG. 1B.

According to some exemplary embodiments, the post-treatment microstate parameters values are compared to the pre-treatment microstate parameters values of the same patient at 210. Optionally, the post-treatment microstate parameters values are compared to stored microstate parameters values of the patient and/or to stored microstate parameters values of other patients at 212 which correlate with at least one clinical and/or cognitive state. In some embodiments, the clinical and/or cognitive state of the patient after the treatment is determined based on the comparison between the post-treatment microstate parameters values and stored microstate parameters values.

In some embodiments, the post-treatment microstates parameter values are compared to stored microstates parameter values or to an indication of microstates parameter values to determine if the post-treatment values are in a desired range of stored values and/or in a desired relation from the stored values or indications.

Optionally, the disease stage post-treatment is determined at 213, for example as described at 113. In some embodiments, the disease progression or regression following the treatment is determined, for example by comparing the post-treatment disease stage to the pre-treatment disease stage.

According to some exemplary embodiments, a human-detectable indication is provided based on the comparison between at least two microstate parameters values, where at least one of the at least two microstate parameters values is extracted from pre-treatment EEG parameters at 214. In some embodiments the human-detectable indication is delivered to the patient and/or to a caregiver and/or to a health professional for example a physician. In some embodiments the human-detectable indication includes the clinical and/or cognitive state of the patient. In some embodiments the indication is based on at least one microstate parameters values comparison. In some embodiments, the human-detectable indication is transmitted to a computer and/or to a handheld device by a wireless, for example a Wi-Fi, a Bluetooth, an infra-red signal, and/or a wired signal.

According to some exemplary embodiments, the treatment effect, for example treatment efficacy and/or treatment efficiency and/or toxicity and/or side effects, is determined based on at least one comparison between the determined clinical and/or cognitive condition of the patient after the treatment to the determined clinical and/or cognitive condition of the patient before the treatment at 216. Alternatively, the treatment effect is determined based on the clinical and/or cognitive condition of the patient after the treatment. Optionally, the treatment effect, for example treatment efficacy and/or treatment efficiency is determined by comparing at least one extracted microstate parameter value to a desired value, and determining if the extracted microstate parameter value is smaller or larger in a desired range from the desired value, for example 1%-50% larger or smaller from the desired value. Optionally, the treatment effect is determined by comparing the disease stage post treatment to a desired disease stage. In some embodiments, the treatment effect is determined by comparing the disease progression or regression following the treatment, to a desired progression or regression.

According to some exemplary embodiments, the treatment and/or the treatment protocol is modified based on the determined clinical and/or cognitive condition of the patient at 218. In some embodiments, the treatment parameters are modified, for example treatment duration and/or the intervals between two treatment sessions. Alternatively, the treatment is replaced by a different treatment, for example a brain stimulation treatment is replaced with a drug-based treatment.

According to some exemplary embodiments, if the microstate parameters values following the treatment indicate a progression towards desired microstate parameters values, for example microstate parameters values representing a healthy individual, then the TMS treatment is repeated. Alternatively, if the microstate parameters values following the treatment indicate, for example deterioration in the clinical and/or cognitive condition of the patient towards undesired microstate parameters values, then the TMS protocol is replaced or at least one parameter of the TMS protocol is modified. Optionally, if the microstate parameters values are not desired microstate parameters values then the time schedule and/or one or more brain targets of the TMS treatment are modified.

In some embodiments, the objective of the treatment, for example the TMS treatment is to shift microstates parameters values which correlate with a disease state to microstates parameters values which correlate with a healthy state. In some embodiments, the treatment is monitored by real-time analysis of extracted microstates parameters values.

Exemplary Monitoring Drug Effect Based on Microstate Parameters Values

Figure 3:
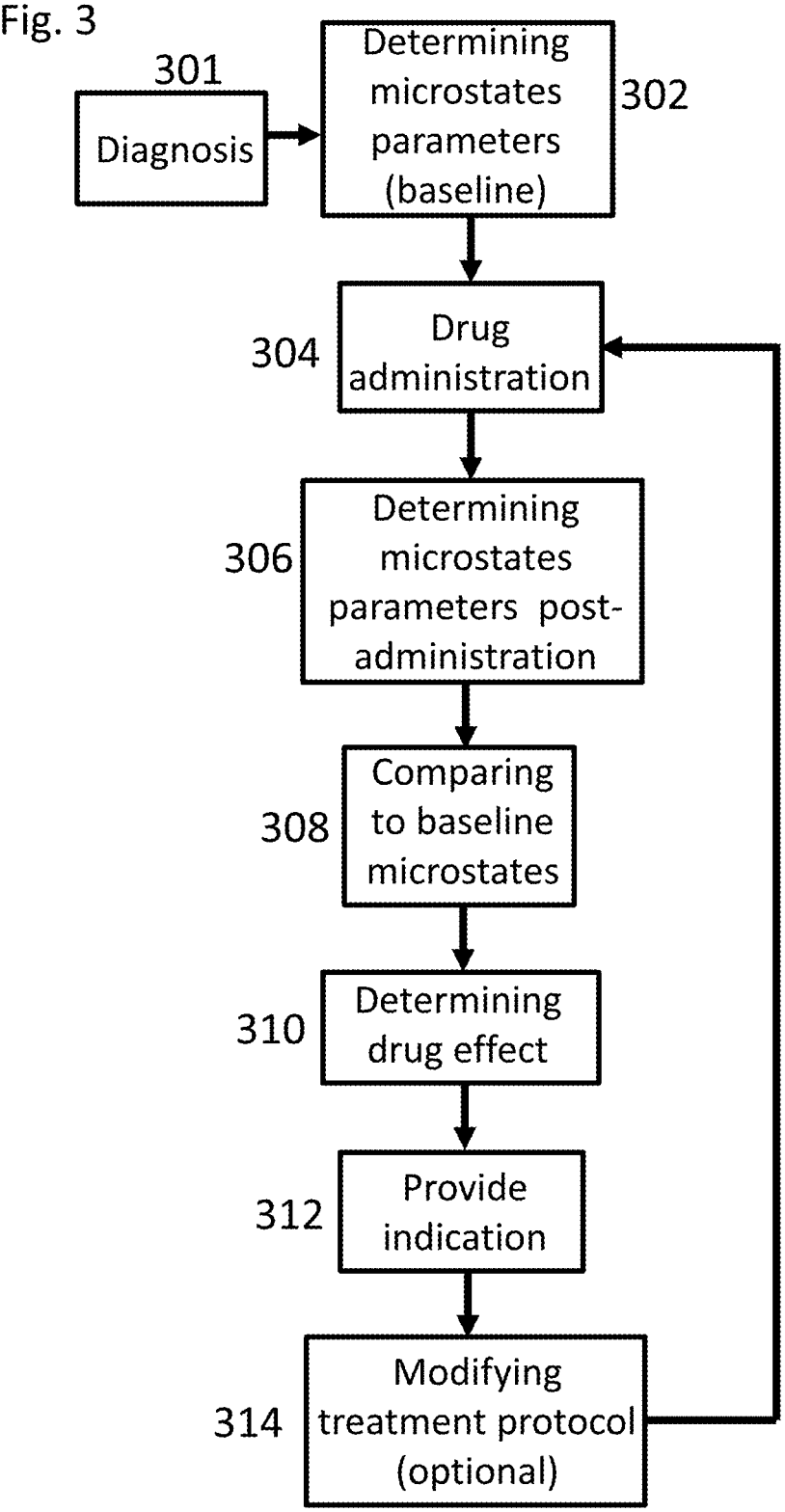

According to some embodiments, a drug is evaluated based on microstate parameters values. In some embodiments, microstate parameters values of EEG parameters measured before and after the administration of a drug are compared, for example to determine the efficacy and/or the toxicity and/or one or more side effects of the drug. Alternatively, microstate parameters values extracted from EEG parameters measured after the drug administration, are compared to stored microstate parameters values which correlate with at least one clinical and/or cognitive state. In some embodiments the drug administration protocol is modified based on the comparison between the two sets of microstate parameters values and/or based on the comparison to stored microstate parameters values. Reference is now made to FIG. 3 depicting a process of drug evaluation based on microstate parameters values.

According to some exemplary embodiments, EEG parameters are measured by at least one electrode connected to the head of a patient before drug administration, as described in FIGS. 1A and 1B. In some embodiments, EEG parameters are measured at least an hour prior to drug administration, for example an hour, two hours, or a day.

In some embodiments, EEG parameters are measured during resting state, for example when the patient is not actively engaged in sensory or cognitive processing. In some embodiments a resting state is achieved when the patient closes his eyes.

According to some exemplary embodiments, microstate parameters values are extracted from the pre-treatment EEG measurements at 302. In some embodiments, EEG microstate parameters values are extracted as described at Khanna A. el, al. and/or as described at FIG. 1B. In some embodiments, the extracted microstate parameters values are compared to stored microstate parameters values which correlate with at least one clinical and/or cognitive state, for example to determine the clinical condition of the patient before drug administration. In some embodiments, the extracted microstate parameters values set at 302 serve as a base line or a reference for at least another microstate parameters values set.

According to some exemplary embodiments, at least one drug is administered, for example as part of a treatment protocol at 304. In some embodiments, at least one drug administration parameter, for example drug dosage is determined based on the extracted microstate parameters values. Alternatively and/or additionally, at least one drug administration parameter is determined based on the clinical condition of the patient as determined, for example by the extracted microstate parameters values.

According to some exemplary embodiments, EEG parameters are measured post drug administration. In some embodiments, EEG parameters are measured at least an hour after drug administration, for example an hour, two hours, or a week after drug administration. Alternatively, the time interval between drug administration and EEG parameters measurement is determined by pharmacokinetic and/or pharmacodynamics parameters of the drug. In some embodiments, microstate parameters values are extracted from the measured post drug administration EEG parameters at 306. In some embodiments, the pre and/or post drug administration microstate parameters values are compared to stored microstate parameters values which correlate with at least one clinical and/or cognitive state, for example to determine the clinical condition of the patient before and/or after drug administration.

According to some exemplary embodiments, post-drug administration microstate parameters values are compared to baseline microstate parameters values at 308. In some embodiments, drug effect, for example drug efficacy and/or toxicity and/or one or more side effects is determined based on the comparison at 310. Alternatively or additionally, drug effect is determined based on the comparison between the post-drug administration microstate parameters values and stored microstate parameters values, which correlate with at least one clinical and/or cognitive state. Optionally, drug effect is determined by comparing at least one extracted microstate parameter value to a desired value, and determining if the extracted microstate parameter value is smaller or larger in a desired range from the desired value, for example 1%-50% larger or smaller from the desired value.

According to some exemplary embodiments, a human-detectable indication is provided at 312 regarding drug efficacy and/or drug toxicity. Alternatively or additionally, the indication is delivered regarding the clinical and/or cognitive state of the patient. In some embodiments, the human-detectable indication is generated a computer and/or a handheld device. In some embodiments, the human-detectable indication is delivered to the patient and/or a caregiver and/or a health professional for example a physician.

According to some exemplary embodiments, at least one parameter of the treatment protocol is modified at 314, for example the duration of the treatment protocol and/or the time interval between two treatment sessions. In some embodiments, at least one parameter of the treatment protocol, for example drug dosage, combination with other drugs or the intervals between each drug administration, is modified based on the determined drug efficacy and/or drug toxicity and/or the determined clinical condition of the patient.

Exemplary Microstates Analysis Device

Figure 4A:
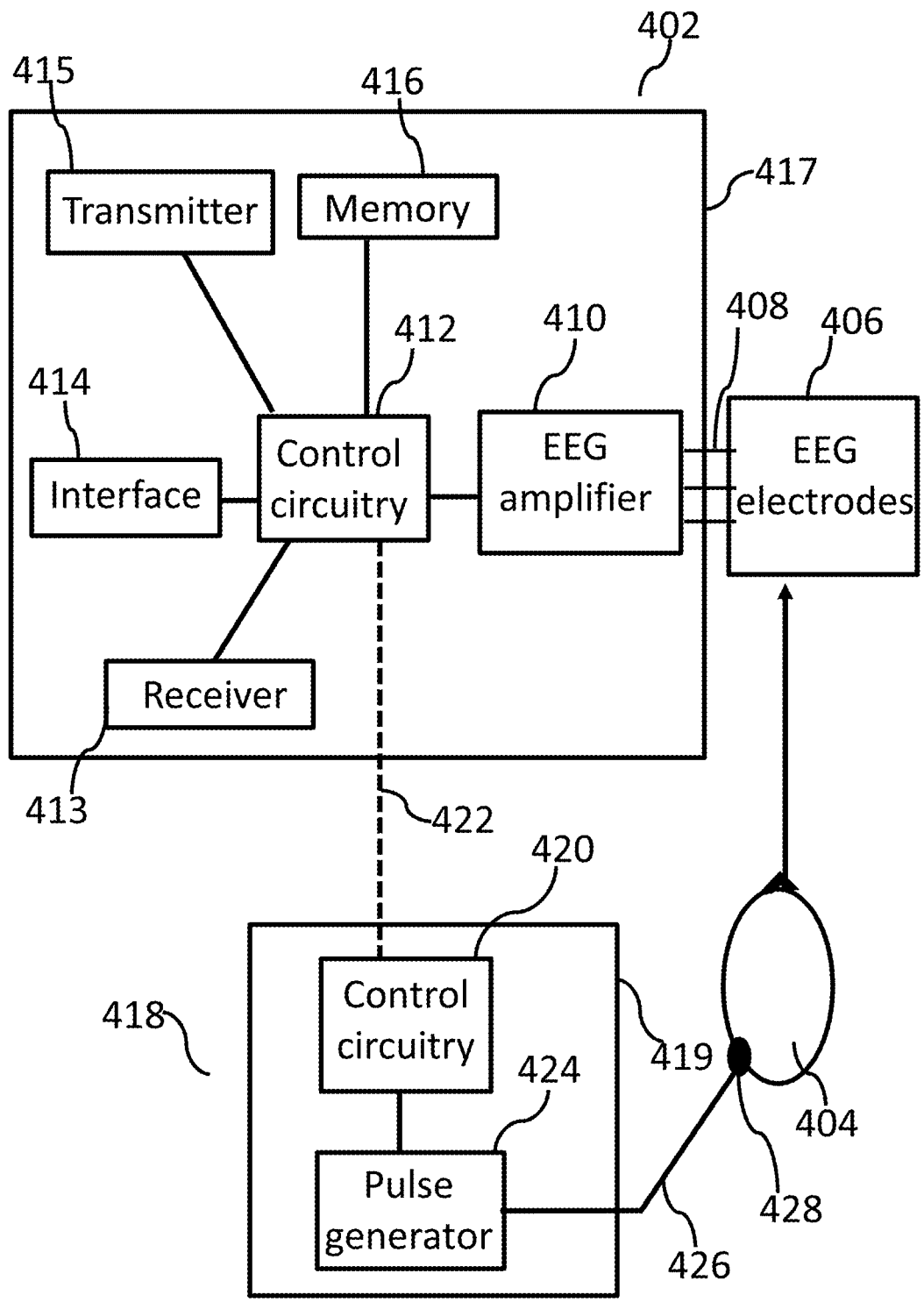

According to some embodiments, an electric device measures EEG parameters from electrodes connected to the head of a patient, and extracts microstate parameters values based on the measured EEG parameters. In some embodiments the electric device transmits a signal to a brain stimulation device, for example to modify a brain stimulation treatment based on the measured microstate parameters values. Reference is now made to FIG. 4A depicting a device for EEG measurements and extraction of microstate parameters values, according to some embodiments of the invention.

According to some exemplary embodiments, at least two EEG electrodes, for example EEG electrodes 406 are attached to the head of a patient 404 and transmit EEG signals, through wiring 408 to device 402. Alternatively, electrodes 406 are wirelessly connected to device 402, for example by a Wi-Fi, Bluetooth or an infra-red connection.

In some embodiments, at least one of EEG electrodes 406 serves as a reference electrode to the other electrodes. Optionally at least one of the EEG electrodes is re-positioned on the head of the patient, for example, following EEG measurements and/or microstates extraction.

According to some exemplary embodiments, the EEG signals are amplified by EEG amplifier 410 before it is received by control circuitry 412 of device 402. In some embodiments, control circuitry 412 stores the EEG signals in memory 416. In some embodiments, control circuitry 412 analyses the EEG signals and extracts microstate parameters values using a program stored in memory 416. In some embodiments, the microstate parameters values are stored in memory 416. In some embodiments, control circuitry 412 transmits microstate parameters values to a computer and/or a handheld device and/or a remote storage device by a wireless signal, for example a Wi-Fi, a Bluetooth or an infra-red signal. Alternatively or additionally, control circuitry delivers the microstate parameters values via a wire to a computer.

According to some exemplary embodiments, memory 416 stores at least one set of microstate parameters values. In some embodiments, memory 416 stores at least one clinical and/or cognitive state parameters which correlate with the stored microstate parameters values set. In some embodiments, control circuitry 412 compares between at least two sets of microstate parameters values that are stored in memory 416. Optionally, device 402 provides a human-detectable indication regarding the compared microstate parameters values and/or at least one clinical and/or cognitive state which correlates with at least one set of microstate parameters values, using interface 414. In some embodiments, device 402 comprises housing 417 fitted to place device 402 next to the patient or to attach device 402 to the patient's body, for example to the patient's hand or head.

According to some exemplary embodiments, device 402 comprises a receiver, for example receiver 413. In some embodiments, receiver 413 receives wireless signals, for example Wi-Fi, Bluetooth or infra-red signals from a computer and/or a handheld device and/or a remote storage. In some embodiments, receiver 413 receives at least one set of microstate parameters values, clinical and/or cognitive states associated with the microstate parameters values and at least one operation program. In some embodiments, the received data is stored in memory 416, or in an external memory component, for example a USB memory stick.

According to some exemplary embodiments, device 402 comprises a transmitter, for example transmitter 415. In some embodiments, transmitter 415 transmits wireless signals, for example Wi-Fi, Bluetooth and/or infra-red signals to a computer and/or a handheld device.

According to some exemplary embodiments, device 402 is connected wirelessly or by wires to a brain stimulation device 418, for example a TMS device. In some embodiments, the wireless connection includes Wi-Fi, Bluetooth or an infra-red connection. In some embodiments control circuitry 420 of stimulation device receives a signal from device 402. In some embodiments, control circuitry 420 determines brain stimulation parameters based on the signal received from device 402. In some embodiments, control circuitry 420 signals pulse generator 424 to generate at least one pulse according to the stimulation parameters. In some embodiments, the generated pulse is delivered through wiring 426 to an electrode 428 connected to the patient 404 head, for example a magnetic coil or to an electrode placed in a close proximity to the head.

In some embodiments, brain stimulation device 418 comprises housing 419.

According to some exemplary embodiments, the EEG electrodes are wirelessly connected to a handheld device. In some embodiments, the wireless connection includes Wi-Fi, Bluetooth or an infra-red connection. In some embodiments, the handheld device receives the EEG signals and extracts microstate parameters values from the EEG signal using a program or an application stored in the device. In some embodiments, the handheld device compares at least two sets of microstate parameters values and provides a human-detectable indication, for example a clinical indication based on the correlation between the microstate parameters values and a clinical and/or cognitive state. In some embodiments, the handheld device transmits the microstate parameters values and/or the clinical indication to a computer and/or to another handheld device and/or to a remote storage and/or to a stimulation device.

Exemplary Microstates Analysis and Stimulation Device

Figure 4B:
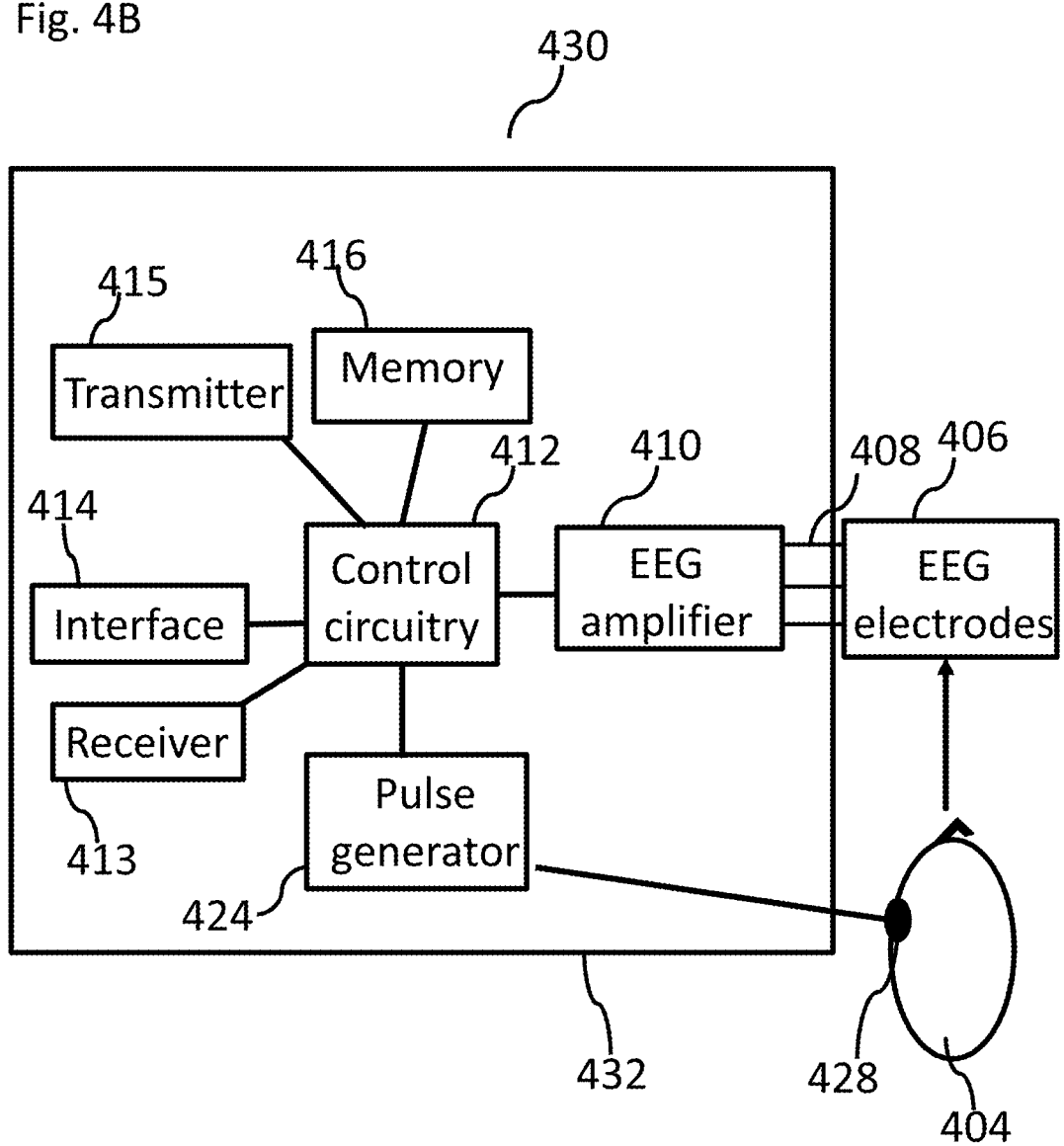

According to some embodiments, an EEG measurements and microstates analysis device is configured to deliver stimulation to a patient's brain. Reference is now made to FIG. 4B depicting a device for EEG measurements, microstate analysis and brain stimulation, according to some embodiments of the invention.

According to some exemplary embodiments, device 430 receives EEG signals from electrodes connected to a patient's head, and extract microstate parameters values from the EEG signals. In some embodiments, the electrodes are wirelessly connected to device 430, for example by a Wi-Fi, Bluetooth or an infra-red connection. In some embodiments, control circuitry 412 extracts microstate parameters values from the EEG signals, and signals pulse generator 424 to generate at least one pulse based on the microstate parameters values or based on other parameters stored in memory 416. Alternatively, the at least one pulse parameters are determined based on the comparison between at least two sets of microstate parameters values, or on the comparison between microstate parameters values and other parameters stored in memory 416.

In some embodiments, control circuitry 412 determines pulse parameters according to a program stored in memory 416.

According to some exemplary embodiments, pulse generator 424 generates and delivers at least one pulse to at least one electrode 428, as described previously.

According to some exemplary embodiments, memory 416 stores at least one operation program of device 430 and/or microstate parameters values and/or EEG measurements and/or TMS parameters.

According to some exemplary embodiments, receiver 413 receives wireless signals, for example Wi-Fi, Bluetooth, or infra-red signals from a computer and/or a handheld device. In some embodiments, receiver 413 receives TMS parameters and/or at least one operation program of device 430 and/or EEG measurements and/or microstate parameters values, to be stored in memory 416.

Figure 5A:
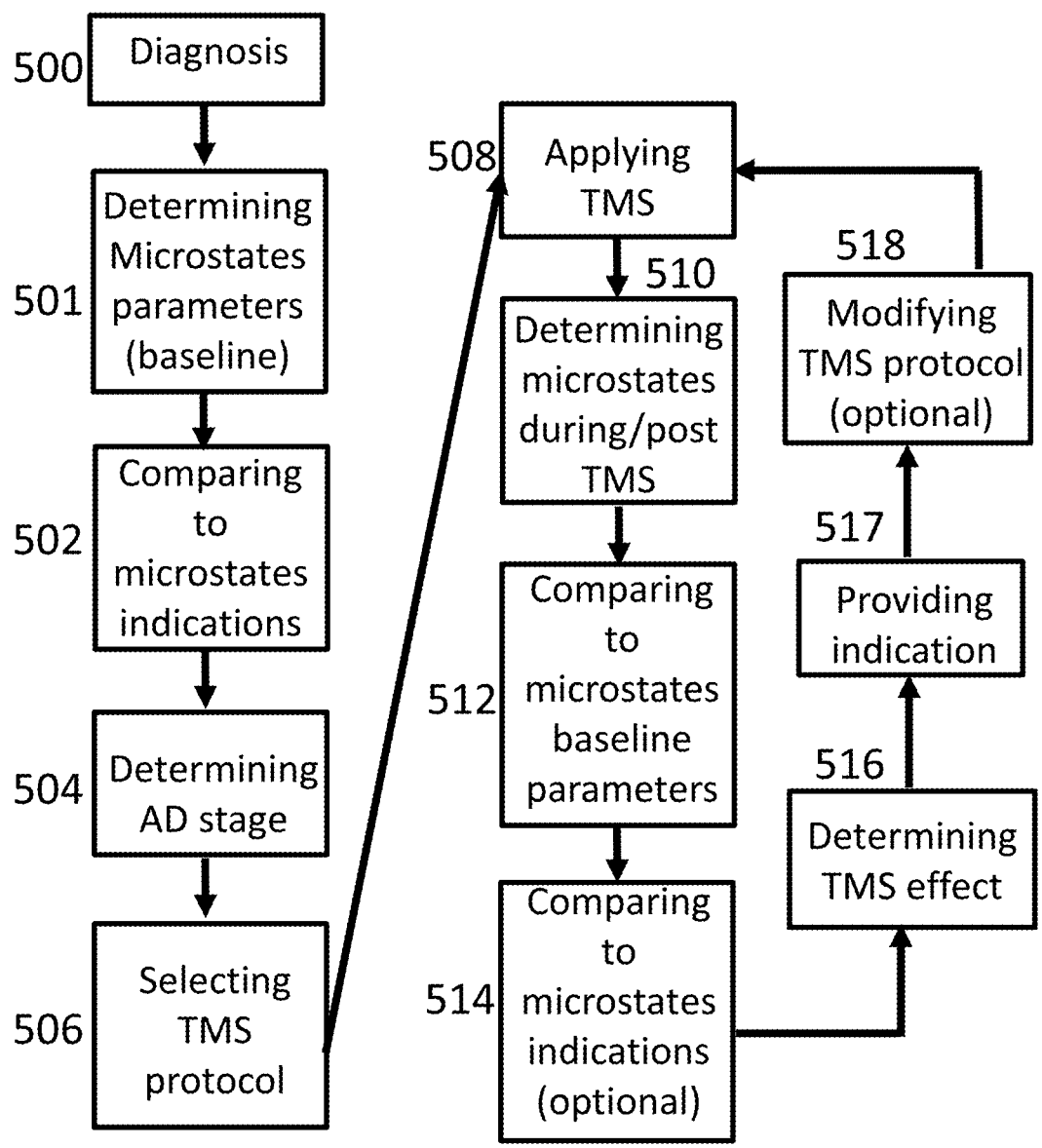

Exemplary Process of Monitoring and Adjusting a TMS Treatment for MCI AD, ADHD or ADD Based on Microstate Parameters Values According to some embodiments, dementia patients microstate parameters values are used to determine the dementia stage and to adjust and monitor the effect of a treatment, for example a TMS treatment. Reference is now made to FIG. 5A depicting a process of adjusting a TMS treatment for MCI, AD, ADHD and/or ADD patients based on microstate parameters values of the patients, according to some embodiments of the invention.

According to some exemplary embodiments, the cognitive and/or clinical state of a patient suffering from at least one cognitive and/or neurological symptom is analyzed at 500. In some embodiments, the analysis is conducted by using cognitive tests, for example ADAS-COG or MMSE. Optionally, brain imaging techniques are used, for example MRI, CT, PET-CT. In some embodiments, body fluids analysis is used, for example blood test analysis, cerebral spinal fluid analysis to determine the cognitive and/or clinical state of the individual. In some embodiments, diagnosis comprises patient anamnesis, and/or cognitive evaluation, and/or functional evaluation, and/or analysis of at least one biomarker.

According to some exemplary embodiments, after diagnosis at 500, EEG parameters are measured. In some embodiments, at least two electrodes are connected to the patient's head and measure EEG parameters when the patient is in a resting state, for example when the patient is not actively engaged in sensory or cognitive processing. In some embodiments a resting state is achieved when the patient closes his eyes. In some embodiments, EEG is measured at least 1 minute before the treatment, for example 1 minute, 5 minutes, 10 minutes before the treatment.

According to some embodiments, microstate parameters values are extracted from the EEG parameters at 501 as described in Khanna A. et, al. and/or as described in FIG. 1B. According to some exemplary embodiments, the extracted microstate parameters values of the patient are compared to stored microstates indications of other patients and/or to stored microstates indications of the same patient at 502. In some embodiments, the stored microstates indications correlate with at least one clinical and/or cognitive state.

According to some exemplary embodiments, the comparison between the extracted microstate parameters values and the stored microstates indications which correlate with at least one clinical and/or cognitive state allows for example to determine the progression of a disease. In some embodiments, comparing microstate parameters values of an AD patient to stored microstates indications which correlate with specific AD stages allows for example to determine the AD stage of the patient at 504. Optionally, comparing microstates parameter values of an individual to stored microstates indication which correlate with at least one stage of AD allows for example, early detection of mild cognitive impairment (MCI) which is one of the early stages of dementia. Additionally, this comparison allows, for example to monitor the progression from MCI to AD or from mild AD to moderate AD, or from MCI to other types of dementia.

According to some exemplary embodiments, determining the clinical and/or cognitive state of the patient, for example the AD stage of the patient, allows to select a treatment adjusted to the specific patient. In some embodiments, a treatment protocol, for example a TMS treatment is selected based on the determined clinical and/or cognitive state of the patient at 506. Optionally, treatment parameters are determined based on the determined clinical and/or cognitive state.

According to some exemplary embodiments, the selected TMS protocol is applied at 508. In some embodiments, during the TMS treatment an electric field is applied through an electrode or a magnetic coil. In some embodiments, the electrode or the magnetic coil are attached to the scalp of the patient.

According to some exemplary embodiments, during the TMS treatment session, for example between pulses, EEG parameters are measured and microstate parameters values are extracted at 510. Alternatively, EEG parameters are measured and stored, for example for later extraction of microstate parameters values. In some embodiments, EEG parameters are measured after the completion of the TMS treatment session, for example 1 minute, 5 minutes, 10 minutes, 20 minutes, after the completion of the treatment session.

According to some exemplary embodiments, the microstate parameters values that were extracted after the TMS application are compared to stored microstate parameters values at 512, for example microstate parameters values of the same patient that were determined before the treatment or the treatment session, as described at 501. Alternatively, the microstate parameters values that were extracted after the TMS application are compared to microstates indications stored in a memory, at 514.

According to some exemplary embodiments, the TMS treatment effect, for example the TMS treatment applied at 508, is determined at 516. In some embodiments, the TMS treatment effect, for example the TMS treatment efficacy is determined based on the comparison between the post-treatment microstate parameters values to the pre-treatment microstate parameters values. Alternatively or additionally, the TMS treatment effect is determined based on the comparison between the post treatment microstate parameters values to stored microstate parameters values of other patients. Optionally, the TMS treatment effect is determined by comparing the post treatment microstate parameters values to desired microstate parameters values. In some embodiments, the TMS treatment effect is determined based on the comparison between the clinical and/or cognitive state which correlates with the post-treatment microstates and a desired clinical and/or cognitive condition.

According to some exemplary embodiments, a human-detectable indication is provided regarding the TMS treatment effect at 517. In some embodiments, the human-detectable indication includes the clinical and/or cognitive state of the patient and/or the microstate parameters values after the application of the TMS treatment. Optionally, the human-detectable indication includes at least one suggested modification to the TMS treatment protocol, for example at least one modification of TMS parameters. In some embodiments, a computer or a handheld device is signaled via a wireless signal, for example a Wi-Fi, an infra-red or a Bluetooth signal to generate the human-detectable indication. Alternatively, a computer receives a wired signal to generate the human-detectable indication. In some embodiments, the patient and/or a health professional, for example a physician, responds to the human-detectable indication using an interface circuitry or an application program.

According to some exemplary embodiments, the TMS protocol is optionally modified at 518. In some embodiments, the TMS protocol is modified based on the determined TMS treatment effect, for example treatment efficacy or treatment side effects. In some embodiments, the TMS protocol modifications are adjusted to increase the TMS treatment efficacy. Alternatively, the TMS protocol modifications are adjusted to reduce TMS side effects, for example pain sensation. In some embodiments the TMS protocol modifications comprise modifying pulse frequency, and/or number of pulses in a train of pulses and/or number of pulses in a treatment session and/or time of a treatment session. Optionally, modifications of the TMS protocol include changing the location of the magnetic coil on the patient's head. In some embodiments, the TMS protocol modifications comprise modifying the duration of each TMS treatment session and/or the time interval between two consecutive treatment sessions.

According to some exemplary embodiments, the modified TMS protocol is used in the next application of the TMS treatment. In some embodiments, microstate parameters values are determined and the TMS effect is determined during a TMS treatment session. In some embodiments, the TMS protocol is modified during a TMS treatment session, based on the determined microstate parameters values and/or based on the determined TMS effect.

According to some embodiments, the TMS treatment is applied, for example, as described in Rutherford G. et al., 2013 or in Theiner P. et al., 2015. In some embodiments, the TMS treatment is directed to at least one brain region, for example prefrontal cortex (PFC), right and/or left dorsolateral prefrontal cortex (DLPFC), Broca, Wernicke, right and/or left parietal somatosensory association cortex (R-pSAC, L-pSAC), ventrolateral prefrontal cortex, inferior frontal gyrus, dorsal parts of supplementary motor cortex, or the cerebellum (Rutherford G. et al., 2013, Theiner P. et al., 2015). Optionally, the TMS is directed to the basal ganglia and/or to medial temporal lobe brain regions and/or to frontal lobe brain regions. In some embodiments, the TMS treatment is applied as a repetitive TMS treatment (rTMS). In some embodiments, the rTMS treatment is a high frequency rTMS in the range of 10-20 Hertz. Alternatively, the rTMS treatment is a low frequency rTMS in the range of 1-9 Hertz. Optionally, the region to be affected by the TMS and/or the parameters of the TMS treatment are determined based on the EEG measurements and/or based on the diagnosis of the disease.

Exemplary Classification

Figure 5B:
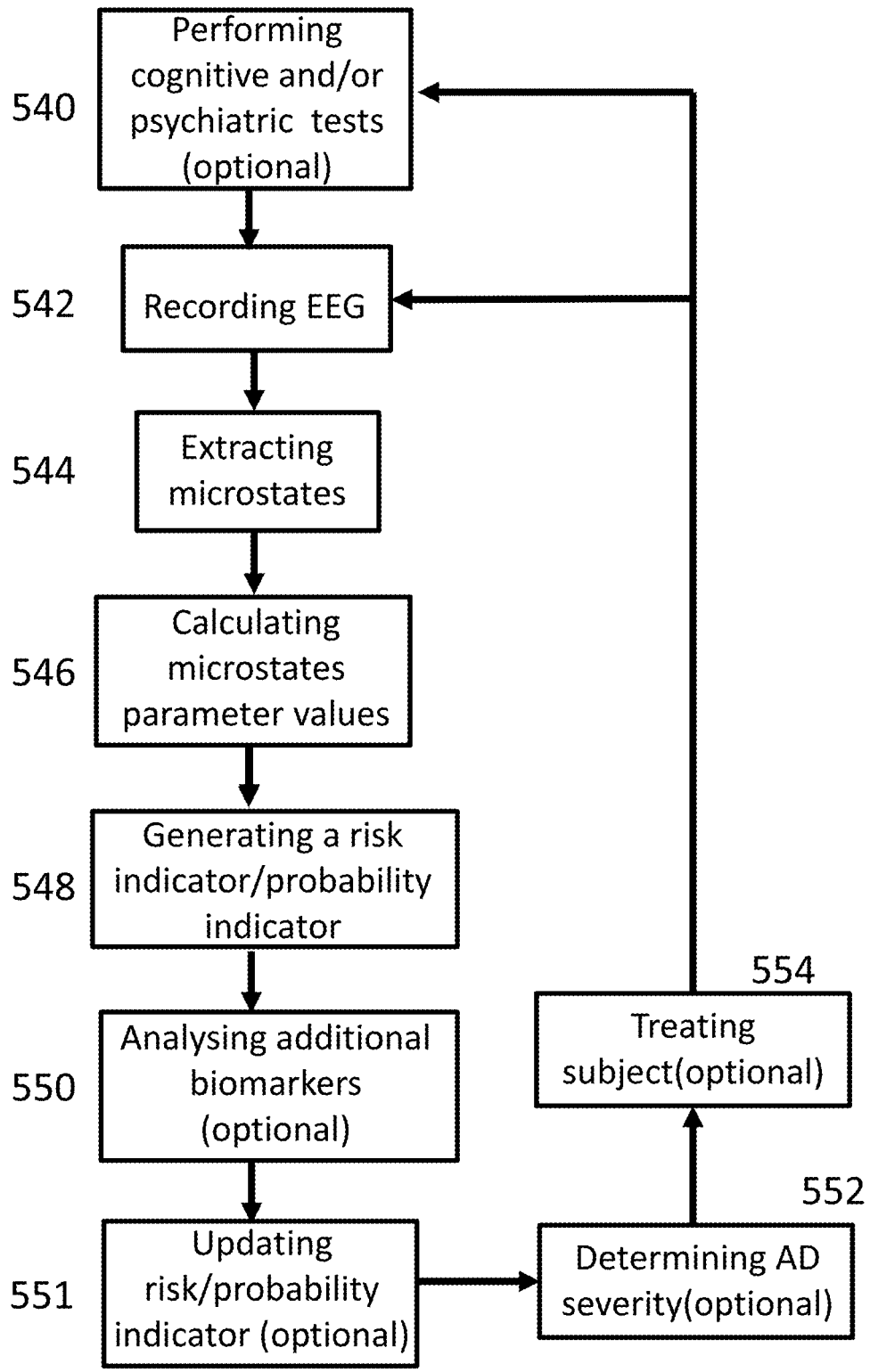

According to some exemplary embodiments, extraction of microstates from EEG recordings, and further analysis of the microstates parameters allows, for example to distinguish between subjects suffering from AD and cognitively normal subjects. In some embodiments, analysis of the extracted microstates parameters allows, for example, to distinguish between subjects suffering from AD and subjects suffering from other neurological or psychiatric pathologies, for example depression. Reference is now made to FIG. 5B, depicting a process for classifying AD subjects, cognitively normal subjects and depressed subjects, according to some exemplary embodiments of the invention.

According to some exemplary embodiments, a subject performs cognitive and/or psychiatric and/or clinical tests at 540. In some embodiments, the cognitive tests comprise Mini-Mental State Exam (MMSE), Mini-cog, Memory Impairment Screen (MIS), Eight-item Information Interview to Differentiate Aging and Dementia (AD8), Alzheimer's Disease Assessment Scale-Cog (ADAS-Cog) and/or other tests that measure disturbances of memory, language, praxis, attention and other cognitive abilities which are often reffered to as the core symptoms of AD. Optionally, cognitive testing devices are used, for example Cantab Mobile, Cognigram, Cognivue, Cognition and Automated Neuropsychological Assessment Metrics (ANAM) devices. In some embodiments, a score for one or more of the tests is stored in a memory, or a database, for example for each subject.

According to some exemplary embodiments, EEG signals are recorded at 542. In some embodiments, EEG signals are recorded by one or more electrodes attached to the scalp of a subject. In some embodiments, EEG signals are recorded as described, for example, at 114 or 102. In some embodiments, EEG is recorded by one or more electrodes, for example 1, 2, 4, 8 electrodes. In some embodiments, EEG signals are recorded, for example by EEG electrodes 406. In some embodiments, the recorded EEG signals are stored in memory 416.

According to some exemplary embodiments, microstates are extracted from the recorded EEG signals at 544. In some embodiments, resting state microstates are extracted from EEG signals recorded when the eyes of a subject are closed. In some embodiments, resting state microstates are determined by analyzing one or more EEG parameters values, and optionally identifying patterns indicating at least one resting state. In some embodiments, microstates are extracted, for example, as previously described at 116. In some embodiments, control circuitry 412 extracts microstates from the stored EEG signals, optionally according to one or more algorithms stored in memory 416. In some embodiments, the extracted microstates are stored in memory 416.

According to some exemplary embodiments, microstates parameter values are calculated at 546. In some embodiments, the parameters values or mean values of resting state microstates are calculated. In some embodiments, microstates parameters comprise duration or means duration of one or more microstates or the combined duration or mean duration of two or more microstates. In some embodiments, the microstates parameters comprise the number of transitions of one or more microstates. In some embodiments, the microstates parameters comprise coverage and/or frequency of one or more microstates or a combination of two or more microstates. In some embodiments, microstates parameters values are calculated as previously described at 180, 120 and/or 122.

According to some exemplary embodiments, microstates parameters comprise one or more of microstate duration, microstate coverage, microstate frequency, number of transitions of each microstate or any combination of the microstates parameters for one or more or a combination of microstates.

According to some exemplary embodiments, control circuitry 412 calculates microstates parameter values, from the stored microstates. In some embodiments, the microstates parameter values are calculated using one or more algorithms stored in memory 416. In some embodiments, the calculated microstates parameter values are stored in memory 416.

According to some exemplary embodiments, a risk indicator or a probability indicator is generated at 548. In some embodiments, the indicator provides an indication for the risk or probability of a subject to be classified in one or more disease stages, for example AD, depression, vascular dementia, MCI, mixed dementia and/or cognitively normal. In some embodiments, the indicator is generated based on one or more of the calculated microstates parameter values or based on a combination of two or more microstates parameter values. In some embodiments, the indicator is generated by control circuitry 412 of device 402. In some embodiments, the indicator is generated based on a combination between the results of cognitive test and/or other clinical test and the calculated microstates parameter values. In some embodiments, the indicator is generated based on calculated microstates parameter values stored in memory 416, and using data tables, data indications and/or one or more algorithms stored in memory 416. Optionally, the indicator is transmitted to a user of device 402 or an expert, for example a physician using interface 414 and/or transmitter 415. In some embodiments, the indicator is transmitted, optionally by wireless communication, to a handheld device of a patient or an expert.

According to some exemplary embodiments, a score is generated for each clinical condition, based on the calculated microstates parameter values at 548. In some embodiments, the score is generated based on the calculated microstates parameter values and the results of cognitive, psychiatric and/or clinical tests performed at 540.

According to some exemplary embodiments, at least one parameter value or a combination of 2 or more parameter values are classified to AD population, cognitively normal population or depressed population at 548. In some embodiments, the classification of the parameter values is determined based on the risk indicator or a combination between the risk indicator and additional biomarkers and/or results of tests. In some embodiments, control circuitry 412 classifies the at least one parameter value or the combination of 2 or more parameter values, optionally using two or more algorithms stored in memory 416. In some embodiments, one or more classifications, tables or indications are stored in a memory or the database, for example memory 416. Optionally, a combined clinical score based on a combination between two or more of the classification, the risk indicator, the cognitive tests is generated. Optionally, the combined clinical score is stored in memory 416.

According to some exemplary embodiments, a subject is classified to one or more clinical condition groups based on the calculated microstates parameter values at 548. In some embodiments, the subject is classified to one or more clinical condition groups based on the calculated microstate parameter values and the results of cognitive, psychiatric and/or clinical tests performed at 540.

According to some exemplary embodiments, additional one or more biomarkers are analysed at 550, for example to identify vascular dementia and/or other types of dementia. Optionally, PET-CT analysis and/or analysis of cerebrospinal fluid (CSF) are performed at 550, for example to evaluate levels of AD biological markers such as A-beta or tau-proteins. In some embodiments, a biomarkers score is generated based on the results of the biomarkers analysis at 550. In some embodiments, the biomarkers score is stored in the memory 416 or the database. In some embodiments, the combined clinical score is updated, optionally by control circuitry 412, based on one or more of the cognitive tests score, the classification and/or the biomarkers score for each subject. In some embodiments, each of the scores is a predictive score that is used to classify a subject as an AD subject, normal subject or depressed subject.

According to some exemplary embodiments, the risk or the probability indicator is updated at 551. In some embodiments, the risk or the probability indicator is updated based on the analysis results of the additional biomarkers. In some embodiments, control circuitry 412 generates an updated indicator. Optionally, the updated indicator is transmitted to a user or an expert by transmitter 415 and or interface 414 of device 402, for example as described above at 548.

According to some exemplary embodiments, the severity of AD is optionally determined at 552. In some embodiments, the severity level of AD, for example MCI, mild-moderate AD, moderate AD, moderate-severe AD or severe AD is determined at 552. In some embodiments, the severity level of AD is determined based on the calculated microstates parameters values at 544. Optionally, AD severity is determined based on the calculated microstates parameters values and the cognitive and/or clinical tests performed at 546. In some embodiments, AD severity is determined based on the risk or probability indicator generated at In some embodiments, AD severity is determined based on the duration of one or more microstates and/or based on the combined duration of two or more microstates. In some embodiments, AD severity is determined or estimated based on one of the combined clinical score, the risk indicator, the classification, the cognitive tests score, the biomarkers score or any combination between the scores. In some embodiments, AD severity is determined by control circuitry 412. In some embodiments, an indication about the classification of a subject and/or the severity of AD is delivered to a user or an expert using interface 414 and/or transmitter 415.

According to some exemplary embodiments, the subject is treated at 554. In some embodiments, a treatment program is selected or adjusted for the treatment of AD. Optionally, the treatment is selected or adjusted to treat a specific AD severity level. In some embodiments, the treatment is selected from a plurality of treatments stored in memory 416.

According to some exemplary embodiments, cognitive tests are performed following the treatment at 540. Optionally, EEG signals are recorded at 542 following the treatment. In some embodiments, EEG signals are recorded one or more hours or one or more days or weeks following the treatment. In some embodiments, the EEG signals are recorded following the treatment, for example to monitor the effect of the treatment on the subject's condition. Optionally, the EEG signals are recorded following the treatment to re-asses the clinical condition of the subject and/or to re-classify the subject.

Exemplary Validation Experiment

Following is a description of an experiment performed using the methods described herein. While the experiment was performed using specific methods, it should be noted that some of the methods and some of the results may be adjusted or used in some embodiments of the invention. The experiment shows that there is a difference between populations and that this difference can be used, for example by using probabilities gleaned from the experimental results, to help classify a new individual, with or without an additional data, for example additional biomarkers or results of cognitive or psychiatric tests.

In the experiment, EEG data and medical records of three cohorts: demented patients (n=68), depressed patients (n=50) and normal controls (n=50), as summarized in FIG. 6A was retrospectively examined.

In the experiment, Dementia was restricted to cases diagnosed with dementia due to Alzheimer disease (AD) or due to mixed pathology (i.e. AD combined with vascular dementia (VD)). Additionally, subjects were divided according to age groups, for example as shown in FIG. 6A.

Figure 6B:
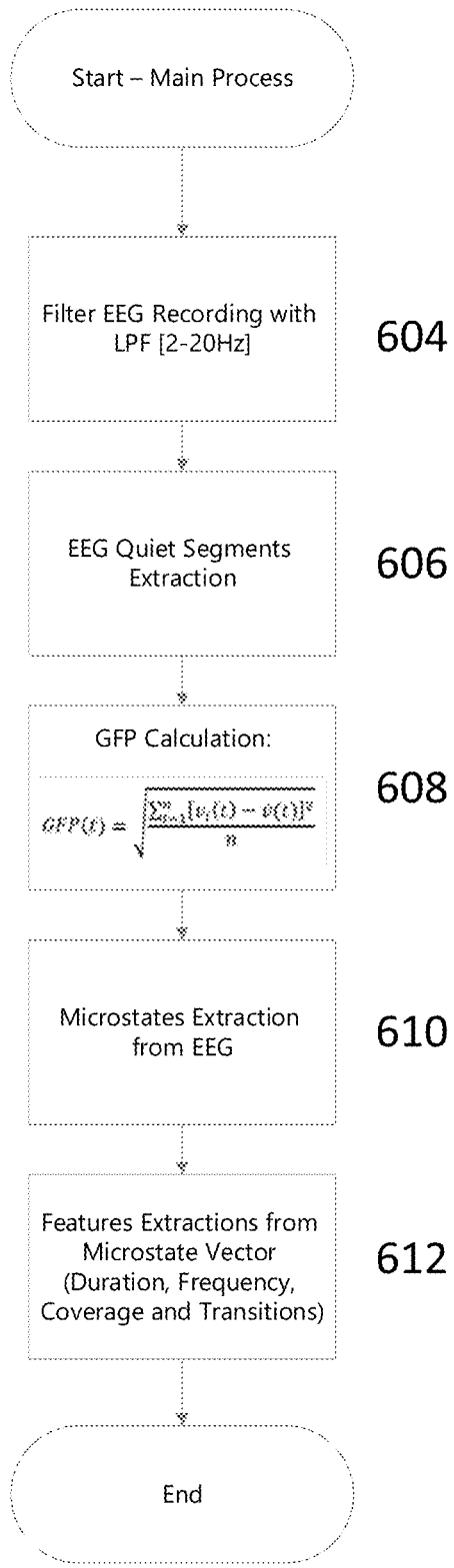

Reference is now made to FIG. 6B depicting a process for extraction of microstates from one or more EEG signals that was used in the experiment and that can also be used is some embodiments of the invention.

In the experiment, EEG signals in a frequency range of 1-40 Hertz were filtered at 604. In some embodiments of the invention, EEG signals in a frequency range of 1-40 Hertz, for example 1-10, 2-20, 2-25 or any intermediate, larger range or smaller. Optionally, in some embodiments of the invention, EEG signals in frequencies larger than 40 Hertz and/or smaller than 1 Hertz are filtered.

Quiet segments in the filtered EEG signals were extracted at 606. In the experiment and in some embodiments of the invention, quiet segments are segments where the EEG signals are resting state EEG signals. In the experiment and in some embodiments of the invention, quiet segments are segments in the EEG recorded when the eyes of a subject are closed. In the experiment, all EEG signals were resting state EEG. The relevant segments used for microstate extraction were those segments when eyes were closed. In the experiment, an algorithm extracted those segments when alpha rhythm appears (i.e eyes closed), for example for automatically extraction of microstates. In some embodiments of the invention, as used in the experiment, quiet segments are identified and optionally extracted based on the detection of an alpha rhythm. Optionally, in some embodiments of the invention, detection of an alpha rhythm and/or extraction of the quiet segments are performed by one or more algorithms, for example one or more algorithms stored in a memory.

In some embodiments of the invention, the presence and/or levels of the alpha rhythm is monitored, optionally continuously monitored. In some embodiments, the presence and/or levels of the alpha rhythm are monitored during a specific time period, for example during a time period between 1 minute and 60 minute, or any other larger or smaller time period. In some embodiments, when the levels of the alpha rhythm are higher than a predetermined level the EEG signals are recorded and optionally are classified as resting state EEG signals. In some embodiments of the invention, a system monitors the eyes closure rate, or any other clinical or physiological parameter indicative of a resting state.

In the experiment, GFP was calculated at 608. In the experiment and in some embodiments, the GFP is calculated, as described in the "Exemplary microstates extraction" section of this application.

In the experiment, microstates were extracted from the filtered EEG signals at 610. In the experiment and in some embodiments of the invention the microstates are extracted, as described in the "Exemplary microstates extraction" section of this application. In the experiment, the microstates comprise microstate A, microstate B, microstate C and/or microstate D. In some embodiments of the invention, the microstates comprise one or more of microstate A, microstate B, microstate C and/or microstate D or any number of defined microstates, for example the number of microstates or the definition of each microstate is personalized to a specific subject and/or to a specific clinical condition.

In the experiment, microstates parameters, also termed herein as "features" were extracted from the microstate vector at 612. In the experiment and in some embodiments of the invention the microstates parameters are extracted, as described in the "Exemplary microstates extraction" section of this application. In the experiment and in some embodiments of the invention, the features comprise one or more of microstate duration, microstate frequency, microstate coverage and microstate transitions or any mathematical derivation of the features, for example a mean of the features.

In some embodiments of the invention, one or more microstates, for example microstate A and/or microstate B and/or microstate C and/or microstate D are extracted from an EEG signal. In some embodiments, values of one or more microstates parameters are calculated, for example microstate duration and/or microstate frequency and/or microstate coverage and/or number of transitions of one or more microstates or any mathematical derivation of the values, for example a mean or an average.

Figure 7:
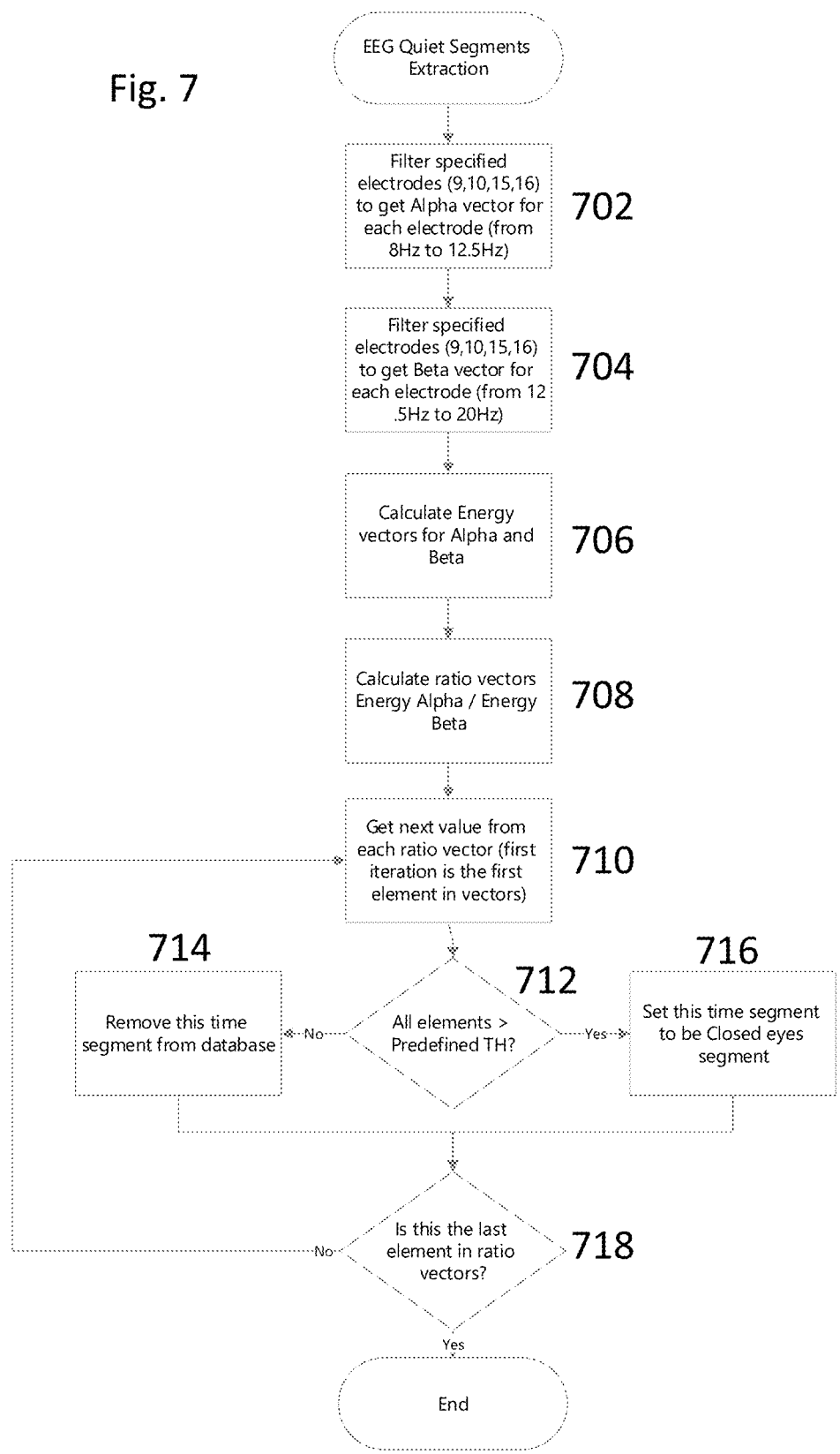

Reference is now made to FIG. 7, depicting a process that was used in the experiment and that can also be used in some embodiments of the invention for extraction of EEG quiet segments.

In the experiment, EEG signals were filtered from a desired number of electrodes to get an Alpha vector for each electrode at 702. Optionally, in some embodiments of the invention, EEG signals from 8, 9, 10, 15 16 or any desired number of electrodes are filtered. In the experiment, an Alpha vector was received by filtering EEG signals in a range of 8 Hertz to 12.5 Hertz. Optionally, in some embodiments of the invention an alpha vector is received in a different range of frequencies, for example a range of frequencies that is personalized for a specific subject or to a specific clinical condition.

In the experiment, EEG signals were filtered from a desired number of electrodes to get a Beta vector for each electrode at 704. Optionally, in some embodiments of the invention, EEG signals from 8, 9, 10, 15 16 or any desired number of electrodes are filtered. In some embodiments, a beta vector was received by filtering EEG signals in a range of 12.5 Hertz to 20 Hertz. Optionally, in some embodiments of the invention a beta vector is received in a different range of frequencies, for example a range of frequencies that is personalized for a specific subject or to a specific clinical condition.

In the experiment, energy vectors for Alpha and/or Beta vectors were calculated at 706. A ratio between Alpha energy vectors and Beta energy vectors was calculated at 708.

In the experiment, the next value from each ratio vector is calculated (first iteration is the first element in vectors) at 710. If all elements are larger than a predefined threshold as checked at 712, the specific analysed time segment was set to be a closed eyes segment at 716.

In the experiment, if all elements were not larger than a predefined threshold as checked at 712, then the specific analysed time segment was removed at 714. Optionally, in some embodiments of the invention, a specific analysed time segment is removed from a database of signals, for example a database of signals that is used for further analysis of the EEG signals.

In the experiment, if this was not the last element in the ratio vectors as checked at 718, then the next value from each ratio vector was calculated at 710.

Reference is now made to FIG. 8 depicting a process for microstates extraction as used in the experiment and that can also be used in some embodiments of the invention. In the experiment, the microstates were extracted from quiet segments of the EEG signal, for example from closed eyes segments of the EEG signal. Optionally, in some embodiments of the invention, the microstates are extracted from closed time segments stored in a database of time segments.

In the experiment, peaks in the GFP vector were detected at 802. Optionally, in some embodiments of the invention, only selected peaks in the GFP vector, for example peaks that are larger than a predefined threshold are detected. EEG vector value at each GFP peak was extracted at 804. Optionally, in some embodiments of the invention, EEG vector values at selected GFP peaks are extracted.

In the experiment, the number of clusters was set to k=4 at 806. In addition, constant seed for k-means classification was set at 808.

In the experiment, a centroid of clusters (k centers) was detected at 810. Optionally, first iteration is centroid=seed.

In the experiment, a correlation of all objects to the centroid was calculated at 812. Optionally, in some embodiments of the invention, a correlation of selected objects to the centroid is calculated.

In the experiment, one or more objects were grouped based on maximum correlation at 814.

In the experiment, a check was performed to determine if objects moved at 816.

In the experiment, if objects did not move then the process was ended at 818.

In the experiment, if objects moved, then a centroid of clusters (k centers) was found as previously described at 810.

Reference is now made to FIG. 9, depicting a process for extraction of microstates duration as used in the experiment and that can also be used in some embodiments of the invention.

In the experiment, the first state in the vector was detected at 904. Additionally, the next different state was detected at 906. In the experiment, the duration of the state appearance was saved at 908. A check was performed to determine if this is the end of the vector at 910.

In the experiment, if this was not the end of the vector, then the process moved to the next different state at 906. In the experiment, if this was end of the vector, then the mean appearance time of each microstate was calculated at 912. Additionally, the standard deviation of each microstate is calculated at 914.

Reference is now made to FIG. 10, depicting a process for extraction of microstates transition as used in the experiment and that can also be used in some embodiments of the invention.

In the experiment, all transition counters (from state to state) were set to 0 at 1002. In the experiment, all 12 transition counters were set to 0. The first state in the vector was detected at 1004. The next different state was detected at 1006. Then, the transition counter was increased by 1 at 1008.

In the experiment, a check was performed to determine if this was the end of the vector at 1010. If this was the end of the vector, then the percentage of each transition type was calculated at 1012. If this was not the end of the vector then the process moved to the next different state at 1006.

Reference is now made to FIG. 11, depicting a process for extraction of microstates coverage as used in the experiment and that can also be used in some embodiments of the invention.

In the experiment, the number of appearances of each microstate was counted at 1102. The fraction of the total appearance of each microstate in the microstates vector was calculated. Optionally the percentage of the total appearance of each microstate in the microstates vector was calculated.

Reference is now made to FIG. 12, depicting a process for extraction of microstates frequency as used in the experiment and that can also be used in some embodiments of the invention.

In the experiment, the microstates vector was split to equal segments of time, for example to segments of 1 second at 1202. The number of states appearances at each segment was counted at 1204. Then, the mean appearance of each microstate at all the time segments was calculated at 1206. Additionally, the standard deviation of appearance of each microstate at all time segments was calculated at 1208.

In the experiment, the EEG data was processed using the methods described in FIGS. 6B-12. Optionally, the EEG was processed using a computerized algorithm. The algorithm received EEG data, performed EEG noise reduction and optionally subtracted microstates from the EEG. In the experiment, the microstates were subtracted using one of two clustering methods which were termed "seed" or "retries". Additionally, the algorithm defined the microstate type (A, B, C or D) and its characteristic parameters (duration, coverage, frequency and transition). In some embodiments of the invention, the algorithm and/or the clustering methods described herein are used.

In the experiment, statistical analysis was performed using Statistical Package for the Social Sciences (SPSS). A comparison of microstate parameters between groups was accomplished using t test for two groups' comparisons and/or using analysis of variation (ANOVA) for multiple group comparisons. The statistical significant difference was defined as a two tailed P level less than 0.05.

In the experiment, all EEG data was processed using a computerized algorithm. Due to low EEG acquisition quality 5, 9 and 13 subjects from the demented, depressed and normal group were excluded respectively. After exclusion there were 55 demented patients, 41 depressed patients and 40 normal controls.

In the experiment, using the "retries" clustering method a significant difference between the three cohorts in the duration of states A, B and D ($p=0.004$, $p=0.04$ and $p=0.006$ respectively) was observed. A significant difference was also noticed in the frequency of state B and C ($p=0.037$ and $p=0.049$, respectively). Comparing only the depressed cohort to normal controls demonstrated a significant difference in the duration of state D ($p=0.048$). Comparing only demented patients to the normal controls yielded a significant difference in the coverage of state A ($p=0.02$), duration of states A, B and D ($p=0.002$, $p=0.016$ and $p=0.002$ respectively) and transitions of state A ($p=0.04$).

In the experiment, using the "seed" clustering method a significant difference was demonstrated between the three groups in the duration of states C and D ($p=0.037$ and $p=0.015$ respectively). Comparing only the depressed cohort to normal controls demonstrated a significant difference in the duration of states A ($p=0.009$), B ($p=0.011$), C ($p=0.016$), D ($p=0.006$) and in the frequencies of states A ($p=0.048$), B (0.024) and D ($p=0.044$). Comparing duration of all states grouped together there was a significant difference between the demented patients and the normal controls ($p=0.002$), for example as shown in FIG. 13.

In order to further explore whether dementia severity influences microstate parameters, the medical records of Alzheimer's disease demented patients who had performed a complete cognitive evaluation (n=25) was examined. These patients were divided into 2 groups: those with very mild dementia (n=6) vs. those having mild-moderate dementia (n=19). There was a significant difference in microstate duration between the two groups ($p=0.006$).

In addition, a comparison was made between 6 groups of subjects: demented subjects (DEM, Type 10), AD subjects (AD, Type 11), MILD dementia subjects (MILD, Type 12), Vascular dementia subjects (VD, Type 13), Depressed subjects (DEP, Type 20), and cognitively normal subjects (NORM, Type 30). The mean duration in each microstate of each group was calculated, as shown in Table 1. The demented subjects (DEM, Type 10) comprised demented subjects diagnosed with dementia without a complete cognitive evaluation. Additionally, this group also comprises subjects with mixed dementia (AD+vascular dementia). AD subjects (AD, Type 11) comprised patients diagnosed with AD after a complete cognitive evaluation. Mild dementia subjects (MILD, Type 12) comprised subjects diagnosed with MCI, optionally very mild dementia. Vascular dementia subjects (VD, Type 13) comprised subjects diagnosed with vascular dementia and/or mixed dementia.

In the experiment, a pairwise comparison was performed, for example as shown in Table 2, between the mean duration in all microstates of two groups, for example to test whether it is possible to use the mean duration as a parameter for distinguishing between 2 or more groups. In some embodiments of the invention, classification is performed, for example as described in FIG. 5B based on the mean duration parameter, as described in the experiment.

In the experiment, a pairwise comparison between AD subjects and mild dementia (MCI), depressed or cognitively normal subjects resulted with a statistically significant mean difference. A pairwise comparison between mild dementia (MCI) subjects and AD or VD resulted with a statistically significant mean difference. A pairwise comparison between VD and DEM, MILD, DEP OR NORM resulted with a statistically significant mean difference. A pairwise comparison between depressed subjects (DEP) and AD or VD resulted with a statistically significant mean difference. In some embodiments of the invention, distinguishing between AD, VD and depressed subjects, for example based on the mean duration as described in the experiment, allows to better classify a clinical condition of a subject that may present similar cognitive and/or behavioral symptoms that are shared between AD, VD and depression.

In the experiment, a pairwise comparison between cognitively normal subjects (NORM) and AD or VD resulted with a statistically significant mean difference. The statistically significant differences between the different groups are used in some embodiments of the invention to generate a score for each clinical condition, for example AD, VD, NORM, MCI or depression. In some embodiments of the invention, the statistically significant differences between the groups are used to calculate a risk indicator which indicates a probability of a subject to be classified in one or more of the groups, for example as described in FIG. 5B. Additionally or alternatively, in some embodiments of the invention the statistically significant difference between the groups is used for classifying a subject condition in one or more of the groups which are associated with a clinical condition.

In the experiment, a scatter plot of the mean duration of microstates for each subject in each group was generated, for example as shown in FIG. 14. As demonstrated in the scatter plot, more than 97% of the cognitively normal subjects (NORM, 1412) have a mean duration which is smaller than 0.07 seconds. On the other hand, more than 30% of AD subjects (AD, 1404) have a mean duration larger than 0.07 sec. In addition, more than 16% of the depressed subjects (DEP, 1410) have a mean duration larger than 0.07 sec, and more than 84% have a mean duration smaller than 0.07 sec.

In some embodiments of the invention and as described in the results of the experiment, based on a pre-determined threshold, for example 0.07 sec or any other threshold, the probability of a subject to be classified in one or more clinical conditions groups is determined, for example groups DEM (1402), AD (1404), MILD (1406), VD (1408), DEP (1410) and NORM (1412) used in the experiment. Optionally a probability score is calculated, for example based on the mean duration as shown in FIG. 14.

In some embodiments of the invention, based on FIG. 14, the results of the experiment, or any conversion table between a calculated microstates parameter values and a clinical condition, a probability score or a risk indicator is determined, optionally based on a predefined threshold or a predefined range of values. For example, based on the results of the experiment, if a subject has a mean duration higher than 0.07 sec, then he has a probability of 16% to be classified as depressed, a probability of 32% to be classified as an AD, and a probability of 40% to be classified as VD. If a subject has a mean duration larger than 0.08 sec, then he has a probability of 2% to be classified as depressed, a probability 30% to be classified as VD, and a probability of 10% to be classified as AD.

In some embodiments of the invention, a probability score or a risk indicator is generated, for example as shown in FIG. 5B, based on an association between at least one parameter value of the microstates and a stored table, a stored database, stored indications and/or one or more stored algorithms. In some embodiments, the generated score comprises the probability of a subject to be associated with 2 or more groups, for example the groups discussed above. In some embodiments, the probability score or the risk indicator are generated using a conversion table between microstates parameter values and one or more clinical conditions, stored in a memory or a remote database or a remote server.

In some embodiments, a remote server is used in order to build a database of indication or one or more conversion tables between microstates parameter values and one or more clinical conditions. In some embodiments, the remote server generates the database of indications or the one or more conversion tables using machine learning techniques, one or more algorithms and/or using neural networks.

In some embodiments, in order to classify a patient an association between one or more microstates parameter values and one or more clinical conditions is performed in the remote server.

TABLE 1

Descriptive Statistics

| | Type | Mean | Std. Deviation | N |
|---|---|---|---|---|
| meanDur_A | 10 | .05753 | .011097 | 16 |
| | 11 | .06181 | .015172 | 28 |
| | 12 | .05142 | .005631 | 6 |
| | 13 | .06473 | .014153 | 10 |
| | 20 | .05649 | .008819 | 42 |
| | 30 | .05390 | .006616 | 40 |
| | Total | .05729 | .010896 | 142 |
| meanDur_B | 10 | .05709 | .011462 | 16 |
| | 11 | .06005 | .011436 | 28 |
| | 12 | .04867 | .003507 | 6 |
| | 13 | .06481 | .011912 | 10 |
| | 20 | .05729 | .009752 | 42 |
| | 30 | .05360 | .005659 | 40 |
| | Total | .05694 | .009872 | 142 |
| meanDur_C | 10 | .05704 | .010260 | 16 |
| | 11 | .06439 | .018785 | 28 |
| | 12 | .04931 | .002495 | 6 |
| | 13 | .06294 | .015663 | 10 |
| | 20 | .05782 | .009478 | 42 |
| | 30 | .05424 | .009222 | 40 |
| | Total | .05802 | .012707 | 142 |
| meanDur_D | 10 | .05636 | .010517 | 16 |
| | 11 | .05975 | .011517 | 28 |
| | 12 | .05087 | .003233 | 6 |
| | 13 | .06884 | .015370 | 10 |
| | 20 | .05620 | .007760 | 42 |
| | 30 | .05336 | .005710 | 40 |
| | Total | .05678 | .009805 | 142 |

TABLE 2

Pairwise Comparisons

Measure: MEASURE_1

| (I) Type | (J) Type | Mean Difference (I−J) | Std. Error | Sig[b] | 95% Confidence Interval for Difference[b] | |
|---|---|---|---|---|---|---|
| | | | | | Lower Bound | Upper Bound |
| 10 | 11 | −.004 | .003 | .119 | −.010 | .001 |
| | 12 | .007 | .004 | .115 | −.002 | .016 |
| | 13 | −.008* | .004 | .025 | −.016 | −.001 |
| | 20 | 5.607E−5 | .003 | .983 | −.005 | .005 |
| | 30 | .003 | .003 | .234 | −.002 | .009 |
| 11 | 10 | .004 | .003 | .119 | −.001 | .010 |
| | 12 | .011* | .004 | .006 | .003 | .020 |
| | 13 | −.004 | .003 | .257 | −.010 | .003 |
| | 20 | .005* | .002 | .043 | .000 | .009 |
| | 30 | .008* | .002 | .001 | .003 | .012 |
| 12 | 10 | −.007 | .004 | .115 | −.016 | .002 |
| | 11 | −.011* | .004 | .006 | −.020 | −.003 |
| | 13 | −.015* | .005 | .002 | −.025 | −.006 |
| | 20 | −.007 | .004 | .087 | −.015 | .001 |
| | 30 | −.004 | .004 | .356 | −.012 | .004 |
| 13 | 10 | .008* | .004 | .025 | .001 | .016 |
| | 11 | .004 | .003 | .257 | −.003 | .010 |
| | 12 | .015* | .005 | .002 | .006 | .025 |
| | 20 | .008* | .003 | .010 | .002 | .015 |
| | 30 | .012* | .003 | .000 | .005 | .018 |
| 20 | 10 | −5.607E−5 | .003 | .983 | −.005 | .005 |
| | 11 | −.005* | .002 | .043 | −.009 | .000 |
| | 12 | .007 | .004 | .087 | −.001 | .015 |
| | 13 | −.008* | .003 | .010 | −.015 | −.002 |
| | 30 | .003 | .002 | .118 | −.001 | .007 |
| 30 | 10 | −.003 | .003 | .234 | −.009 | .002 |
| | 11 | −.008* | .002 | .001 | −.012 | −.003 |
| | 12 | .004 | .004 | .356 | −.004 | .012 |
| | 13 | −.012* | .003 | .000 | −.018 | −.005 |
| | 20 | −.003 | .002 | .118 | −.007 | .001 |

Based on estimated marginal means
*The mean difference is significant at the .05 level.
[b]Adjustment for multiple comparisons: Least Significant Difference (equivalent to no adjustments).

Further Experimental Data

Further to the above experiment additional patients were requited, leading to the following total of 204 patients, of which:

(a) 118 Alzheimer's disease patients (ALZ), of which 54 are at an MCI stage (MCI) and 64 with dementia (DEMETIA). Of these 64 dementia patients, 10 were diagnosed with pre-senile dementia (onset before age 65). Of these 118 patients, 112 received a complete cognitive evaluation.

(b) 44 patients with depression (DEP)

(c) 42 patients assessed as normal, as a control group (NOR).

EEG signals were acquired from each patient and analyzed, for example, as described above with respect to the Experiment, including, for example, identification of quiet sections.

The data was analyzed to determine microstate parameters who values may be used to predict and/or quantify disease state. As shown, below, at least mean duration and mean frequency can be used. These are only exemplary and other statistics of the states may be used as well, for example, microstate coverage, microstate transitions and microstate percentage. Optionally, such data is used when training a machine-learning type classifier. Also, mean duration and mean frequency may be modified in some embodiments, for example, to drop outliers. Optionally, data from all microstates is combined. Alternatively, data form only some microstates is used and/or data from the different microstates used to train or otherwise build a classifier.

It is noted that the data from this further experiment includes and therefore may statistically supersede the data in tables 1 and 2.

FIG. 15A is a chart showing the differences in mean duration of different types of microstates, for various cognitive disease states, in accordance with exemplary embodiments of the invention.

FIG. 15B is a chart showing the differences in mean frequency (e.g., by taking all the type A microstates (though others could be selected) and calculating the average frequency (e.g., as number of occurrences per second) of these microstates for all subjects in a group) of different types of microstates, for various cognitive disease states, in accordance with exemplary embodiments of the invention.

FIG. 16A is a table showing pairwise comparisons for mean duration between the groups of patients with the different cognitive disease states, indicating statistical significance, in accordance with some embodiments of the invention.

FIG. 16B is a table showing pairwise comparisons for mean frequency between the groups of patients with the different cognitive disease states, indicating statistical significance, in accordance with some embodiments of the invention.

The following table shows statistical properties of duration for various microstates:

| Descriptive Statistics | | | | |
|---|---|---|---|---|
| | Group | Mean | Std. Deviation | N |
| meanDur_A | ALZ | .05824394447 | .01165392512 | 118 |
| | DEP | .05623071566 | .00891104649 | 44 |
| | NOR | .05391533339 | .00666908995 | 42 |
| | Total | .05691853401 | .01034745804 | 204 |
| meanDur_B | ALZ | .05749331500 | .00876178744 | 118 |
| | DEP | .05650752106 | .00875885124 | 44 |
| | NOR | .05358182077 | .00557914223 | 42 |
| | Total | .05647538514 | .00831373241 | 204 |
| meanDur_C. | ALZ | .05864313021 | .01304081187 | 118 |
| | DEP | .05761068774 | .00939489461 | 44 |
| | NOR | .05378801154 | .00894238050 | 42 |
| | Total | .05742086329 | .01168205249 | 204 |
| meanDur_D | ALZ | .05655127747 | .00885704348 | 118 |
| | DEP | .05604575080 | .00795997906 | 44 |
| | NOR | .05326524464 | .00571326637 | 42 |
| | Total | .05576570614 | .00817903878 | 204 |

The following table shows statistical properties of frequency for various microstates:

| Descriptive Statistics | | | | |
|---|---|---|---|---|
| | Group | Mean | Std. Deviation | N |
| meanFreq_A | ALZ | 2.44695 | 1.815636 | 118 |
| | DEP | 2.89414 | 1.835563 | 44 |
| | NOR | 3.67781 | 2.871810 | 42 |
| | Total | 2.79681 | 2.124421 | 204 |
| meanFreq_B | ALZ | 2.48092 | 1.875337 | 118 |
| | DEP | 2.70077 | 1.687730 | 44 |
| | NOR | 3.68857 | 2.726098 | 42 |
| | Total | 2.77697 | 2.086970 | 204 |

-continued

| | Descriptive Statistics | | | |
|---|---|---|---|---|
| | Group | Mean | Std. Deviation | N |
| meanFreq_C | ALZ | 2.48336 | 1.933527 | 118 |
| | DEP | 2.83768 | 1.874226 | 44 |
| | NOR | 3.51886 | 2.443984 | 42 |
| | Total | 2.77297 | 2.066384 | 204 |
| meanFreq_D | ALZ | 2.31385 | 1.744826 | 118 |
| | DEP | 2.89968 | 2.060909 | 44 |
| | NOR | 3.40481 | 2.347479 | 42 |
| | Total | 2.66481 | 1.991028 | 204 |

As can be seen, there is a significant separation between the ALZ group and the NOR group using either one of the duration and frequency parameters.

MCI Separation

The ALZ group was divided into two for analysis purposes: MCI & DEMENTIA, and the analysis repeated.

FIG. 17A is a chart showing the differences in mean duration of different types of microstates, for various cognitive disease states, including mild cognitive impairment (MCI), in accordance with exemplary embodiments of the invention.

FIG. 17B is a chart showing the differences in mean frequency of different types of microstates, for various cognitive disease states, including mild cognitive impairment (MCI), in accordance with exemplary embodiments of the invention.

FIG. 18A is a table showing pairwise comparisons for mean duration between the groups of patients with the different cognitive disease states including MCI, indicating statistical significance, in accordance with some embodiments of the invention.

FIG. 18B is a table showing pairwise comparisons for mean frequency between the groups of patients with the different cognitive disease states including MCI, indicating statistical significance, in accordance with some embodiments of the invention.

The following table shows statistical properties of duration (in seconds) for various microstates:

| | Descriptive Statistics | | | |
|---|---|---|---|---|
| | Group | Mean | Std. Deviation | N |
| meanDur_A | Demented | .06053202588 | .01315569960 | 64 |
| | DEP | .05623071566 | .00891104649 | 44 |
| | MCI | .05553214428 | .00895955550 | 54 |
| | NOR | .05391533339 | .00666908995 | 42 |
| | Total | .05691853401 | .01034745804 | 204 |
| meanDur_B | Demented | .05934177456 | .00940142939 | 64 |
| | DEP | .05650752106 | .00875885124 | 44 |
| | MCI | .05530254810 | .00744253994 | 54 |
| | NOR | .05358182077 | .00557914223 | 42 |
| | Total | .05647538514 | .00831373241 | 204 |
| meanDur_C | Demented | .06161981181 | .01527220929 | 64 |
| | DEP | .05761068774 | .00939489461 | 44 |
| | MCI | .05511521129 | .00864829013 | 54 |
| | NOR | .05378801154 | .00894238050 | 42 |
| | Total | .05742086329 | .01168205249 | 204 |
| meanDur_D | Demented | .05813000615 | .00992005363 | 64 |
| | DEP | .05604575080 | .00795997906 | 44 |
| | MCI | .05468019164 | .00704445436 | 54 |
| | NOR | .05326524464 | .00571326637 | 42 |
| | Total | .05576570614 | .00817903878 | 204 |

The following table shows statistical properties of frequency for various microstates:

| | Descriptive Statistics | | | |
|---|---|---|---|---|
| | Group | Mean | Std. Deviation | N |
| meanFreq_A | Demented | 2.31750 | 1.658776 | 64 |
| | DEP | 2.89414 | 1.835563 | 44 |
| | MCI | 2.60037 | 1.990562 | 54 |
| | NOR | 3.67781 | 2.871810 | 42 |
| | Total | 2.79681 | 2.124421 | 204 |
| meanFreq_B | Demented | 2.42641 | 1.874757 | 64 |
| | DEP | 2.70077 | 1.687730 | 44 |
| | MCI | 2.54552 | 1.891558 | 54 |
| | NOR | 3.68857 | 2.726098 | 42 |
| | Total | 2.77697 | 2.086970 | 204 |
| meanFreq_C | Demented | 2.39738 | 1.860615 | 64 |
| | DEP | 2.83768 | 1.874226 | 44 |
| | MCI | 2.58526 | 2.029382 | 54 |
| | NOR | 3.51886 | 2.443984 | 42 |
| | Total | 2.77297 | 2.066384 | 204 |
| meanFreq_D | Demented | 2.15400 | 1.605812 | 64 |
| | DEP | 2.89968 | 2.060909 | 44 |
| | MCI | 2.50330 | 1.894230 | 54 |
| | NOR | 3.40481 | 2.347479 | 42 |
| | Total | 2.66481 | 1.991028 | 204 |

As can be seen, for the duration microstate parameter there is a significant difference between DEMENTED and NOR, MCI and DEP.

As can be seen, for the frequency microstate parameter there is a significant difference between DEMENTED and NOR and also between MCI and NOR.

In some exemplary embodiments of the invention, mean frequency (alone and/or with other information) is used to determine if a patient should be classified as NOR or as MCI or DEM. Optionally, mean duration and/or other information are used to confirm a NOR classification.

If mean frequency indicated MCI or DEM, mean duration and/or other information are used optionally to increase reliability and/or distinguish between classification as one group or the other.

In some exemplary embodiments of the invention, classification is not certain enough to assign to any group. Optionally, a threshold (e.g., quality of match) for such classification or classification failure is defined.

It is noted that the above results indicated that mean duration of microstate D is not significantly different from the mean duration of other microstates. In some embodiments, this is used as a classification guide. In others, mean duration of microstate D is assumed to be smaller in a significant manner than other microstate durations.

Comparison to Cognitive Tests

In accordance with some embodiments of the invention, microstate data is used together with standard cognitive tests. Optionally, the tests are used in a standard manner.

In some exemplary embodiments of the invention, however, a correlation between standard tests and microstate-derived information is used in a synergistic manner. This may be a result of a correlation between microstate data and results of cognitive tests. Such correlation may, for example, allow (a) microstate data and cognitive tests results to be combined; (b) less and/or more focused microstate data to be acquired; and/or (c) less and/or more focused cognitive test data to be acquired.

In one example, if microstate and non-microstate data support the same diagnosis, then treatment may be provided according to the diagnosis.

In case of discrepancy, the doctor may have more flexibility to decide on starting treatment and/or what type of treatment and/or treatment parameters.

In some cases, for example, if state data is not conclusive, additional EEG and microstate data may be acquired.

If the cognitive or other tests appear conclusive, less microstate data may be collected, for example, in an amount sufficient to support the non-EEG diagnosis. If the microstate data supports a certain diagnosis, a shorter cognitive assessment may be used. For example, for MCI and DEM, the minimental test may be used, possibly with a word memory test and/or MOCA. Optionally, the SAGE or other physician-free questionnaires are used, optionally instead of any human administered cognitive tests, this may allow for faster screening.

If the EEG data analysis conflicts with cognitive diagnosis, a physician may order more in depth testing.

An experiment was performed to compare microstate data to cognitive test data. The MMSE test (which tests time orientation, memory, executive functions, language functions, spatial orientation, and other cognitive abilities) was compared to mean duration. The highest (best) MMSE score is 30. Less than 24 points is usually considered as a marker to dementia. 24 points or above is a marker to MCI or normal cognitive functions.

FIG. 19 is a chart showing a relationship between cognitive tests and cognitive assessment using microstates, in accordance with some embodiments of the invention, in which patients with MCI and DEM are marked both with respect to MMSE score and with respect to mean duration. It is noted that a better classifier (such as using a combination of mean duration and mean frequency and/or other data, may result in a better correlation.

In this chart, the vertical dashed line was set according to the mean duration of the NOR group plus one standard deviation, i.e., 0.053638+0.005555=0.059193 seconds. This is based on the general observation that (for a 1D classifier based on mean duration), higher values of mean duration are correlated with a more degraded cognitive state. Other ways of setting this separation (e.g., as a classifier) may be used, including using a non-straight line or a plane (for 2D or higher data, such as a combination of mean duration and mean frequency).

The horizontal line is set at 24, which is the recognized typical separation between MCI and DEM patients (other values may be used for other tests). The inclined line is a linear regression. Other, more sophisticated regressions may be used.

As can be seen, there is a good correlation between mean duration values and MMSE scores. While this validates the EEG microstate analysis described herein, these results may also be used to guide data collection.

In some exemplary embodiments of the invention, if a patient is borderline using one test (mean duration or MMSE) the other test may be carried out and possibly allow the diagnosis to move away from the border. The two tests may be carried out together as matter of course. However, as noted herein, the microstate test may be simpler and/or faster to administer.

In some exemplary embodiments of the invention, MMSE values of 26 suggest that EEG analysis confirms the diagnosis of MCI. In another example MMSE score of 26 suggests MCI but microstates duration suggest dementia. This warrants further cognitive evaluation for diagnosis. In this example dementia was diagnosed and treatment was started.

Exemplary Diagnosis and/or Treatment for Dementia & MCI

FIG. 20 is a flowchart of a method of diagnosing and optionally treating MCI, in accordance with some embodiments of the invention.

At 2002, one or more non-EEG tests (e.g., cognitive, observational, psychiatric and/or biological, for example as noted in the background of the application) are optionally performed on a patient. In some cases, the test results are up to date. In some cases, test results from previous times, for example, 1-4 weeks or months in the past, or earlier, may be used.

At 2004-2008, EEG data may be collected and analyzed, for example as described herein, for example, at rest. Optionally, a classifier which combines duration based data and frequency based data and/or other data, is optionally used.

At 2010, the patient may be classified as MCI, for example, based on the classifier and/or other data, for example, as provided in 2002, for example, a clinical phenotype.

In some embodiments, the patient is under continued care and may already have been diagnosed as having, for example, dementia, MCI, being normal and/or having some other cognitive problem. Previous treatment may already have started. Repeated testing, for example, as described in FIG. 20 may be performed periodically (e.g., on a time scale of 1-400 days, for example, between 1-10 days, between 10 and 50 days and/or between 50-400 days, or intermediate time scales), before and/or in response to treatment (e.g., an acute treatment such as cognitive training) and/or in response to a desired to change treatment (e.g., a long term treatment such as medication) (e.g., due to a side effect, perceived effectiveness and/or perceived ineffectiveness). In some exemplary embodiments of the invention, testing is repeated before and after treatment, optionally in a short time period, for example, within 0.5-72 hours, for example, between 1 and 5 hours. for some treatment types, testing may be repeated during treatment (e.g. during breaks in a TMS sequence, for example, every 10-60 minutes, for example, every 30 minutes)

FIG. 19 shows that when mean duration is shorter (e.g., less than 0.58) the patient is more likely to be MCI and not DEM. In general, if the microstate data does not match standard assessment, this may suggest that more investigation is needed. For example, a result in the upper right or lower left quadrants of FIG. 19 may indicate need for additional testing, such as a broad cognitive testing, brain MRI, amyloidal testing and/or imaging, and/or PET and/or SPECT testing (e.g., with tagged glucose or Tc or Tau).

At 2012, if the patient is classified or otherwise identified as an MCI patient, treatment may be selected.

At 2016, the treatment is optionally applied.

Testing may be repeated to detect an effect of treatment. For example, a TMS treatment may be considered successful if it changes (e.g., within 0-10 seconds, within 10-720 seconds, within 10-30 minutes, within 30-720 minutes or intermediate or greater times), microstate data values (e.g., classification results as in 2010) to more normal values, for example, sufficient to change the classification. Other goal definitions may be used, for example, reducing a probability of classification by a threshold, such as at least 25%, 50%, 80% or intermediate or smaller or greater values. In another example, a classifying parameter, such as mean duration or mean frequency for one or more of the microstate types, is considered suitably affected if it changes so as to reduce a difference between current value and values considered normal, by at least 10%, 25%, 50%, 80% or intermediate values. Exemplary normal values are noted herein for NOR patients.

Optionally, treatment parameters are changed if classifier and/or classifying parameter values indicate an insufficient change in state. For example, TMS location may be changed and/or duration increased. Optionally, when testing a plurality of treatments or possible treatment parameter settings, treatments and/or settings are changed in response to test results, for example, increase if the result is positive and/or changing treatment if no effective change is found.

In some exemplary embodiments of the invention, MCI patients are treated with DEM treatments, for example, drugs (e.g., an Acetylcholinesterase inhibitor for example: donepezil, rivastigmine and galantamine or an NMDA receptor blocker like memantine, for example, using standard dosing protocols. Optionally, even if the patient is classified as MCI, DEM treatment may be applied. Optionally, if one of the cognitive tests and EEG tests indicates DEM, then even if the other tests do not agree, treatment (e.g., drugs) is applied. Optionally, a threshold is defined to treat MCI patients based on how close they are to DEM. In some exemplary embodiments of the invention, the assumption is that an MCI patient may be an incorrectly diagnosed DEM patient and/or may be in an earlier stage.

In any case, the effectiveness of such treatment is optionally assessed using microstate data. It is expected that microstate data can detect changes in patient condition with a higher sensitivity than traditional tests and thus be used to guide treatment in a more effective closed loop method. Optionally, feedback on drug efficacy is expected and used within 1-8 days and feedback on TMS or TCDC is expected within 5-360 minutes.

It is noted that 2012 may indicate that the patient still MCI (though improved or in a worse condition. In addition, 2014, assessment may indicate that the patient is not MCI (or if no treatment works sufficiently and/or progress does not match MCI) and a different diagnosis may be need. For example, a patient may be treated and move up form DEM to MCI, or may move up from MCI to NOR.

In addition, a patient may be identified as DEM. In such a patient it may be desired that mean durations go down and/or mean frequency goes up (e.g., towards MCI and/or NOR values). Optionally, a patient with typical dementia, may be expected to show a greater improvement than either an MCI patient or a patient with severe dementia (which may be defined according to a range of values of the mean duration and/or other parameter). The desired extend of change may be the same, smaller or larger than as described for an MCI patient.

It is noted that an effect of treatment on microstate parameter values may be temporary after treatment and then revert, e.g., with a reversion constant. Optionally, such reversion is tracked, for example, using a suitably programmed computer, for example, to detect a rate of reversion, which may have diagnostic significance (e.g., lower rate is better). This may be a same computer as used to select treatment, process EEG and/or microstates data and/or administer tests.

In some exemplary embodiments of the invention, the treatment is repeated so as to achieve a more stable change in microstate data, for example, as measured at a time which is delayed from an acute treatment by at least twice as long as the reversion constant, or at some other delay (e.g., 1-10 days, weeks and/or months) which results in the measurement reflecting a longer term effect. In some exemplary embodiments of the invention, treatment with TMS or TCDC is be repeated each week, for example, 2-3 times a week or less. Microstate measurement will optionally take place each treatment session. Long term positive effect will be considered if the microstate duration and/or freq change will stay stable between treatment sessions. The longer the duration of the stability, the better the patient response is considered.

In some exemplary embodiments of the invention, a treatment effect of stopping the disease and/or improvement is assessed using non-microstate methods, optionally in addition to microstate methods, for example, over a period of 3-24 months, for example, about 12 months.

Exemplary Diagnosis and/or Treatment for Depression

In some exemplary embodiments of the invention, patients diagnosed with depression will be evaluated for microstate freq and duration. If the parameters support a depression diagnosis, appropriate treatment will be given. If not, further evaluation using questionnaires and/or clinical and/or psychological evaluation may be used. In some exemplary embodiments of the invention, patients are treated with SSRI's/SNRI's/Neuroleptic drugs or other antidepressants or with TMS or TCDC treatment. Treatment effect is optionally evaluated using microstate analysis.

FIG. 21 is a flowchart of a method of diagnosing and optionally treating depression, in accordance with some embodiments of the invention.

At 2102, one or more non-EEG tests (e.g., cognitive, observational, psychiatric and/or biological) are optionally performed on a patient. In some cases, the test results are up to date. In some cases, test results from previous times, for example, 1-4 weeks or months in the past, or earlier, may be used.

At 2104-2108, EEG data may be collected and analyzed, for example as described herein, for example, at rest. Optionally, a classifier which combines duration based data (e.g., for all microstates) and frequency based data and/or other data, is optionally used.

At 2110, the patient may be classified as depressed, for example, based on the classifier and/or other data, for example, as provided in 2102, for example, a clinical phenotype. In some cases, the patient may be diagnosed as having dementia and treated, for example, as described herein.

In some embodiments, the patient is under continued care and may already have been diagnosed as having, for example, depression (or rather dementia or MCI) and/or having some cognitive problem. Previous treatment may already have started. Repeated testing, for example, as described in FIG. 21 may be performed periodically (e.g., on a time scale of 1-400 days, for example, between 1-10 days, between 10 and 50 days and/or between 50-400 days, or intermediate time scales), before and/or in response to treatment (e.g., an acute treatment such as electroshock, CBT, medication and/or electro- or magnetic-stimulation) and/or in response to a desired to change treatment (e.g., a long term treatment such as medication) (e.g., due to a side effect, perceived effectiveness and/or perceived ineffectiveness). In some exemplary embodiments of the invention, testing is repeated before and after treatment, optionally in a short time period, for example, within 0.5-72 hours, for example, between 1 and 5 hours. In some exemplary embodiments of the invention, a depressive state is monitored several times a day, for example, between 1-20 times a day, for example, between 2 and 5 times a day. Optionally, the patient is assessed at least once a week or 4 days or shorter or longer time periods. For example, if the patient is treated using drugs, assessment may be repeated once a week. If the patient is treated using intra cranial stimulation (magnetic and/or electric), assessment may be repeated, for example, every 30 minutes, for example, during a treatment session. Thereafter, assessment may be, for example, weekly and/or monthly.

In some exemplary embodiments of the invention, mean frequency is used to distinguish between DEP and NOR patients. While the results are not significant to p=0.05, they appear significant to a lower degree (0.08) and may also improve if other data is used for building a classifier. Mean frequency may be used to distinguish DEP from ALZ or DEM.

In some cases the diagnosis of DEP does not match other clinical diagnostic methods. Optionally, such mismatch is used to decide on a more conservative treatment and/or investigate further, such as using a broad cognitive testing, brain MRI, amyloidal testing and/or imaging, and/or PET and/or SPECT testing (e.g., with tagged glucose or Tc).

At 2112, if the patient is classified or otherwise identified as a DEP patient, treatment may be selected.

At 2116, the treatment is optionally applied and/or ongoing treatment continued.

At 2118, treatment may be changed, for example, if an ongoing treatment is not having a desired effect. For example, if mean duration and/or mean frequency and/or other clinical indicators are not improving (e.g., towards NOR values), then it is possible that the patient is misdiagnosed and/or that treatment should be changed. Regression in the direction of DEM values may indicate misdiagnosis.

Testing may be repeated to detect an effect of treatment. For example, a TMS treatment may be considered successful if it changes (e.g., within 0-10 seconds, within 10-720 seconds, within 10-30 minutes, within 30-720 minutes or intermediate or greater times), microstate data values (e.g., classification results as in 2110) to more normal values, for example, sufficient to change the classification. Other goal definitions may be used, for example, reducing a probability of classification by a threshold, such as at least 25%, 50%, 80% or intermediate or smaller or greater values. In another example, a classifying parameter, such as mean duration or mean frequency for one or more of the microstate types, is considered suitably affected if it changes so as to reduce a difference between current value and values considered normal, by at least 10%, 25%, 50%, 80% or intermediate values. Exemplary normal values are noted herein for NOR patients.

Optionally, treatment parameters are changed if classifier and/or classifying parameter values indicate an insufficient change in state. For example, TMS location may be changed and/or duration increased. Optionally, when testing a plurality of treatments or possible treatment parameter settings, treatments and/or settings are changed in response to test results, for example, increase if the result is positive and/or changing treatment if no effective change is found.

In some exemplary embodiments of the invention, mean durations (e.g., averages of all microstate durations or just using duration of just one microstate type) are used to distinguish patients with DEM from patients with DEP. This can be important as in many cases it is not easy to tell why a patient is not responsive. Mean frequency is optionally used to differentiate NOR from DEP In some exemplary embodiments of the invention, DEP patients are treated with drugs or ECT. Changes in mean frequency and/or mean duration may be used to indicate if the treatment is having a desired effect (e.g., reversion towards NOR).

Optionally, even if the patient is classified as MCI or DEM, DEP treatment may be applied. Optionally, if one of the cognitive tests and EEG tests indicates DEP, then even if the other tests do not agree, drug treatment or ECT treatment is applied.

In any case, the effectiveness of such treatment is optionally assessed using microstate data. It is expected that microstate data can detect changes in patient condition with a higher sensitivity than traditional tests and thus be used to guide treatment in a more effective closed loop method.

It is noted that 2112 may indicate that the patient still DEP (though improved or in a worse condition. In addition, 2114, assessment may indicate that the patient is not depressed (or if no treatment works sufficiently and/or progress does not match depression) and a different diagnosis may be need (e.g., DEM).

It is noted that an effect of treatment on microstate parameter values may be temporary after treatment and then revert, e.g., with a reversion constant. Optionally, such reversion is tracked, for example, using a suitably programmed computer, for example, to detect a rate of reversion, which may have diagnostic significance (e.g., lower rate is better). This may be a same computer as used to select treatment, process EEG and/or microstates data and/or administer tests.

In some exemplary embodiments of the invention, the treatment is repeated so as to achieve a more stable change in microstate data, for example, as measured at a time which is delayed from an acute treatment by at least twice as long as the reversion constant, or at some other delay (e.g., 1-10 days, weeks and/or months) which results in the measurement reflecting a longer term effect. In some exemplary embodiments of the invention, three months may be sufficient for treatment effect to last long enough. It is expected that after a few treatments, the improvement will be for progressively longer. Optionally, microstate analysis is used to if and when a next treatment is needed. In DEM, it is expected that treatment will be chronic. In DEM, once remission occurs, treatment may stop until diagnosis suggests a need and/or if period preventive treatment is desired.

General

It is expected that during the life of a patent maturing from this application many relevant methods for extracting microstate parameters values will be developed; the scope of the term extraction of microstate parameters values is intended to include all such new technologies a priori.

As used herein with reference to quantity or value, the term "about" means "within 10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, inhibiting, slowing or reversing the progression of a condition, ameliorating clinical or aesthetical symptoms of a condition or preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for generating a risk indication for depression by a device, comprising:
   receiving by the device resting state EEG data recorded from a subject when said subject is at a resting state and is not actively engaged in at least one of sensory processing and cognitive processing;
   analyzing the received resting state EEG data, wherein said analyzing comprises, extracting EEG microstates from said received resting state EEG data, and extracting values of one or more EEG microstate parameter from said EEG microstates;
   and
   generating by said device a risk indication for depression based on said extracted values of the one or more EEG microstate parameter, wherein said generating a risk indication comprises distinguishing said depression from a different disease state or from a non-disease state based on differences in said extracted values of said one or more EEG microstate parameter.

2. A method according to claim 1, wherein said one or more EEG microstate parameter comprises duration or mean duration.

3. A method according to claim 1, wherein said one or more EEG microstate parameter comprises frequency or mean frequency.

4. A method according to claim 1, wherein said generating a risk indication by said device comprises calculating by said device a score distinguishing said depression from one or both of the non-disease state and the different disease state, wherein the different disease state is a demented state.

5. A method according to claim 1, wherein said generating a risk indication by said device comprises calculating a score by said device indicating a severity of said depression.

6. A method according to claim 1, wherein said generating a risk indication by said device comprises a classifier stored in a memory of said device, and said classifier operated by said device to generate said risk indication.

7. A method according to claim 6, wherein said classifier stored in said memory uses a clinical phenotype in addition to said resting state EEG data for said generating a risk indication.

8. A method according to claim 1, wherein said receiving by the device comprises collecting said resting state EEG data for said analyzing after a treatment for depression in said subject is started and using said analyzing for feedback on the treatment.

9. A method according to claim 8, wherein said collecting comprises collecting said resting state EEG data after a treatment session of said treatment is completed.

10. A method according to claim 1, wherein said received resting stateEEG data is recorded by one or more electrodes during an EEG session.

11. A method according to claim 10, wherein said received resting state EEG data is recorded by one or more electrodes during an EEG session in which at least 50% of the session is with closed eyes.

12. A device for calculating a risk indication associated with depression, comprising:
   a memory, wherein the memory is configured to store microstates indications associated with depression;
   a control circuitry configured to connect to at least one EEG electrode configured to record EEG data, wherein the control circuitry is configured to extract EEG microstates from the recorded EEG data, and the control circuitry is further configured to extract values of one or more microstate parameter from the EEG microstates, wherein the memory is further configured to store the extracted values of one or more microstate parameter; and wherein said control circuitry is further configured to calculate a risk indication associated with depression based on the stored extracted values of the one or more microstate parameter and the stored microstates indications.

13. A device according to claim 12, wherein the microstate indications are stored in the form of a classifier.

14. A device according to claim 12, wherein said memory stores microstates indications associated with a dementia-related clinical condition, and wherein said control circuitry calculates a risk indication distinguishing between said depression and said dementia-related clinical condition based on the extracted values of the one or more microstate parameter and the microstates indications stored in the memory.

15. A device according to claim 14, wherein said dementia-related clinical condition comprises mild cognitive impairment (MCI).

16. A method according to claim 1, wherein said EEG microstate parameter comprises microstate mean duration, and wherein said distinguishing comprises distinguishing said depression from a demented state based on differences in said microstate mean duration.

17. A method according to claim 1, wherein said EEG microstate parameter comprises microstate mean frequency, and wherein said distinguishing comprises distinguishing said depression from a non-disease state based on differences in said microstate mean frequency.

18. A method according to claim 1, wherein said analyzing comprises clustering of the extracted EEG microstates into microstate clusters, wherein said extracting comprises extracting values of said one or more EEG microstate parameter for each microstate cluster of the microstate clusters, and wherein said distinguishing comprises distinguishing said depression from said different state or from said non-disease state based on differences in said extracted values between said microstate clusters.

19. A device according to claim 12, wherein said control circuitry is configured to cluster the extracted EEG microstates into microstate clusters and extract said values of one or more microstate parameter for each microstate cluster of the microstate clusters.

20. A device according to claim 19, wherein said microstate clusters comprise discrete topographic states of the EEG microstates, and wherein said control circuitry is configured to cluster the extracted EEG microstates into said microstate classes based on topographic similarity between some of the extracted EEG micro states.

* * * * *